US008871796B2

(12) United States Patent
Brown et al.

(10) Patent No.: US 8,871,796 B2
(45) Date of Patent: Oct. 28, 2014

(54) DIARYL ETHER DERIVATIVES AS NOTCH SPARING GAMMA SECRETASE INHIBITORS

(75) Inventors: William Colby Brown, Cleveland Heights, OH (US); Jason Brubaker, Cambridge, MA (US); Christian Fischer, Natick, MA (US); Richard W. Heidebrecht, Brookline, MA (US); John T. Hendrix, Charlottesville, VA (US); Elizabeth H. Kelley, Lynnfield, MA (US); Rachel N. MacCoss, Brookline, MA (US); Joey L. Methot, Westwood, MA (US); Thomas Miller, Brookline, MA (US); Karin M. Otte, Natick, MA (US); Phieng Siliphaivanh, Newton, MA (US); Thomas Reger, Lansdale, PA (US); Peter D. Williams, Harleysville, PA (US); Catherine M. Wiscount, Allentown, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 374 days.

(21) Appl. No.: 13/501,628

(22) PCT Filed: Oct. 5, 2010

(86) PCT No.: PCT/US2010/051442
§ 371 (c)(1),
(2), (4) Date: Sep. 28, 2012

(87) PCT Pub. No.: WO2011/046774
PCT Pub. Date: Apr. 21, 2011

(65) Prior Publication Data
US 2013/0053386 A1 Feb. 28, 2013

Related U.S. Application Data

(60) Provisional application No. 61/252,357, filed on Oct. 16, 2009, provisional application No. 61/372,966, filed on Aug. 12, 2010.

(51) Int. Cl.
*A61K 31/415* (2006.01)
*C07D 401/00* (2006.01)
*C07D 421/00* (2006.01)
*C07D 405/10* (2006.01)
*C07D 413/12* (2006.01)
*C07D 409/12* (2006.01)
*C07D 417/12* (2006.01)
*C07D 231/22* (2006.01)
*C07D 413/14* (2006.01)
*C07D 491/113* (2006.01)
*C07D 405/12* (2006.01)
*C07D 401/04* (2006.01)
*C07D 405/14* (2006.01)
*C07D 401/12* (2006.01)

(52) U.S. Cl.
CPC ............ *C07D 231/22* (2013.01); *C07D 405/10* (2013.01); *C07D 413/12* (2013.01); *C07D 409/12* (2013.01); *C07D 417/12* (2013.01); *C07D 413/14* (2013.01); *C07D 491/113* (2013.01); *C07D 405/12* (2013.01); *C07D 401/04* (2013.01); *C07D 405/14* (2013.01); *C07D 401/12* (2013.01)
USPC .......................... 514/406; 546/275.4; 546/193

(58) Field of Classification Search
None
See application file for complete search history.

(56) References Cited

U.S. PATENT DOCUMENTS

| 7,138,400 B2 | 11/2006 | Collins et al. |
| 2005/0085506 A1 | 4/2005 | Pissarnitski et al. |
| 2006/0264474 A1 | 11/2006 | Bettati et al. |
| 2007/0293567 A1 | 12/2007 | Wilson et al. |

FOREIGN PATENT DOCUMENTS

WO   2004/089911 A1   10/2004

OTHER PUBLICATIONS

Doerfler, et al., "Presenilin-dependent gamma-secretase activity modulates thymocyte development," PNAS, 2001, vol. 98, No. 16, pp. 9312-9317.
Hadland, et al., "Gamma-Secretase inhibitors repress thymocyte development," PNAS, 2001. vol. 98, No. 13, pp. 7487-7491.
Milano, et al, "Modulation of Notch Processing by gamma-secretase Inhibitors Causes Intestinal Goblet Cell Metaplasia and Induction of Genes Known to Specify Gut Secretory Lineage Differentiation," Toxicological Sciences, 2004, vol. 82, No. 1, pp. 341-358.
Searfoss, et al., "Adipsin, a Biomarker of Gastrointestinal Toxicity Mediated by a Functional gamma-secretase Inhibitor," Journal of Biological Chemistry, 2003, vol. 278, No. 46, pp. 46107-46116.
van Es, et al., "Notch/gamma-secretase inhibition turns proliferative cells in intestinal crypts and adenomas into goblet cells," Nature, 2005, vol. 435, pp. 959-963.
Wong, et al., "Chronic Treatment with the gamma-secretase Inhibitor LY-411,575 Inhibits Beta-Amyloid Peptide Production and Alters Lymphopoiesis and Intestinal Cell Differentiation," Journal of Biological Chemistry, 2004, vol. 279, No. 13, pp. 12879-12882.
WO11046774 Search Report, Apr. 21, 2011.

*Primary Examiner* — Jeffrey S. Lundgren
*Assistant Examiner* — Michael Schmitt
(74) *Attorney, Agent, or Firm* — J. Eric Thies; John C. Todaro

(57) ABSTRACT

The invention encompasses a novel class of diaryl ether derivatives which inhibit the processing of APP by the putative γ-secretase while sparing Notch signaling pathway, and thus are useful in the treatment or prevention of Alzheimer's disease without the development of Notch inhibition mediated gastrointestinal issues. Pharmaceutical compositions and methods of use are also included.

17 Claims, No Drawings

DIARYL ETHER DERIVATIVES AS NOTCH SPARING GAMMA SECRETASE INHIBITORS

BACKGROUND OF THE INVENTION

The present invention relates to a novel class of compounds, their salts, pharmaceutical compositions comprising them and their use in therapy of the human body. In particular, the invention relates to novel diaryl ether derivatives which inhibit the processing of APP by γ-secretase, and hence are useful in the treatment or prevention of Alzheimer's disease. The compounds of the invention also spare the Notch signaling pathway. As such, the compounds of the invention are believed to halt or potentially reverse the progression of Alzheimer's disease without the development of toxicities mediated by Notch inhibition.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by a progressive loss of memory and cognitive function, and pathologically characterized by the deposition of extracellular proteinaceous plaques in the cortical and associative brain regions of sufferers. These plaques are mainly comprised of fibrillar aggregates of β-amyloid peptide (Aβ) (Glenner G G and Wong C W (1984) Alzheimer's disease: Initial report of the purification and characterization of a novel cerebrovascular amyloid protein. Biochemical and Biophysical research Communications, 120(3); 885-890). The role of secretases, including that of γ-secretase, in the processing of amyloid precursor protein (APP) to form Aβ is well documented in the literature. Aβ is generated by proteolytic processing of APP by two enzymes, β-amyloid cleavage enzyme (BACE) and γ-secretase (FIG. 1; Selkoe D J (2001) Alzheimer's disease: genes, proteins, and therapy. Physiological Review. 81(2):741-766). γ-Secretase is a complex comprised of four proteins: presenilin (presenilin-1 or -2), nicastrin, APH-1 and PEN-2 (Takasugi N, Tomita T, Hayashi I, Tsuruoka M, Niimura M, Takahashi Y, Thinakaran G, Iwatsubo T (2003) The role of presenilin cofactors in the gamma-secretase complex. Nature. 422(6930):438-441; Kimberly W T, LaVoie M J, Ostaszewski B L, Ye W, Wolfe M S, Selkoe D J (2003) Gamma-secretase is a membrane protein complex comprised of presenilin, nicastrin, Aph-1, and Pen-2. Proceedings of the National Academy of Sciences. 100 (11):6382-6387; Edbauer D, Winkler E, Regula J T, Pesold B, Steiner H, Haass C (2003) Reconstitution of gamma-secretase activity. Nature Cell Biology. 5(5):486-488.). Presenilin-1 and -2 contain transmembrane aspartyl residues that have been shown to be essential for the catalytic activity of the complex (Wolfe M S, Xia W, Ostaszewski B L, Diehl T S, Kimberly W T, Selkoe D J (1999) Two transmembrane aspartates in presenilin-1 required for presenilin endoproteolysis and gamma-secretase activity. Nature. 1999 398(6727):513-517). The majority of the mutations linked to the early onset, familial form of AD (FAD) are associated with either PS-1 or PS-2 (Schemer D, Eckman C, Jensen M, Song X, Citron M, Suzuki N, Bird T D, Hardy J, Hutton M, Kukull W, Larson E, Levy-Lahad E, Viitanen M, Peskind E, Poorkaj P, Schellenberg G, Tanzi R, Wasco W, Lannfelt L, Selkoe D, Younkin S (1996) Secreted amyloid beta-protein similar to that in the senile plaques of Alzheimer's disease is increased in vivo by the presenilin 1 and 2 and APP mutations linked to familial Alzheimer's disease. Nature Medicine. 2(8):864-870; Duff K, Eckman C, Zehr C, Yu X, Prada C M, Perez-tur J, Hutton M, Buee L, Harigaya Y, Yager D, Morgan D, Gordon M N, Holcomb L, Refolo L, Zenk B, Hardy J, Younkin S (1996) Increased amyloid-beta42(43) in brains of mice expressing mutant presenilin 1. Nature. 383(6602):710-713; Lernere C A, Lopera F, Kosik K S, Lendon C L, Ossa J, Saida T C, Yamaguchi H, Ruiz A, Martinez A, Madrigal L, Hincapie L, Arango J C, Anthony D C, Koo E H, Goate A M, Selkoe D J, Arango J C (1996) The E280A presenilin 1 Alzheimer mutation produces increased A beta 42 deposition and severe cerebellar pathology. Nature Medicine. 2(10):1146-1150; Citron M, Westaway D, Xia W, Carlson G, Diehl T, Levesque G, Johnson-Wood K, Lee M, Seubert P, Davis A, Kholodenko D, Molter R, Sherrington R, Perry B, Yao H, Strome R, Lieberburg I, Rommens Jr, Kim 5, Schenk D, Fraser P, St George Hyslop P, Selkoe D J (1997) Mutant presenilins of Alzheimer's disease increase production of 42-residue amyloid beta-protein in both transfected cells and transgenic mice. Nature Medicine. 3(1):67-72). γ-Secretase processes a number of other type I membrane proteins that have undergone a prerequisite ectodomain shedding (Lleó A (2008) Activity of gamma-secretase on substrates other than APP. Current Topics in Medicinal Chemistry. 8(1):9-16).

In addition to processing APP, γ-secretase cleaves the Notch family of receptors. Genetic evidence indicates that γ-secretase activity is critically required for Notch signaling and functions (Shen J, Bronson R T, Chen D F, Xia W, Selkoe D J, Tonegawa S (1997) Skeletal and CNS defects in Presenilin-1-deficient mice. Cell. 89(4):629-639; Wong P C, Zheng H, Chen H, Becher M W, Sirinathsinghji D J, Trumbauer M E, Chen H Y, Price D L, Van der Ploeg L H, Sisodia S S (1997) Presenilin 1 is required for Notch1 and Dll1 expression in the paraxial mesoderm. Nature. 387(6630):288-292). Notch is an evolutionarily conserved and widely expressed single-span type I transmembrane receptor that plays a prominent role in regulating cell fate decisions in the developing embryo (Artavanis-Tsakonas S, Rand M D, Lake R J (1999) Notch signaling: cell fate control and signal integration in development. Science. 284(5415):770-776). The role of Notch in the adult remains unclear but Notch proteins are expressed in various adult tissues and are thought to play a role in regulating stem cell differentiation. Four Notch genes have been identified in mammals (Notch 1-4); all four Notch proteins are cleaved by γ-secretase (Saxena M T, Schroeter E H, Mumm J S, Kopan R (2001) Murine notch homologs (N-1-4) undergo presenilin-dependent proteolysis. Journal of Biological Chemistry. 276(43):40268-40273). Notch activation is induced by binding, in trans, to the Delta/Serrate/LAG2 family of transmembrane ligands. Notch signal transduction is mediated by three cleavage events: (a) cleavage at Site 1 in extracellular domain; (b) cleavage at Site 2 just N-terminal to the extracellular/transmembrane domain boundary following ligand binding; and (c) cleavage at Site 3 (S3) within the transmembrane near the transmembrane/cytoplasmic domain boundary. Site 3 cleavage is required for release of Notch intracellular domain (NICD) and is mediated by γ-secretase (Schroeter E H, Kisslinger J A, Kopan R (1998) Notch-1 signalling requires ligand-induced proteolytic release of intracellular domain. Nature. 393(6683):382-386). NICD activates transcription mediated by the (CSL) CBF1/Serrate/LAG-1 family of DNA binding proteins and induces expression of various genes. NICD-regulated transcription is thought to be a key component of Notch-mediated signal transduction.

The development of γ-secretase inhibitors to block APP cleavage and Aβ generation is hampered by the potential for mechanism-based toxicity due to inhibition of Notch processing. Notch-related toxicities have been observed in studies where animals have been dosed subchronically with γ-secretase inhibitors. Intestinal goblet cell metaplasia is consistently observed following three or more days of treatment (Searfoss G H, Jordan W H, Calligaro D O, Galbreath E J, Schirtzinger L M, Berridge B R, Gao H, Higgins M A, May P C, Ryan T P (2003) Adipsin, a biomarker of gastrointestinal toxicity mediated by a functional gamma-secretase inhibitor. Journal of Biological Chemistry. 278(46):46107-46116; Wong G T, Manfra D, Poulet F M, Zhang Q, Josien H, Bara T, Engstrom L, Pinzon-Ortiz M, Fine J S, Lee H J, Zhang L, Higgins G A, Parker E M (2004) Chronic treatment with the gamma-secretase inhibitor LY-411,575 inhibits beta-amyloid peptide production and alters lymphopoiesis and intestinal cell differentiation. Journal of Biological Chemistry. 279 (13):12876-12882; Milano 3, McKay 3, Dagenais C, Foster-Brown L, Pognan F, Gadient R, Jacobs R T, Zacco A, Greenberg B, Ciaccio P J (2004) Modulation of notch processing by gamma-secretase inhibitors causes intestinal goblet cell metaplasia and induction of genes known to specify gut secretory lineage differentiation. Toxicological Sciences. 82(1): 341-358; van Es J H, van Gijn M E, Riccio O, van den Born M, Vooijs M, Begthel H, Cozijnsen M, Robine S, Winton D J, Radtke F, Clevers H (2005) Notch/gamma-secretase inhibition turns proliferative cells in intestinal crypts and adenomas into goblet cells. Nature. 435(7044):959-963). In addition, Notch function appears to be critical for the proper differentiation of T and B lymphocytes (Hadland B K, Manley N R, Su D, Longmore G D, Moore C L, Wolfe M S, Schroeter E H, Kopan R (2001) Gamma-secretase inhibitors repress thymocyte development. Proceedings of the National Academy of Sciences. 98(13):7487-7491; Doerfler P, Sheannan M S, Perlmutter R M (2001) Presenilin-dependent gamma-secretase activity modulates thymocyte development. Proceedings of the National Academy of Sciences. 98(16):9312-9317). Thus, pharmacologically targeting γ-secretase activity requires agents that selectively block Aβ while minimally inhibiting activity towards Notch.

The present invention provides a novel class of diaryl ether derivatives which inhibit the processing of APP by the putative γ-secretase while sparing Notch signaling pathway, and thus are useful in the treatment or prevention of AD. WO 2004/089911A1 discloses a class of pyrazole derivatives as gamma-secretase inhibitors. However, compounds disclosed in WO 2004/089911 A1 exhibit poor metabolic stability, which translates into poor in vivo pharmacokinetics and little or no efficacy in vivo. Compounds of the present invention possess favorable in vivo pharmacokinetics and are efficacious (inhibit the processing of APP) in vivo.

SUMMARY OF THE INVENTION

The invention encompasses a novel class of diaryl ether derivatives which inhibit the processing of APP by the putative γ-secretase while sparing Notch signaling pathway, and thus are useful in the treatment or prevention of Alzheimer's disease without the development of Notch inhibition mediated gastrointestinal issues. Pharmaceutical compositions and methods of use are also included.

DETAILED DESCRIPTION OF THE INVENTION

The invention encompasses compounds of formula I:

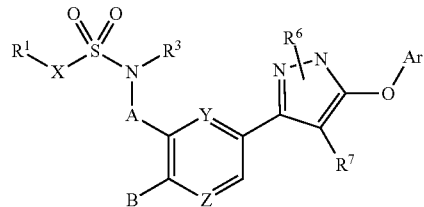

or a pharmaceutically acceptable salt thereof, wherein:
A represents —C($R^4$)($R^5$)— and B represent H, or A and B are joined together to form the following group:

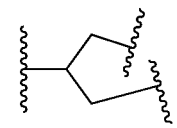 [SMILES: *CC(*)C*]

Y and Z independently represent $CR^{11}$ or N, wherein $R^{11}$ is H or halogen;
X represents a bond, O or $NR^2$;
$R^1$ represents a linear, branched or cyclic, or combination thereof, hydrocarbon group of 1-10 carbon atoms, which is optionally substituted with up to 3 halogen atoms; or when X represents $NR^2$, $R^1$ and $R^2$ together may complete a heterocyclic ring of up to 6 members which optionally bears up to 3 substituents independently selected from halogen, $CF_3$, $CHF_2$, $CH_2F$, $NO_2$, CN, $OCF_3$, $C_{1-6}$alkyl and $C_{1-6}$alkoxy;
$R^2$ represents H or $C_{1-4}$alkyl, or together with $R^1$ completes a heterocyclic ring as defined above;
$R^3$ represents H or $C_{1-4}$alkyl;
$R^4$ represents $C_{1-6}$alkyl,
$R^5$ represents H or $C_{1-6}$alkyl;
or $R^4$ and $R^5$ may be joined together with the atom to which they are attached to form a spirocyclic ring of 3, 4 or 5 atoms, said ring optionally containing a heteroatom selected from O, S or N;
$R^6$ is bonded to one of the nitrogen atoms of the pyrazole ring and represents a hydrocarbon group of 1-5 carbon atoms which is optionally substituted with 1-3 substituents independently selected from $R^8$;
$R^7$ represents H, halogen, CN, formyl, phenylethynyl or $C_{1-6}$alkyl;
Ar represents phenyl or 6-membered heteroaryl, either of which bears 0-3 substituents independently selected from $R^8$;
$R^8$ is selected from the group consisting of: halogen, OH, CN, $R^{10}$, $OR^9$, $SR^{10}$, $SO_2R^{10}$, $SO_2N(R^9)_2$, $COR^9$, $CO_2R^9$, $CON(R^9)_2$, $N(R^9)_2$, $NO_2$, $NR^9COR^{10}$, $NR^9CO_2R^9$, $NR^9CH_2CO_2R^9$, $NR^9SO_2R^{10}$, —$C_{1-4}$alkyl-$N(R^9)_2$, —$C_{1-4}$alkyl-$NR^9COR^{10}$, —$C_{1-4}$alkyl-$NR^9CO_2R^9$ and —$C_{1-4}$alkyl-$NR^9CH_2CO_2R^9$;
each $R^9$ is independently selected from: (1) H, $C_{1-6}$alkyl, $C_{3-10}$cycloalkyl, $C_{3-10}$cycloalkyl$C_{1-4}$alkyl, $C_{3-10}$cycloalkenyl or $C_{3-10}$cycloalkenyl$C_{1-4}$alkyl, any of which except H optionally bear up to 4 halogen atoms or with OH, CN, $CF_3$ and $C_{1-4}$alkoxy, or both; (2) phenyl, benzyl, 5- or 6-membered monocyclic heteroaryl optionally bridged with a methylene or a 9- or 10-membered bicyclic heteroaryl optionally bridged with a methylene, any of which optionally bear up to 3 substituents independently selected from halogen, OH, CN, $CF_3$, $C_{1-4}$alkyl, $C_{3-6}$cycloalkyl, phenyl, $C_{1-4}$alkoxy, amino, $C_{1-4}$alkylamino and di($C_{1-4}$alkyl)amino; and (3) a nonaromatic or partially aromatic mono- or bicyclic heterocyclic system of up to 10 ring atoms, optionally bridged with a methylene and optionally bearing up to 3 substituents independently selected from halogen, OH, oxo, CN, $CF_3$, $C_{1-4}$alkyl, $C_{3-6}$cycloalkyl, phenyl, a 5- or 6-membered monocyclic heteroaryl, $C_{1-4}$alkoxy, acetyl, amino, $C_{1-4}$alkylamino and di($C_{1-4}$alkyl)amino; or when two $R^9$ groups are attached to the same nitrogen atom they may be joined together with the nitrogen atom to complete a mono- or bicyclic heterocyclic ring of up to 10 members which optionally bears up to 3 substituents independently selected from halogen, $CF_3$, $CHF_2$, $CH_2F$, $NO_2$, CN, $OCF_3$, acetyl, formyl, $C_{1-6}$alkyl and $C_{1-6}$alkoxy; and $R^{10}$ has the same definition as $R^9$ except that $R^{10}$ is not H.

The invention also encompasses compounds of Formula I wherein: Y and Z each represent CH; Ar represent phenyl, which bears 0-3 substituents independently selected from $R^8$; $R^3$ represents H; $R^7$ represents H; A represents —C($R^4$)($R^5$)— and B represent H; $R^4$ and $R^5$ are methyl or $R^4$ and $R^5$ are joined together with the atom to which they are attached to form cyclopropyl, cyclobutyl or oxetanyl; and X represents a bond or $NR^2$.

The invention encompasses a genus of compounds according to Formula I

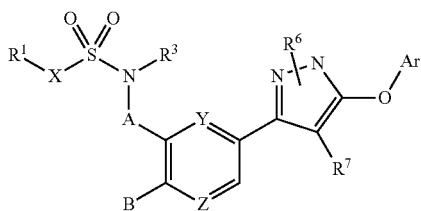

I or a pharmaceutically acceptable salt thereof, wherein:

A represents —C($R^4$)($R^5$)— and B represent H, or A and B are joined together to form the following group:

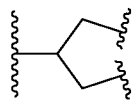

Y and Z independently represent $CR^{11}$ or N, wherein $R^{11}$ is H or halogen;

X represents a bond, O or $NR^2$;

$R^1$ represents a linear, branched or cyclic, or combination thereof, hydrocarbon group of 1-10 carbon atoms, which is optionally substituted with up to 3 halogen atoms; or when X represents $NR^2$, $R^1$ and $R^2$ together may complete a heterocyclic ring of up to 6 members which optionally bears up to 3 substituents independently selected from halogen, $CF_3$, $CHF_2$, $CH_2F$, $NO_2$, CN, $OCF_3$, $C_{1-6}$alkyl and $C_{1-6}$alkoxy;

$R^2$ represents H or $C_{1-4}$alkyl, or together with $R^1$ completes a heterocyclic ring as defined above;

$R^3$ represents H or $C_{1-4}$alkyl;

$R^4$ represents $C_{1-6}$alkyl, $R^5$ represents H or $C_{1-6}$alkyl;

or $R^4$ and $R^5$ may be joined together with the atom to which they are attached to form a spirocyclic ring of 3, 4 or 5 atoms, said ring optionally containing a heteroatom selected from O, S or N;

$R^6$ is bonded to one of the nitrogen atoms of the pyrazole ring and represents a hydrocarbon group of 1-5 carbon atoms which is optionally substituted with up to 3 halogen atoms or hydroxy;

$R^7$ represents H, halogen, CN, formyl, phenylethynyl or $C_{1-6}$alkyl;

Ar represents phenyl or 6-membered heteroaryl, either of which bears 0-3 substituents independently selected from $R^8$;

$R^8$ is selected from the group consisting of: halogen, OH, CN, $R^{10}$, $OR^9$, $SR^{10}$, $SO_2R^{10}$, $SO_2N(R^9)_2$, $COR^9$, $CO_2R^9$, $CON(R^9)_2$, $N(R^9)_2$, $NO_2$, $NR^9COR^{10}$, $NR^9CO_2R^9$, $NR^9CH_2CO_2R^9$, $NR^9SO_2R^{10}$, —$C_{1-4}$alkyl-$N(R^9)_2$, —$C_{1-4}$alkyl-$NR^9COR^{10}$, —$C_{1-4}$alkyl-$NR^9CO_2R^9$ and —$C_{1-4}$alkyl-$NR^9CH_2CO_2R^9$;

each $R^9$ is independently selected from: (1) H, $C_{1-6}$alkyl, $C_{3-10}$cycloalkyl, $C_{3-10}$cycloalkyl$C_{1-4}$alkyl, $C_{3-10}$cycloalkenyl or $C_{3-10}$cycloalkenyl$C_{1-4}$alkyl, any of which except H optionally bear up to 4 halogen atoms or with OH, CN, $CF_3$ and $C_{1-4}$alkoxy, or both; (2) phenyl, benzyl, 5- or 6-membered monocyclic heteroaryl optionally bridged with a methylene or a 9- or 10-membered bicyclic heteroaryl optionally bridged with a methylene, any of which optionally bear up to 3 substituents independently selected from halogen, OH, CN, $CF_3$, $C_{1-4}$alkyl, $C_{3-6}$cycloalkyl, phenyl, $C_{1-4}$alkoxy, amino, $C_{1-4}$alkylamino and di($C_{1-4}$alkyl)amino; and (3) a nonaromatic or partially aromatic mono- or bicyclic heterocyclic system of up to 10 ring atoms, optionally bridged with a methylene and optionally bearing up to 3 substituents independently selected from halogen, OH, oxo, CN, $CF_3$, $C_{1-4}$alkyl, $C_{3-6}$cycloalkyl, phenyl, a 5- or 6-membered monocyclic heteroaryl, $C_{1-4}$alkoxy, acetyl, amino, $C_{1-4}$alkylamino and di($C_{1-4}$alkyl)amino; or when two $R^9$ groups are attached to the same nitrogen atom they may be joined together with the nitrogen atom to complete a mono- or bicyclic heterocyclic ring of up to 10 members which optionally bears up to 3 substituents independently selected from halogen, $CF_3$, $CHF_2$, $CH_2F$, $NO_2$, CN, $OCF_3$, acetyl, formyl, $C_{1-6}$alkyl and $C_{1-6}$alkoxy; and $R^{10}$ has the same definition as $R^9$ except that $R^{10}$ is not H.

Within the genus, the invention encompasses a first sub-genus of compounds of Formula I wherein Ar represent phenyl, which bears 0-3 substituents independently selected from $R^8$.

Within the first sub-genus, the invention encompasses a first class of compounds of Formula I wherein Ar represents 4-$CF_3$-phenyl.

Also within the genus, the invention encompasses a second sub-genus of compounds of Formula I wherein $R^6$ is bonded to one of the nitrogen atoms of the pyrazole ring and represents ethyl.

Also within the genus, the invention encompasses a third sub-genus of compounds of Formula I wherein A represents —C($R^4$)($R^5$)— and B represent H.

Within the third sub-genus, the invention encompasses a second class of compounds of Formula I wherein $R^4$ and $R^5$ are methyl.

Also within the third sub-genus, the invention encompasses a third class of compounds of Formula I wherein $R^4$ and $R^5$ are joined together with the atom to which they are attached to form cyclopropyl, cyclobutyl or oxetanyl.

Also within the genus, the invention encompasses a fourth sub-genus of compounds of Formula I wherein A and B are joined together to form the following group:

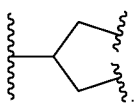

Also within the genus, the invention encompasses a fifth sub-genus of compounds of Formula I wherein X represents a bond.

Within the fifth sub-genus, the invention encompasses a fourth class of compounds of Formula I wherein $R^1$ represent $CF_3$—$CH_2$—.

Also within the genus, the invention encompasses a sixth sub-genus of compounds of Formula I wherein X represents $NR^2$.

Also within the genus, the invention encompasses a seventh sub-genus of compounds of Formula I wherein Y and Z each represent CH.

Also within the genus, the invention encompasses an eighth sub-genus of compounds of Formula I wherein:

Y and Z each represent CH;
Ar represent phenyl, which bears 0-3 substituents independently selected from $R^8$;
$R^3$ represents H;
$R^6$ is bonded to one of the nitrogen atoms of the pyrazole ring and represents ethyl;
$R^7$ represents H;
A represents —C($R^4$)($R^5$)— and B represent H;
$R^4$ and $R^5$ are methyl or $R^4$ and $R^5$ are joined together with the atom to which they are attached to form cyclopropyl, cyclobutyl or oxetanyl; and
X represents a bond or $NR^2$.

The invention also encompasses any of the examples that follow.

The invention also encompasses a pharmaceutical composition comprising a compound according to formula I or a pharmaceutically acceptable salt thereof and a pharmaceutically acceptable carrier.

The invention also encompasses a method of treatment of a subject suffering or prone to a condition associated with the deposition of β-amyloid which comprises administering to that subject an effective amount of a compound according to formula I or a pharmaceutically acceptable salt thereof.

The invention also encompasses the use of a compound according to formula I or a pharmaceutically acceptable salt thereof for the manufacture of a medicament for treating or preventing Alzheimer's disease.

Where a variable occurs more than once in formula I or in a substituent thereof, the individual occurrences of that variable are independent of each other, unless otherwise specified.

The term "bicyclic" includes fused, bridged and spiro rings.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, benzenesulphonic acid, fumaric acid, maleic acid, succinic acid, acetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

It is to be emphasized that the invention, for each compound in accordance with formula I, encompasses both enantiomeric forms, either as homochiral compounds or as mixtures of enantiomers in any proportion. Where the compounds according to the invention possess two or more asymmetric centers, they may additionally exist as diastereoisomers. It is to be understood that all such isomers and mixtures thereof in any proportion are encompassed within the scope of the present invention.

It will also be appreciated that where more than one isomer can be obtained from a reaction then the resulting mixture of isomers can be separated by conventional means. Where the processes for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary. Alternatively, such techniques may be carried out on racemic synthetic precursors of the compounds of interest.

In the compounds of generic formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

The compounds of the present invention have activity as inhibitors of γ secretase.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil or coconut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly-ethylene glycol), polyvinylpyrrolidone) or gelatin.

The present invention also provides a compound of the invention or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of the present invention or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound according to the present invention or a pharmaceutically acceptable salt thereof.

For treating or preventing Alzheimer's disease, a suitable dosage level is about 0.01 to 250 mg/kg per day, preferably about 0.01 to 100 mg/kg per day, more preferably about 0.05 to 50 mg/kg of body weight per day, and for the most preferred compounds, about 0.1 to 10 mg/kg of body weight per day. The compounds may be administered on a regimen of 1 to 4 times per day. In some cases, however, a dosage outside these limits may be used.

The following examples illustrate the present invention. Where they are not commercially available, the starting materials and reagents used in the synthetic schemes may be prepared by conventional means. The invention also encompasses a compound selected from the examples that follow.

During any of the synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

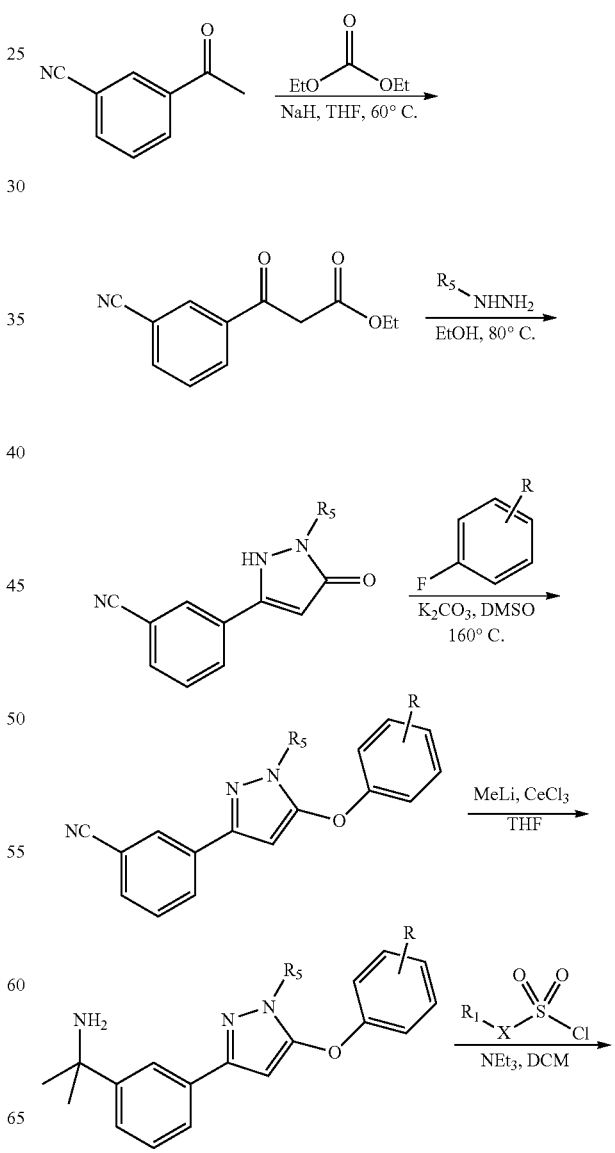

Scheme 1. Synthesis of Example 1.

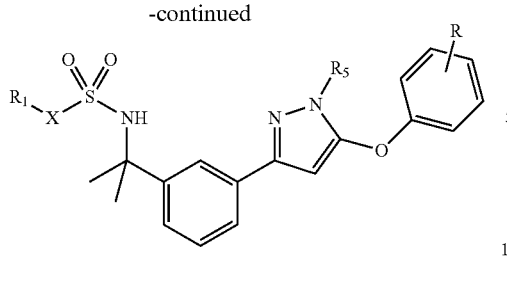
Scheme 2. Synthesis of Example 16.
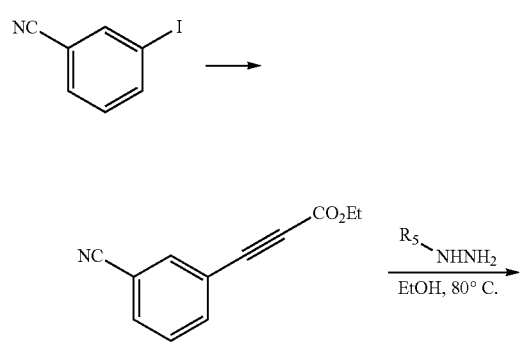
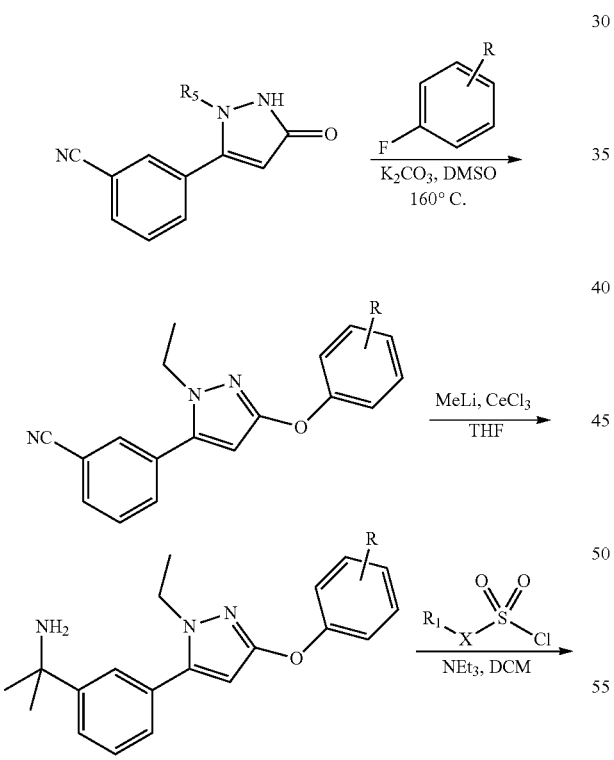
Scheme 3. Synthesis of Cyclopropyl Derivatives.
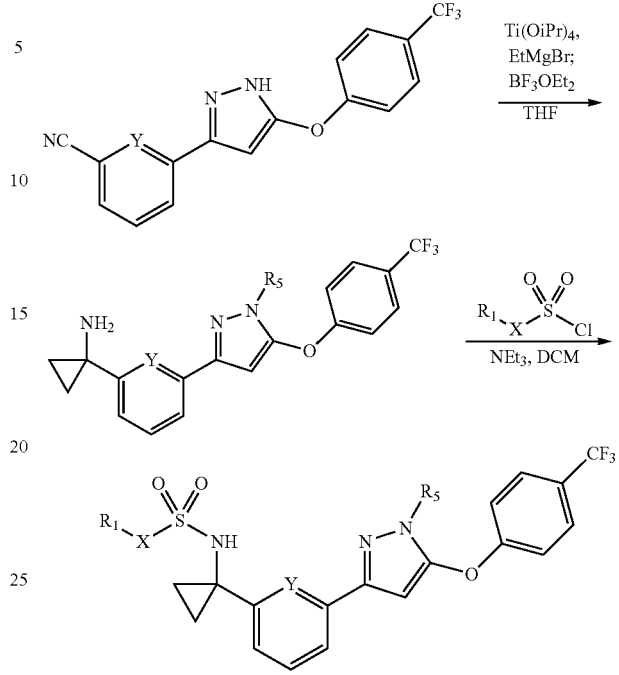
Scheme 4.
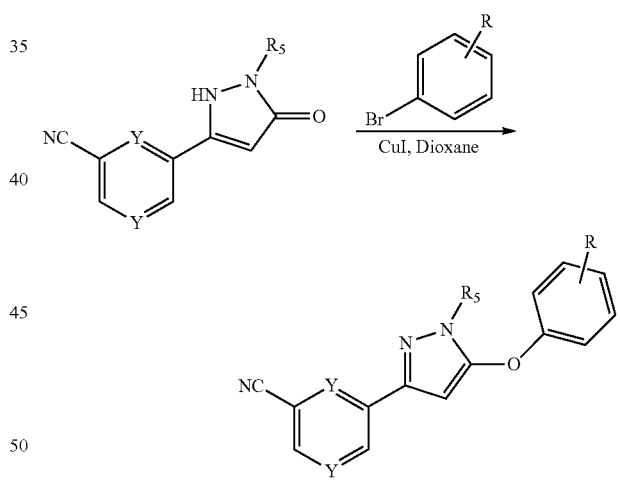
Scheme 5. Synthesis of Example 61.
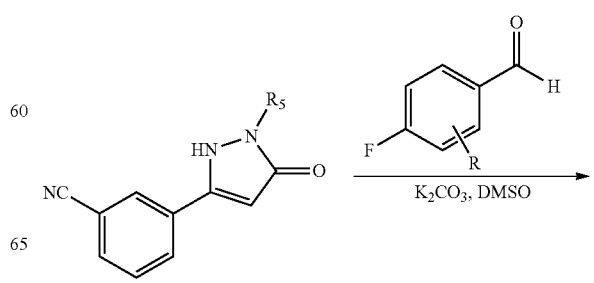

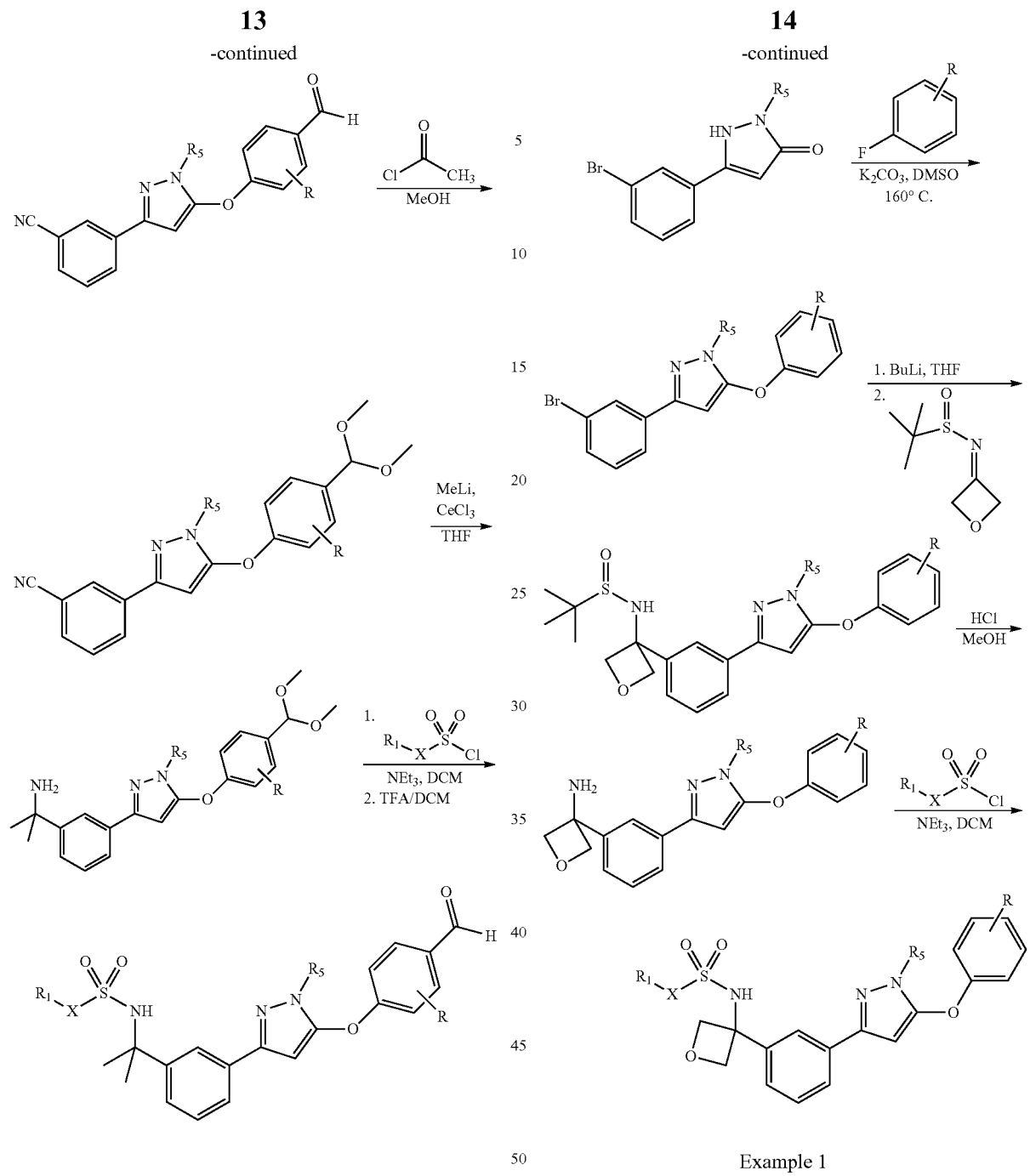
Scheme 6. Synthesis of Oxetane Derivatives.
Example 1
N-[1-(3-{1-ethyl-5-[4-(trifluoromethyl)phenoxy]-1H-pyrazol-3-yl}phenyl)-1-methylethyl]-2,2,2-trifluoroethanesulfonamide
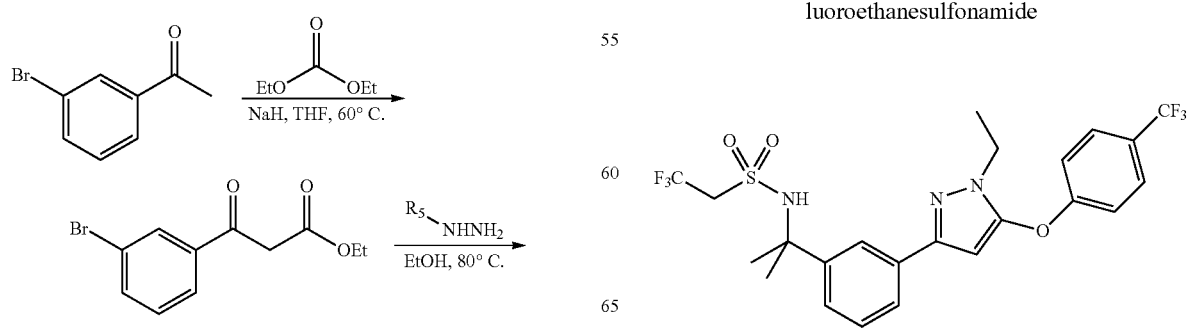

Step 1:

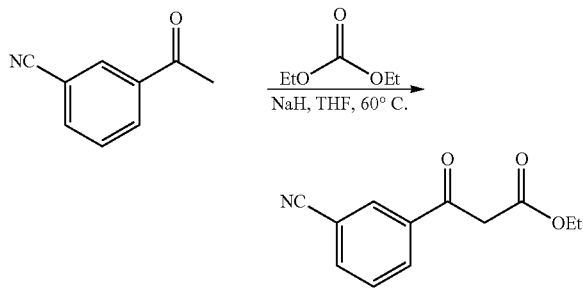

Sodium hydride (60% dispersion in oil, 8.27 g, 207 mmol, 3.00 equiv) was added to a solution of 3-acetylbenzonitrile (10.0 g, 68.9 mmol, 1 equiv) in tetrahydrofuran (300 mL). The reaction mixture was stirred at 60° C., and a solution of diethyl carbonate (12.5 mL, 103 mmol, 1.50 equiv) in tetrahydrofuran (60 mL) was added over 45 minutes. The light orange reaction mixture was stirred at 60° C. for an additional 2 h, then was cooled to 22° C. Saturated aqueous ammonium chloride solution was added, and the mixture was concentrated to ~½ volume by rotary evaporation. The resulting residue was partitioned between ethyl acetate and water. The organic layer was washed with saturated aqueous sodium chloride solution, and the washed solution was dried over sodium sulfate. The dried solution was filtered, and the filtrate was concentrated to afford ethyl 3-(3-cyanophenyl)-3-oxo-propanoate (15 g, 100%) as a white solid. The crude reaction product was taken into the next step without further purification. Calcd (M+1)⁺: 218.1. Found: 218.0.

Step 2:

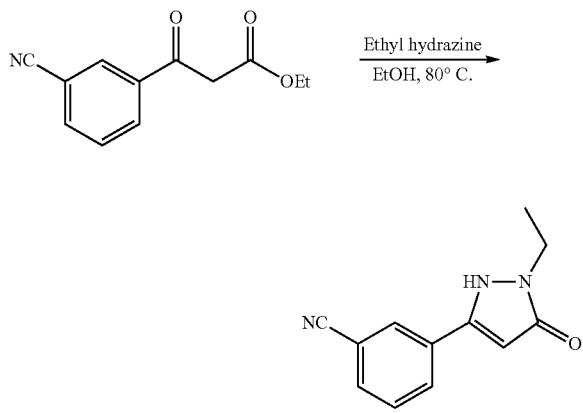

Ethyl hydrazine oxalate (15.6 g, 104 mmol, 1.50 equiv) was added to a solution of ethyl 3-(3-cyanophenyl)-3-oxo-propanoate (15.0 g, 69.1 mmol, 1 equiv) and triethylamine (14.4 mL, 104 mmol, 1.50 equiv) in ethanol (345 mL). The reaction mixture was heated to 80° C. for 70 min, then was removed from heat an concentrated to ~¼ volume by rotary evaporation. The residue was partitioned between ethyl acetate and water. The organic layer was washed with saturated aqueous sodium chloride solution, and the washed solution was dried over sodium sulfate. The dried solution was filtered, and the filtrate was concentrated to afford 3-(1-ethyl-5-oxo-2,5-dihydro-1H-pyrazol-3-yl)benzonitrile as a light-yellow solid (18.1 g) of sufficient purity to use in the next step without further purification. Calcd (M+1)⁺: 214.1. Found: 214.1.

Step 3:

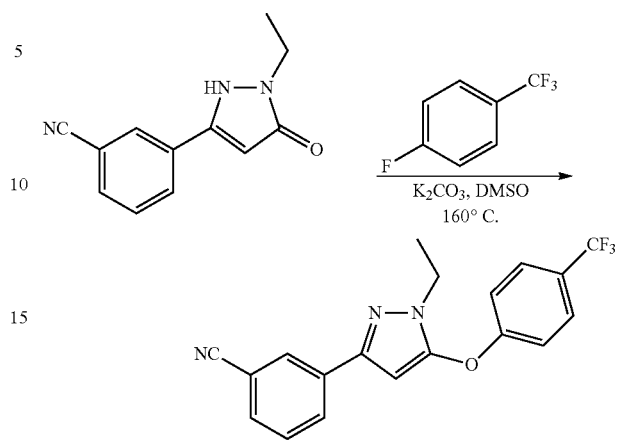

1-fluoro-4-(trifluoromethyl)benzene (22.9 mL, 180 mmol, 6.00 equiv) was added to a mixture of 3-(1-ethyl-5-oxo-2,5-dihydro-1H-pyrazol-3-yl)benzonitrile (6.40 g, 30.0 mmol, 1 equiv) and potassium carbonate (12.4 g, 90.0 mmol, 3.00 equiv) in dimethyl sulfoxide (60 mL) in a high pressure reaction vessel. The vessel was sealed, and the reaction mixture was heated to 160° C. After stirring for 16 hours, the high pressure vessel was cooled to 22° C. and the reaction mixture was partitioned between ethyl acetate and water. The organic layer was washed with saturated aqueous sodium chloride solution, and the washed solution was dried over sodium sulfate. The dried solution was filtered, and the filtrate was concentrated. The residue was purified by flash-column chromatography (hexanes, grading to 50% ethyl acetate-hexanes) to afford 3-{1-ethyl-5-[4-(trifluoromethyl)phenoxy]-1H-pyrazol-3-yl}benzonitrile (4.70 g, 44%) as a white solid. Calcd (M+1)⁺: 357.1. Found: 358.0.

Step 4:

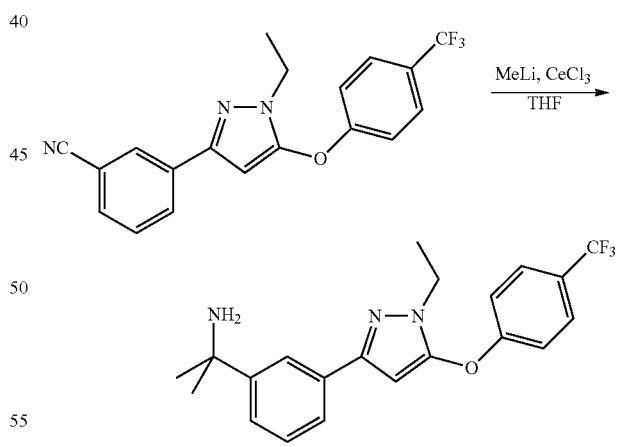

Cerium chloride (16.6 g, 67.2 mmol, 6.00 equiv) was ground to a fine powder with a mortar and pestle, then dried under vacuum (~1 torr) at 150° C. for 1.5 h. After cooling to 22° C., tetrahydrofuran (200 mL) was added. The reaction mixture was cooled to −78° C., and methyllithium (1.60 M in diethyl ether, 42.0 mL, 67.2 mmol, 6.00 equiv) was added. The reaction mixture was stirred at −78° C. for 1 hour, and then a solution of 3-{1-ethyl-5-[4-(trifluoromethyl)phenoxy]-1H-pyrazol-3-yl}benzonitrile (4.00 g, 11.2 mmol, 1 equiv) in tetrahydrofuran (25 mL) was added via cannula.

After stirring for 10 minutes at −78° C., the cooling bath was removed and the reaction mixture was allowed to warm to 22° C. After 60 minutes, saturated aqueous ammonium chloride solution was added, and the product was extracted with ethyl acetate. The organic layer was washed with saturated aqueous sodium chloride solution, and the washed solution was dried over sodium sulfate. The dried solution was filtered, and the filtrate was concentrated to afford 2-(3-{1-ethyl-5-[4-(trifluoromethyl)phenoxy]-1H-pyrazol-3-yl}phenyl)propan-2-amine (4.3 g, 99%). The product was used without further purification. Calcd (M+1)⁺: 390.2. Found: 390.1.

Step 5:

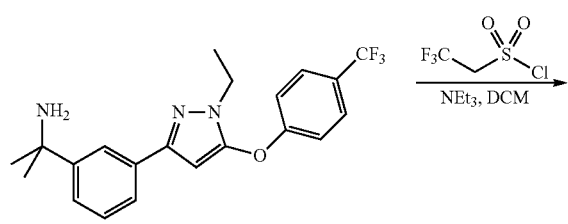

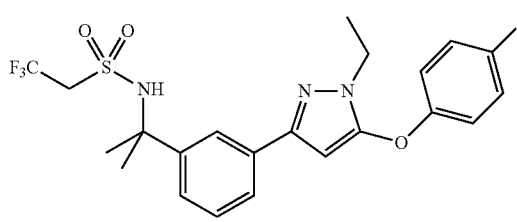

2,2,2-trifluoroethanesulfonyl chloride (0.83 mL, 7.7 mmol, 1.5 equiv) was added to a solution of 2-(3-{1-ethyl-5-[4-(trifluoromethyl)phenoxy]-1H-pyrazol-3-yl}phenyl)propan-2-amine (2.0 g, 5.1 mmol, 1 equiv) and triethylamine (1.1 mL, 7.7 mmol, 1.5 equiv) in dichloromethane (51 mL) at −78° C. The reaction mixture was stirred at −78° C. for 10 minutes, and then the cooling bath was removed. After stirring for 20 minutes, the reaction mixture was partitioned between dichloromethane and citric acid solution (1 M). The organic layer was dried over sodium sulfate. The dried solution was filtered, and the filtrate was concentrated. The residue was purified by flash-column chromatography on silica gel (hexanes, grading to 50% ethyl acetate-hexanes) to afford N-[1-(3-{1-ethyl-5-[4-(trifluoromethyl)phenoxy]-1H-pyrazol-3-yl}phenyl)-1-methylethyl]-2,2,2-trifluoroethanesulfonamide (2.04 g, 74%) as a white solid. Calcd (M+1)⁺: 536.1. Found: 536.1. ¹H NMR (600 MHz, cdcl3) δ 7.92 (s, 1H), 7.70 (d, J=7.3, 1H), 7.65 (d, J=8.7, 2H), 7.48-7.39 (m, 2H), 7.22 (d, J=8.6, 2H), 6.06 (s, 1H), 5.01 (s, 1H), 4.11 (q, J=7.3, 2H), 3.42 (q, J=8.9, 2H), 1.83 (s, 6H), 1.45 (t, J=7.3, 3H).

The following were made by similar procedures, varying the aryl halide used in Step 3 and/or the sulfonyl chloride in Step 5.

| # | Structure | Name | Calc Mass (M + 1)⁺ | Exp Mass (M + 1)⁺ |
|---|---|---|---|---|
| 2 | 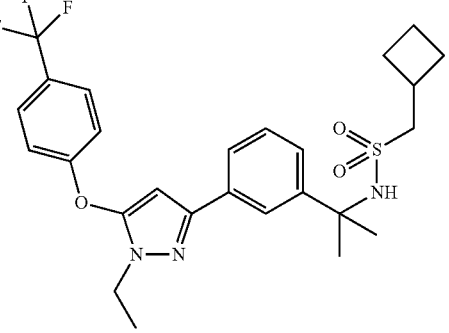 | 1-cyclobutyl-N-[1-(3-{1-ethyl-5-[4-(trifluoromethyl)phenoxy]-1H-pyrazol-3-yl}phenyl)-1-methylethyl]methanesulfonamide | 522.2 | 522.2 |

-continued

| # | Structure | Name | Calc Mass (M + 1)+ | Exp Mass (M + 1)+ |
|---|---|---|---|---|
| 3 | 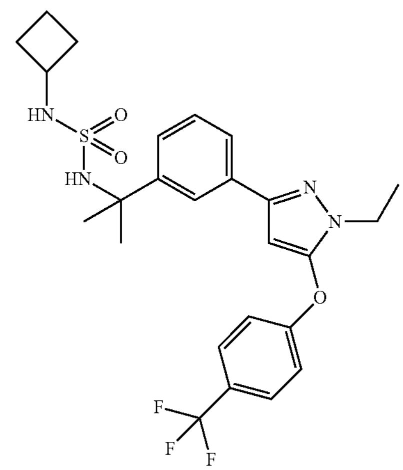 [SMILES: CCn1nc(-c2cccc(C(C)(C)NS(=O)(=O)NC3CCC3)c2)cc1Oc1ccc(C(F)(F)F)cc1] | N-cyclobutyl-N'-[1-(3-{1-ethyl-5-[4-(trifluoromethyl)phenoxy]-1H-pyrazol-3-y}phenyl)-1-methylethyl]sulfamide | 523.2 | 523.1 |
| 4 | 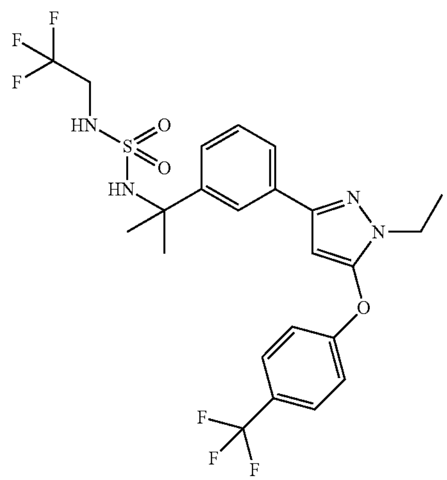 [SMILES: CCn1nc(-c2cccc(C(C)(C)NS(=O)(=O)NCC(F)(F)F)c2)cc1Oc1ccc(C(F)(F)F)cc1] | N-[1-(3-{1-ethyl-5-[4-(trifluoromethyl)phenoxy]-1H-pyrazol-3-yl}phenyl)-1-methylethyl]-N'-(2,2,2-trifluoroethyl)sulfamide | 551.2 | 551.1 |
| 5 | 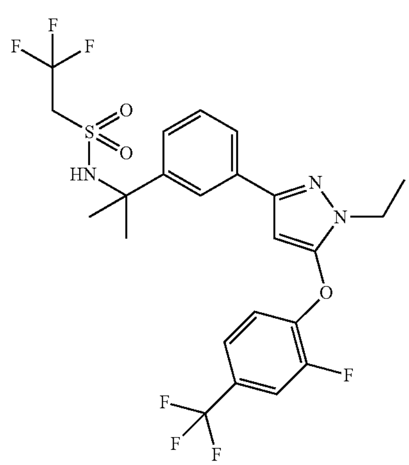 [SMILES: CCn1nc(-c2cccc(C(C)(C)NS(=O)(=O)CC(F)(F)F)c2)cc1Oc1ccc(C(F)(F)F)cc1F] | N-[1-(3-{1-ethyl-5-[2-fluoro-4-(trifluoromethyl)phenoxy]-1H-pyrazol-3-yl}phenyl)-1-methylethyl]-2,2,2-trifluoroethanesulfonamide | 554.1 | 554.1 |

-continued

| # | Structure | Name | Calc Mass (M + 1)+ | Exp Mass (M + 1)+ |
|---|---|---|---|---|
| 6 | 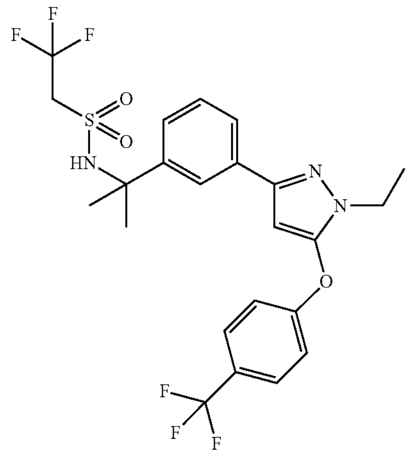 [SMILES: CCn1nc(-c2cccc(C(C)(C)NS(=O)(=O)CC(F)(F)F)c2)cc1Oc1ccc(C(F)(F)F)cc1] | N-[1-(3-{1-ethyl-5-[4-(trifluoromethyl)phenoxy]-1H-pyrazol-3-yl}phenyl)-1-methylethyl]-2,2,2-trifluoroethanesulfonamide | 536.1 | 536.1 |
| 7 | 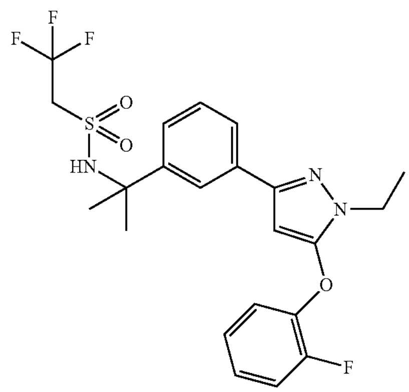 [SMILES: CCn1nc(-c2cccc(C(C)(C)NS(=O)(=O)CC(F)(F)F)c2)cc1Oc1ccccc1F] | N-(1-{3-[1-ethyl-5-(2-fluorophenoxy)-1H-pyrazol-3-yl]phenyl}-1-methylethyl)-2,2,2-trifluoroethanesulfonamide | 486.1 | 486.1 |
| 8 | 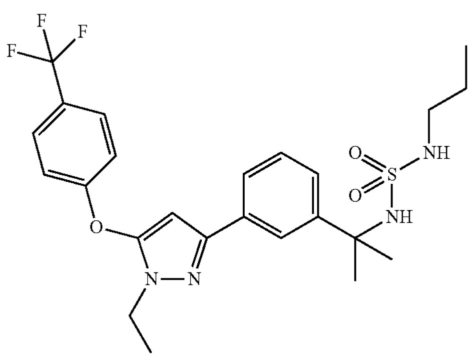 [SMILES: CCCNS(=O)(=O)NC(C)(C)c1cccc(-c2cc(Oc3ccc(C(F)(F)F)cc3)n(CC)n2)c1] | N-[1-(3-{1-ethyl-5-[4-(trifluoromethyl)phenoxy]-1H-pyrazol-3-yl}phenyl)-1-methylethyl]-N'-propylsulfamide | 511.2 | 511.1 |
| 9 | 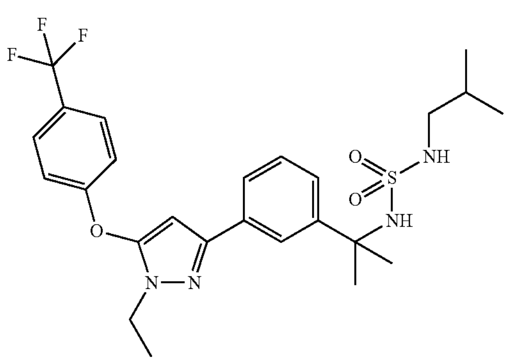 [SMILES: CCn1nc(-c2cccc(C(C)(C)NS(=O)(=O)NCC(C)C)c2)cc1Oc1ccc(C(F)(F)F)cc1] | N-[1-(3-{1-ethyl-5-[4-(trifluoromethyl)phenoxy]-1H-pyrazol-3-yl}phenyl)-1-methylethyl]-N'-isobutylsulfamide | 525.2 | 525.2 |

-continued

| # | Structure | Name | Calc Mass (M + 1)+ | Exp Mass (M + 1)+ |
|---|---|---|---|---|
| 10 | 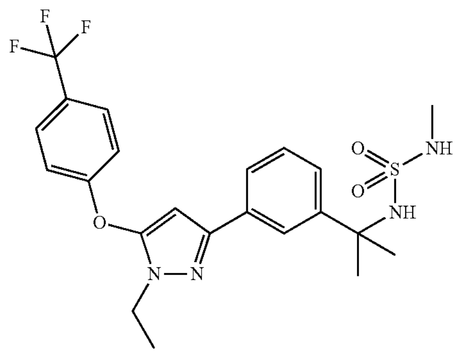 [SMILES: CCn1nc(-c2cccc(C(C)(C)NS(=O)(=O)NC)c2)cc1Oc1ccc(C(F)(F)F)cc1] | N-[1-(3-{1-ethyl-5-[4-(trifluoromethyl)phenoxy]-1H-pyrazol-3-yl}phenyl)-1-methylethyl]-N'-methylsulfamide | 483.2 | 483.1 |
| 11 | 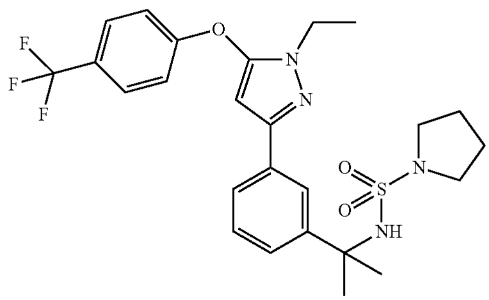 [SMILES: CCn1nc(-c2cccc(C(C)(C)NS(=O)(=O)N3CCCC3)c2)cc1Oc1ccc(C(F)(F)F)cc1] | N-[1-(3-{1-ethyl-5-[4-(trifluoromethyl)phenoxy]-1H-pyrazol-3-yl}phenyl)-1-methylethyl]pyrrolidine-1-sulfonamide | 523.2 | 523.1 |
| 12 | 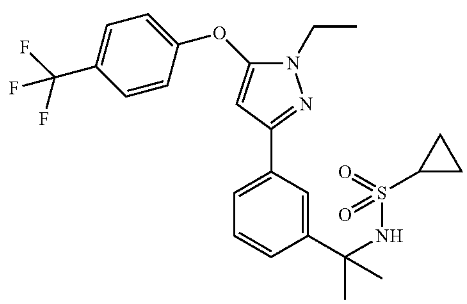 [SMILES: CCn1nc(-c2cccc(C(C)(C)NS(=O)(=O)C3CC3)c2)cc1Oc1ccc(C(F)(F)F)cc1] | N-[1-(3-{1-ethyl-5-[4-(trifluoromethyl)phenoxy]-1H-pyrazol-3-yl}phenyl)-1-methylethyl]cyclopropanesulfonamide | 494.2 | 494.1 |
| 13 | 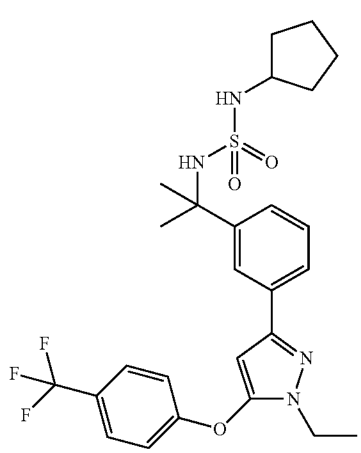 [SMILES: CCn1nc(-c2cccc(C(C)(C)NS(=O)(=O)NC3CCCC3)c2)cc1Oc1ccc(C(F)(F)F)cc1] | N-cyclopentyl-N'-[1-(3-{1-ethyl-5-[4-(trifluoromethyl)phenoxy]-1H-pyrazol-3-yl}phenyl)-1-methylethyl]sulfamide | 537.2 | 537.1 |

-continued

| # | Structure | Name | Calc Mass (M + 1)+ | Exp Mass (M + 1)+ |
|---|---|---|---|---|
| 14 | 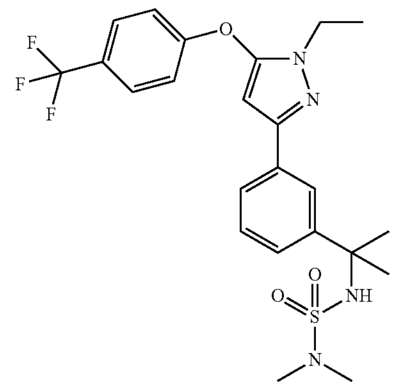 [SMILES: CCn1nc(-c2cccc(C(C)(C)NS(=O)(=O)N(C)C)c2)cc1Oc1ccc(C(F)(F)F)cc1] | N'-[1-(3-{1-ethyl-5-[4-(trifluoromethyl)phenoxy]-1H-pyrazol-3-yl}phenyl)-1-methylethyl]-N,N-dimethylsulfamide | 497.2 | 497.1 |

Example 15

N-[1-(3-{1-ethyl-5-[4-(trifluoromethyl)phenoxy]-1H-pyrazol-3-yl}-5-fluorophenyl)-1-methylethyl]-2,2,2-trifluoraethanesulfonamide

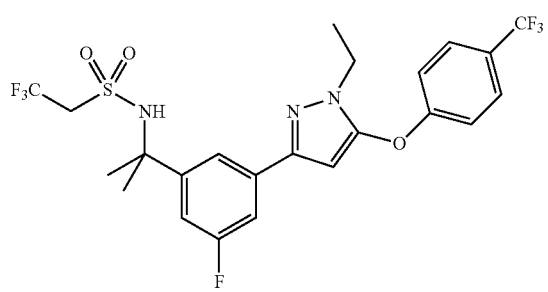 [SMILES: CCn1nc(-c2cc(F)cc(C(C)(C)NS(=O)(=O)CC(F)(F)F)c2)cc1Oc1ccc(C(F)(F)F)cc1]

Step 1:

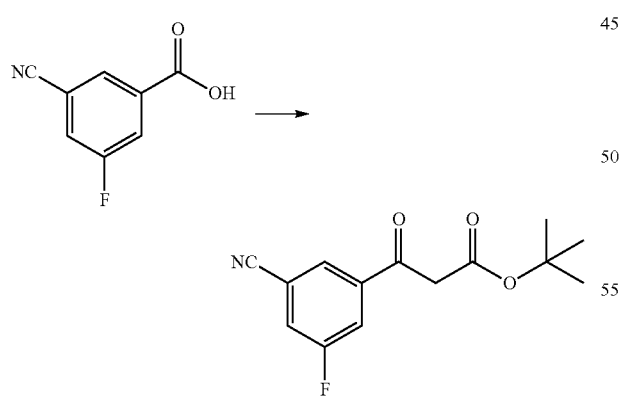

Diisopropylamine (8.6 ml, 60.3 mmol) was dissolved in THF (50 ml) and cooled to 0° C. "Butyllithium (38 ml, 60.8 mmol) was added. The reaction was allowed to stir at 0° C. for twenty minutes. The reaction was further cooled to −78° C. and tert-butyl acetate (8.2 ml, 60.9 mmol), in a solution of THF (25 ml), was slowly added. The reaction was allowed to stir at −78° C. for one hour.

In a separate flask, 3-cyano-5-fluorobenzoic acid (5.02 g, 30.4 mmol), CDI (4.91 g, 30.3 mmol), and THF (50 ml) were combined and allowed to stir at room temperature for about one hour.

The CDI mixture was transferred via canula into the flask containing the cooled enolate mixture. The reaction was allowed to stir at −78° C. for approximately one hour. The reaction was removed from the bath and allowed to stir and warm to room temperature over one hour and twenty-five minutes.

The reaction was cooled slightly, diluted with ethyl acetate, and 2N HCl was added. The layers were separated. The aqueous layer was extracted three times with ethyl acetate. The combined organic extracts were dried over sodium sulfate, filtered, and concentrated. The residue was purified by column chromatography on silica gel, eluting with EtOAc/hexane (0-20% gradient) to yield tert-butyl 3-(3-cyano-5-fluorophenyl)-3-oxopropanoate. Calc'd (M+1): 264. Found: 264.

Step 2:

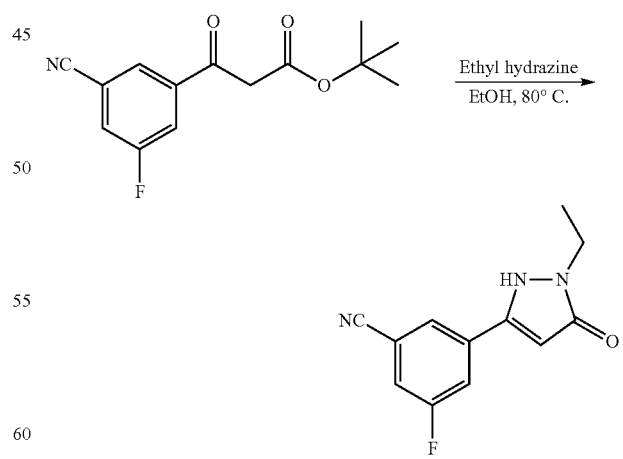

3-(1-ethyl-5-oxo-2,5-dihydro-1H-pyrazol-3-yl)-5-fluorobenzonitrile was prepared from tert-butyl 3-(3-cyano-5-fluorophenyl)-3-oxopropanoate with a procedure similar to that used for Example 1, Step 2. Calc'd (M+1): 232. Found: 232.

Step 3:

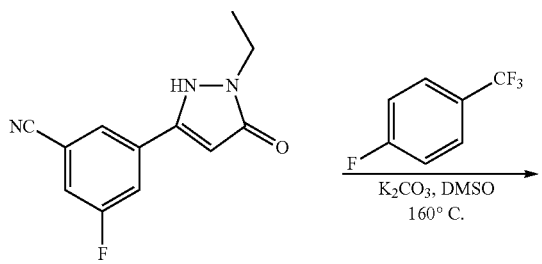

3-{1-ethyl-5-[4-(trifluoromethyl)phenoxy]-1H-pyrazol-3-yl}-5-fluorobenzonitrile was prepared from 3-(1-ethyl-5-oxo-2,5-dihydro-1H-pyrazol-3-yl)-5-fluorobenzonitrile with a procedure similar to that used for Example 1, Step 3. Calc'd (M+1): 376. Found: 376.

Step 4:

2-(3-{1-ethyl-5-[4-(trifluoromethyl)phenoxy]-1H-pyrazol-3-yl}-5-fluorophenyl)propan-2-amine was prepared from -{1-ethyl-5-[4-(trifluoromethyl)phenoxy]-1H-pyrazol-3-yl}-5-fluorobenzonitrile with a procedure similar to that used for Example 1, Step 4 Calc'd (M+1): 408. Found: 408.

Step 5:

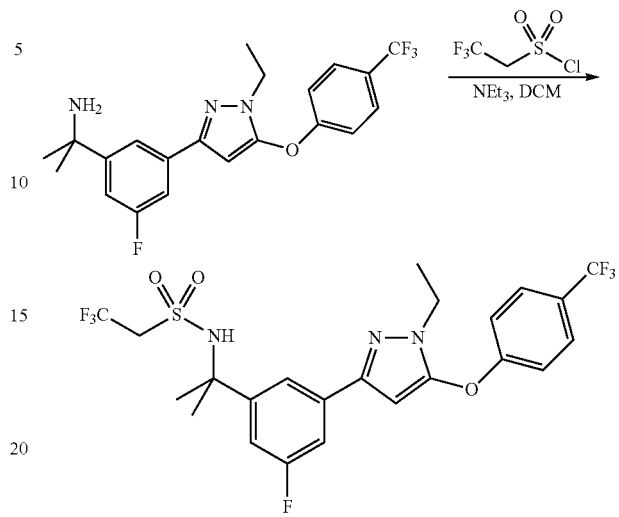

N-[1-(3-{1-ethyl-5-[4-(trifluoromethyl)phenoxy]-1H-pyrazol-3-yl}-5-fluorophenyl)-1-methylethyl]-2,2,2-trifluoroethanesulfonamide was prepared from 2-(3-{1-ethyl-5-[4-(trifluoromethyl)phenoxy]-1H-pyrazol-3-yl}-5-fluorophenyl)propan-2-amine with a procedure similar to that used for Example 1, Step 4 Calc'd (M+1): 554. Found: 554.

Example 16

N-cyclobutyl-N'-[1-(3-{1-ethyl-3-[4-(trifluoromethyl)phenoxy]-1H-pyrazol-5-yl}phenyl)-1-methylethyl]sulfamide

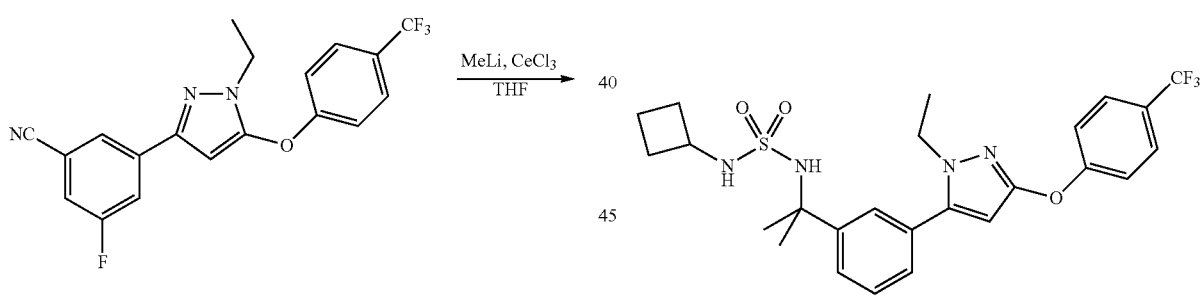

Step 1:

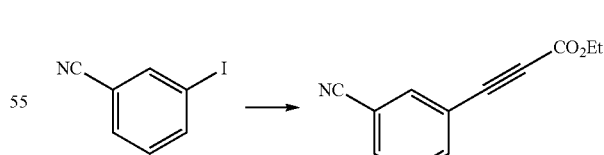

A solution of n-butyllithium (2.50 M in hexanes, 16.8 mL, 41.9 mmol 1.20 equiv) was added dropwise to a solution of ethyl propiolate (4.11 g, 41.9 mmol, 1.20 equiv) in tetrahydrofuran (350 mL) at −78° C. After stirring for 15 minutes at −78° C., a solution of zinc chloride (1.0 M in diethyl ether, 84 mL, 84 mmol, 2.4 equiv) was added and the cooling bath was removed. After stirring for 2 hours, 3-iodobenzonitrile 8.00 g (34.9 mmol, 1 equiv) and Pd(Ph3P)4 (2.0 g, 1.7 mmol, 0.05 equiv) were added and the reaction mixture was heated to 50° C. After stirring for 90 minutes, the reaction mixture was cooled to 22° C. and filtered. The filtrate was concentrated to ~½ volume, then was partitioned between ethyl acetate and water. The organic layer was washed with saturated aqueous sodium chloride solution and dried over sodium sulfate. The dried solution was filtered, and the filtrate was concentrated. The residue was purified by flash-column chromatography on silica gel (hexanes, grading to 50% ethyl acetate-hexanes) to afford ethyl 3-(3-cyanophenyl)prop-2-ynoate (3.55 g, 51%) as a light-orange solid. Calcd (M+1)⁺: 200.1. Found: 200.1.
Step 2:

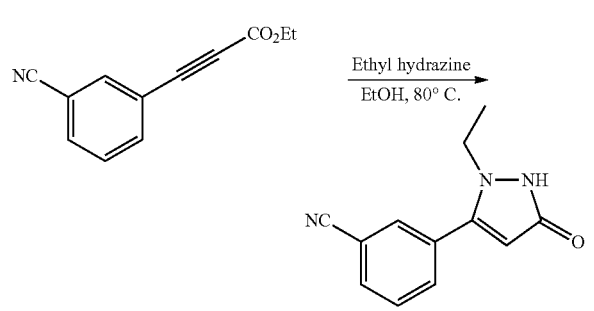

Ethyl hydrazine oxalate (4.01 g, 26.7 mmol, 1.50 equiv) was added to a solution of ethyl 3-(3-cyanophenyl)prop-2-ynoate (3.55 g, 17.8 mmol, 1 equiv) and triethylamine (3.73 mL, 26.7 mmol, 1.50 equiv) in ethanol (180 mL). The reaction mixture was heated to 80° C. for 3.5 hours, then cooled to 22° C. The cooled reaction mixture was concentrated by rotary evaporation, and the residue was partitioned between ethyl acetate and water. The organic layer was washed with saturated aqueous sodium chloride solution, and the washed solution was dried over sodium sulfate. The dried solution was filtered, and the filtrate was concentrated to afford 3-(2-ethyl-5-oxo-2,5-dihydro-1H-pyrazol-3-yl)benzonitrile (3.5 g, 3:1 mixture of regioisomers in favor of desired product). The mixture of regioisomers was used without separating in the next step. Calcd (M+1)⁺: 214.1. Found: 214.1.
Step 3:

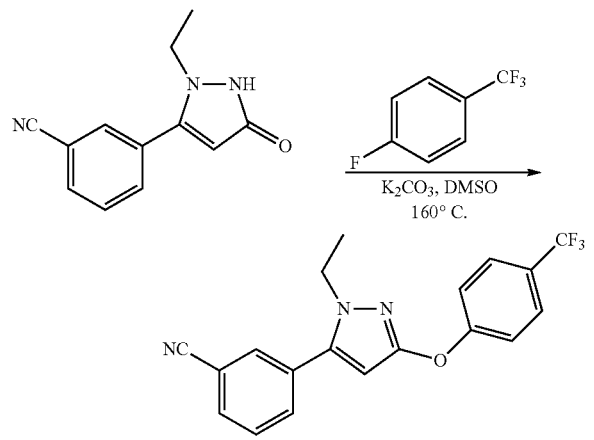

1-fluoro-4-(trifluoromethyl)benzene (2.5 mL, 20 mmol, 6.0 equiv) was added to a mixture of 3-(2-ethyl-5-oxo-2,5-dihydro-1H-pyrazol-3-yl)benzonitrile (688 mg, 3.23 mmol, 1 equiv) and potassium carbonate (1.11 g, 8.07 mmol, 2.50 equiv) in dimethyl sulfoxide (8 mL) in a high pressure reaction vessel. The vessel was sealed, and the reaction mixture was heated to 160° C. After stirring for 4 hours, the high pressure vessel was cooled to 22° C. and the reaction mixture was partitioned between ethyl acetate and water. The organic layer was washed with saturated aqueous sodium chloride solution, and the washed solution was dried over sodium sulfate. The dried solution was filtered, and the filtrate was concentrated. The residue was purified by flash-column chromatography (hexanes, grading to 40% ethyl acetate-hexanes) to afford 3-{1-ethyl-3-[4-(trifluoromethyl)phenoxy]-1H-pyrazol-5-yl}benzonitrile (700 mg, 61%) as a white solid. Calcd (M+1)⁺: 358.1. Found: 358.0.
Step 4:

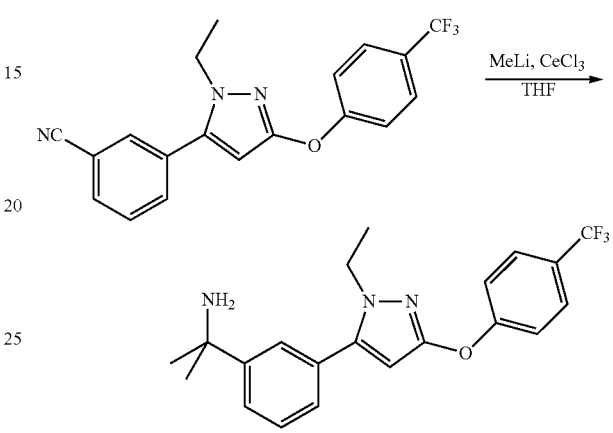

Cerium chloride (2.69 g, 10.9 mmol, 6.00 equiv) was ground to a fine powder with a mortar and pestle, then dried under vacuum (~1 torr) at 150° C. for 1.5 h. After cooling to 22° C., tetrahydrofuran (30 mL) was added. The reaction mixture was cooled to −78° C., and methyllithium (1.60 M in diethyl ether, 6.82 mL, 10.9 mmol, 6.00 equiv) was added. The reaction mixture was stirred at −78° C. for 1 hour, and then a solution of 3-{1-ethyl-3-[4-(trifluoromethyl)phenoxy]-1H-pyrazol-5-yl}benzonitrile (650 mg, 1.82 mmol, 1 equiv) in tetrahydrofuran (6 mL) was added via cannula. After stirring for 10 minutes at −78° C., the cooling bath was removed and the reaction mixture was allowed to warm to 22° C. After 15 minutes, saturated aqueous ammonium chloride solution was added, and the product was extracted with ethyl acetate. The organic layer was washed with saturated aqueous sodium chloride solution, and the washed solution was dried over sodium sulfate. The dried solution was filtered, and the filtrate was concentrated to afford 2-(3-{1-ethyl-3-[4-(trifluoromethyl)phenoxy]-1H-pyrazol-5-yl}phenyl)propan-2-amine (705 mg, 100%). The product was used without further purification. Calcd (M+1)⁺: 390.2. Found: 390.1.
Step 5:

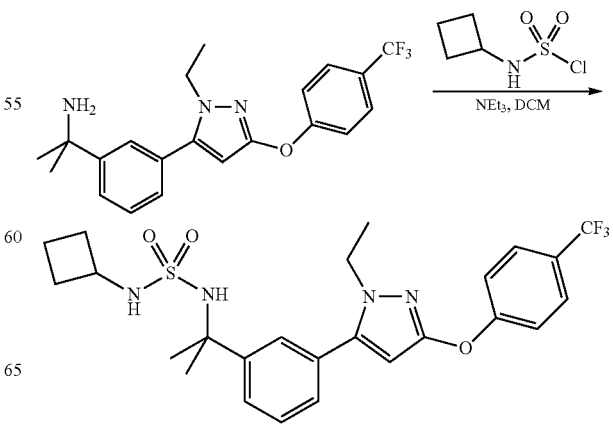

A solution of cyclobutylsulfamoyl chloride (0.65 M in CH₂Cl₂, 3.0 mL, 1.9 mmol, 1.5 equiv) was added to a solution of 2-(3-{1-ethyl-3-[4-(trifluoromethyl)phenoxy]-1H-pyrazol-5-yl}phenyl)propan-2-amine (0.50 g, 1.3 mmol, 1 equiv) and triethylamine (1.1 mL, 7.7 mmol, 6.0 equiv) in dichloromethane at −78° C. The reaction mixture was stirred for 10 minutes at −78° C., then cooling bath was removed. Stirred an additional 20 minutes, then partitioned between dichloromethane and aqueous citric acid solution (1 M). The organic layer was dried over sodium sulfate. The dried solution was filtered, and the filtrate was concentrated. The residue was purified by flash-column chromatography (hexanes, grading to 50% ethyl acetate-hexanes) to afford N-cyclobutyl-N'-[1-(3-{1-ethyl-3-[4-(trifluoromethyl)phenoxy]-1H-pyrazol-5-yl}phenyl)-1-methylethyl]sulfamide (270 mg, 40%) as a white solid. Calcd (M+1)⁺: 523.2. Found: 523.1. ¹H NMR (600 MHz, cdcl3) δ 7.60-7.49 (m, 4H), 7.42 (t, J=7.7, 1H), 7.29 (d, J=7.6, 1H), 7.23 (d, J=8.7, 2H), 5.86 (s, 1H), 4.75 (s, 1H), 4.33 (d, J=8.5, 1H), 4.08 (q, J=7.2, 3H), 2.24 (dd, J=16.8, 7.8, 2H), 1.89-1.80 (m, 3H), 1.72 (s, 6H), 1.70-1.54 (m, 3H), 1.41 (t, J=7.2, 3H).

The following were made by similar procedures, varying the aryl halide used in Step 3 and/or the sulfonyl chloride in Step 5.

| # | Structure | Name | Calc Mass (M + 1)⁺ | Exp Mass (M + 1)⁺ |
|---|---|---|---|---|
| 17 | 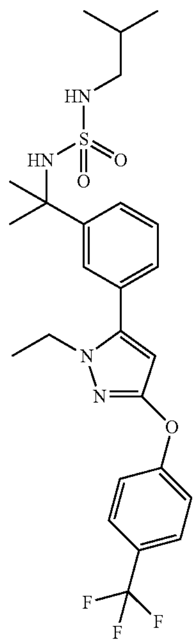 [SMILES: CCn1nc(Oc2ccc(C(F)(F)F)cc2)cc1-c1cccc(C(C)(C)NS(=O)(=O)NCC(C)C)c1] | N-[1-(3-{1-ethyl-3-[4-(trifluoromethyl)phenoxy]-1H-pyrazol-5-yl}phenyl)-1-methylethyl]-N'-isobutylsulfamide | 525.2 | 525.3 |
| 18 | 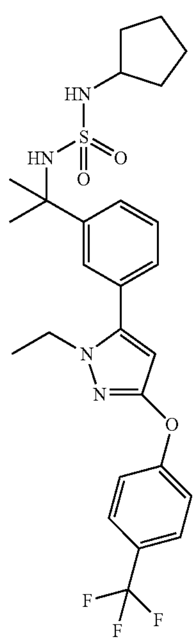 [SMILES: CCn1nc(Oc2ccc(C(F)(F)F)cc2)cc1-c1cccc(C(C)(C)NS(=O)(=O)NC2CCCC2)c1] | N-cyclopentyl-N'-[1-(3-{1-ethyl-3-[4-(trifluoromethyl)phenoxy]-H-pyrazol-5-yl}phenyl)-1-methylethyl]sulfamide | 537.2 | 537.1 |

-continued

| # | Structure | Name | Calc Mass (M + 1)+ | Exp Mass (M + 1)+ |
|---|---|---|---|---|
| 19 | 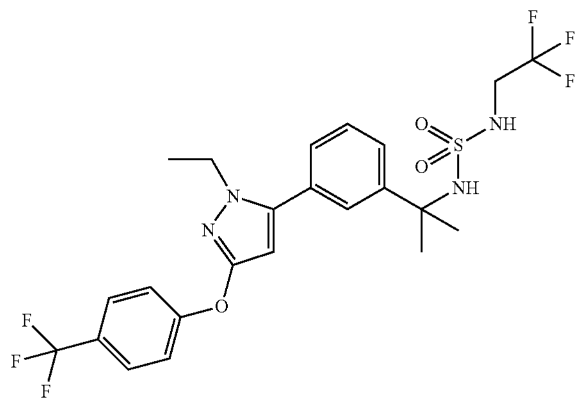 [SMILES: CCn1nc(Oc2ccc(C(F)(F)F)cc2)cc1-c1cccc(C(C)(C)NS(=O)(=O)NCC(F)(F)F)c1] | N-[1-(3-{1-ethyl-3-[4-(trifluoromethyl)phenoxy]-1H-pyrazol-5-yl}phenyl)-1-methylethyl]-N'-(2,2,2-trifluoroethyl)sulfamide | 551.2 | 551.1 |
| 20 | 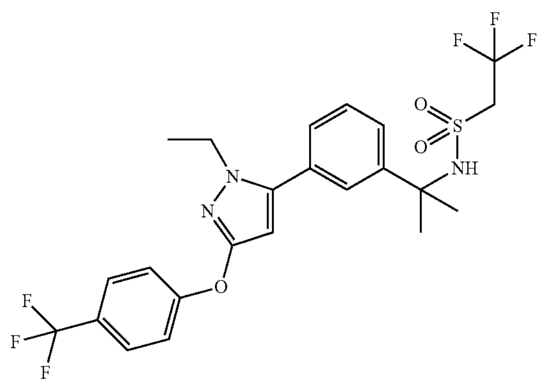 [SMILES: CCn1nc(Oc2ccc(C(F)(F)F)cc2)cc1-c1cccc(C(C)(C)NS(=O)(=O)CC(F)(F)F)c1] | N-[1-(3-{1-ethyl-3-[4-(trifluoromethyl)phenoxy]-1H-pyrazol-5-yl}phenyl)-1-methylethyl]-2,2,2-trifluoroethanesulfonamide | 536.1 | 536.1 |
| 21 | 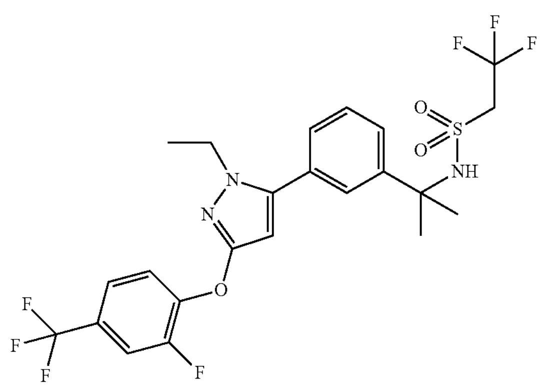 [SMILES: CCn1nc(Oc2ccc(C(F)(F)F)cc2F)cc1-c1cccc(C(C)(C)NS(=O)(=O)CC(F)(F)F)c1] | N-[1-(3-{1-ethyl-3-[2-fluoro-4-(trifluoromethyl)phenoxy]-1H-pyrazol-5-yl}phenyl)-1-methylethyl]-2,2,2-trifluoroethanesulfonamide | 554.1 | 554.1 |
| 22 | 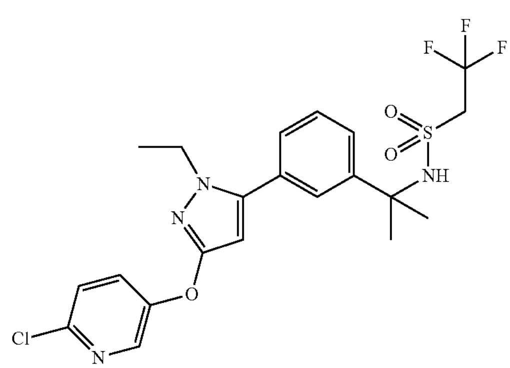 [SMILES: CCn1nc(Oc2ccc(Cl)nc2)cc1-c1cccc(C(C)(C)NS(=O)(=O)CC(F)(F)F)c1] | N-[1-(3-{3-[(6-chloropyridin-3-yl)oxy]-1-ethyl-1H-pyrazol-5-yl}phenyl)-1-methylethyl]-2,2,2-trifluoroethanesulfonamide | 503.1 | 503.1 |

| # | Structure | Name | Calc Mass (M + 1)+ | Exp Mass (M + 1)+ |
|---|---|---|---|---|
| 23 | 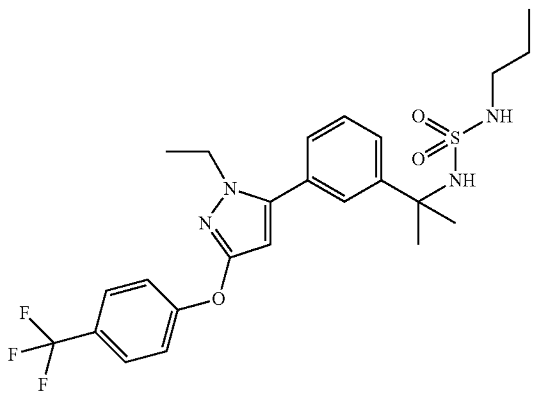 [SMILES: CCCNS(=O)(=O)NC(C)(C)c1cccc(-c2cc(Oc3ccc(C(F)(F)F)cc3)nn2CC)c1] | N-[1-(3-{1-ethyl-3-[4-(trifluoromethyl)phenoxy]-1H-pyrazol-5-yl}phenyl)-1-methylethyl]-N'-propylsulfamide | 511.2 | 510.8 |
| 24 | 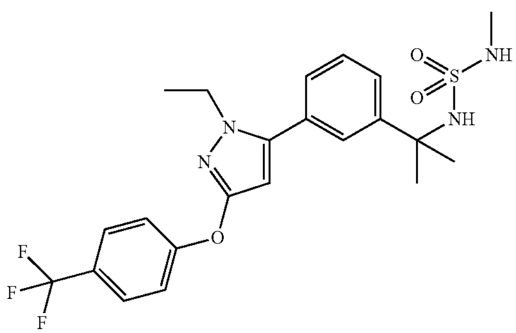 [SMILES: CCn1nc(Oc2ccc(C(F)(F)F)cc2)cc1-c1cccc(C(C)(C)NS(=O)(=O)NC)c1] | N-[1-(3-{1-ethyl-3-[4-(trifluoromethyl)phenoxy]-1H-pyrazol-5-yl}phenyl)-1-methylethyl]-N'-methylsulfamide | 483.2 | 483.0 |
| 25 | 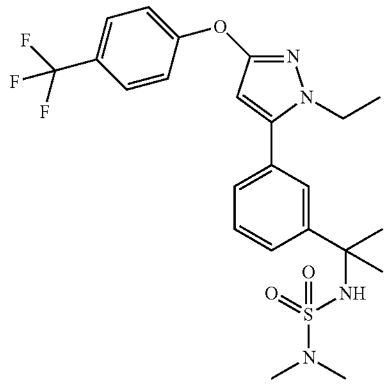 [SMILES: CCn1nc(Oc2ccc(C(F)(F)F)cc2)cc1-c1cccc(C(C)(C)NS(=O)(=O)N(C)C)c1] | N'-[1-(3-{1-ethyl-3-[4-(trifluoromethyl)phenoxy]-1H-pyrazol-5-yl}phenyl)-1-methylethyl]-N,N-dimethylsulfamide | 497.2 | 497.2 |
| 26 | 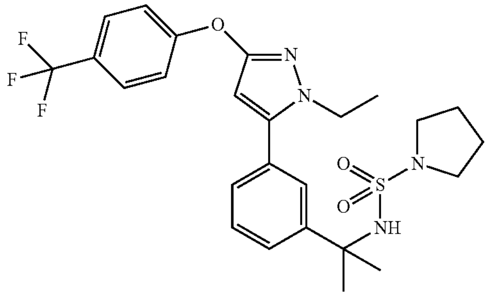 [SMILES: CCn1nc(Oc2ccc(C(F)(F)F)cc2)cc1-c1cccc(C(C)(C)NS(=O)(=O)N2CCCC2)c1] | N-[1-(3-{1-ethyl-3-[4-(trifluoromethyl)phenoxy]-1H-pyrazol-5-yl}phenyl)-1-methylethyl]pyrrolidine-1-sulfonamide | 523.2 | 523.2 |

| # | Structure | Name | Calc Mass (M + 1)+ | Exp Mass (M + 1)+ |
|---|---|---|---|---|
| 27 | 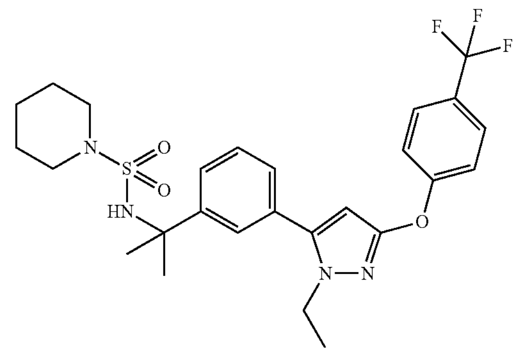 [SMILES: CCn1nc(Oc2ccc(C(F)(F)F)cc2)cc1-c1cccc(C(C)(C)NS(=O)(=O)N2CCCCC2)c1] | N-[1-(3-{1-ethyl-3-[4-(trifluoromethyl)phenoxy]-1H-pyrazol-5-yl}phenyl)-1 methylethyl]piperidine-1-sulfonamide | 537.2 | 537.2 |

Example 28

N-[1-(3-{1-ethyl-5-[4-(trifluoromethyl)phenoxy]-1H-pyrazol-3-yl}phenyl)cyclopropyl]-2,2,2-trifluoroethanesulfonamide Step 1:

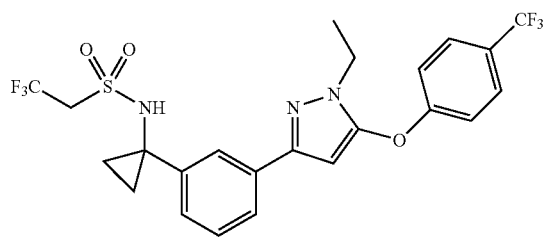 [SMILES: CCn1nc(-c2cccc(C3(NS(=O)(=O)CC(F)(F)F)CC3)c2)cc1Oc1ccc(C(F)(F)F)cc1]

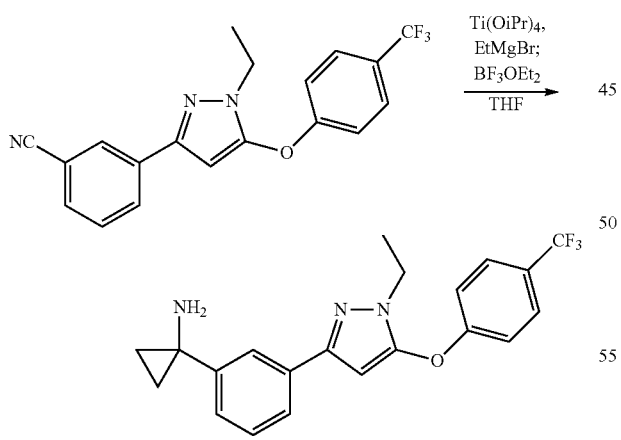

Ethylmagnesium bromide (3.0 M in diethyl ether, 4.3 mL, 13 mmol 2.0 equiv) was added to a solution of titanium (IV) isopropoxide (2.1 mL, 7.1 mmol, 1.1 equiv) and 3-{1-ethyl-5-[4-(trifluoromethyl)phenoxy]-1H-pyrazol-3-yl}benzonitrile (2.3 g, 6.4 mmol, 1 equiv) in tetrahydrofuran (26 mL) at −78° C. The reaction mixture was stirred at −78° C. for 5 min, then the cooling bath was removed. After stirring for an additional 60 minutes, boron trifluoride diethyl etherate (1.6 mL, 13 mmol, 2.0 equiv) was added stirred for 45 minutes, then cooled to 0° C. and treated with aqueous sodium hydroxide solution (3.0 N, 40 mL). The biphasic mixture was stirred for 15 minutes, then filtered through celite with the aid of ethyl acetate. The filtrate was partitioned between ethyl acetate and saturated aqueous sodium chloride solution. The organic layer was dried over sodium sulfate. The dried solution was filtered, and the filtrate was concentrated. The residue was purified by flash-column chromatography (50% ethyl acetate-hexanes, followed by 10% methanol-dichloromethane) to afford 1-(3-{1-ethyl-5-[4-(trifluoromethyl)phenoxy]-1H-pyrazol-3-yl}phenyl)cyclopropanamine (1.35 g, 51%). Calcd (M+1)+: 388.2. Found: 388.1.

Step 2:

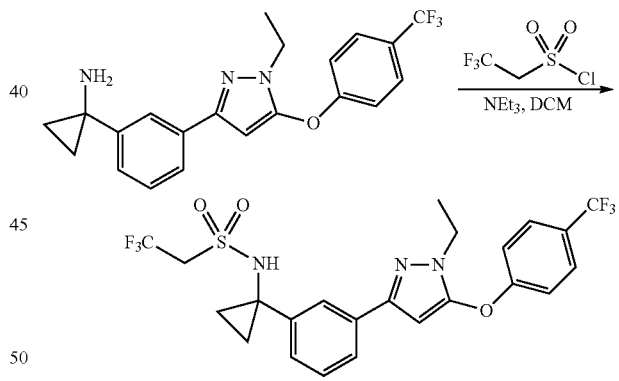

N-[1-(3-{1-ethyl-5-[4-(trifluoromethyl)phenoxy]-1H-pyrazol-3-yl}phenyl)cyclopropyl]-2,2,2-trifluoroethanesulfonamide was made from 1-(3-{1-ethyl-5-[4-(trifluoromethyl)phenoxy]-1H-pyrazol-3-yl}phenyl)cyclopropanamine with a procedure similar to that reported for Example 1, Step 5. Calcd (M+1)+: 534.1. Found: 534.0. $^1$H NMR (600 MHz, cdcl3) δ 7.85 (s, 1H), 7.70 (dd, J=6.9, 1.9, 1H), 7.66 (d, J=8.6, 2H), 7.44-7.37 (m, 2H), 7.23 (d, J=8.6, 2H), 6.05 (s, 1H), 5.56 (s, 1H), 4.12 (q, J=7.3, 2H), 3.25 (q, J=8.9, 2H), 1.48-1.41 (m, 6H), 1.32-1.23 (m, 2H).

The following compounds were made by similar procedures, varying either the aromatic nitrile and/or the sulfonyl chloride used.

| # | Structure | Name | Calc Mass (M + 1)+ | Exp Mass (M + 1)+ |
|---|---|---|---|---|
| 29 | 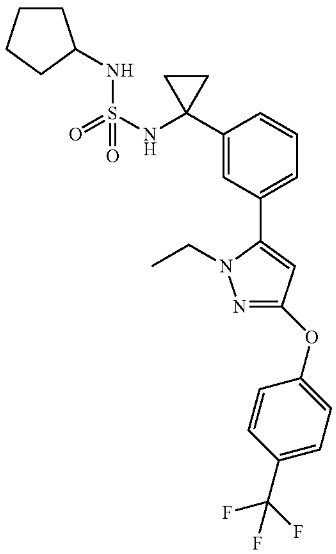 [SMILES: CCn1nc(Oc2ccc(C(F)(F)F)cc2)cc1-c1cccc(C2(NS(=O)(=O)NC3CCCC3)CC2)c1] | N-cyclopentyl-N'-[1-(3-{1-ethyl-3-[4-(trifluoromethyl)phenoxy]-1H-pyrazol-5-yl}phenyl)cyclopropyl]sulfamide | 535.2 | 535.1 |
| 30 | 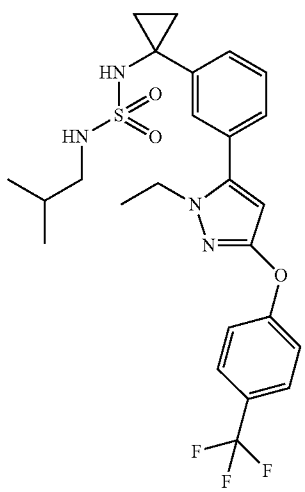 [SMILES: CCn1nc(Oc2ccc(C(F)(F)F)cc2)cc1-c1cccc(C2(NS(=O)(=O)NCC(C)C)CC2)c1] | N-[1-(3-{1-ethyl-3-[4-(trifluoromethyl)phenoxy]-1H-pyrazol-5-yl}phenyl)cyclopropyl]-N'-isobutylsulfamide | 523.2 | 523.2 |
| 31 | 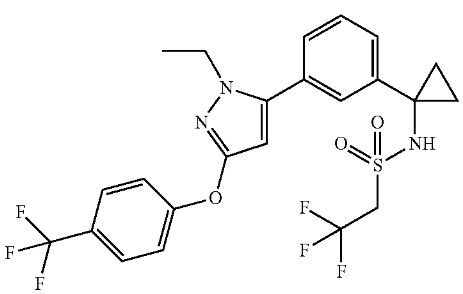 [SMILES: CCn1nc(Oc2ccc(C(F)(F)F)cc2)cc1-c1cccc(C2(NS(=O)(=O)CC(F)(F)F)CC2)c1] | N-[1-(3-{1-ethyl-3-[4-(trifluoromethyl)phenoxy]-1H-pyrazol-5-yl}phenyl)cyclopropyl]-2,2,2-trifluoroethanesulfonamide | 534.1 | 534.0 |
| 32 | 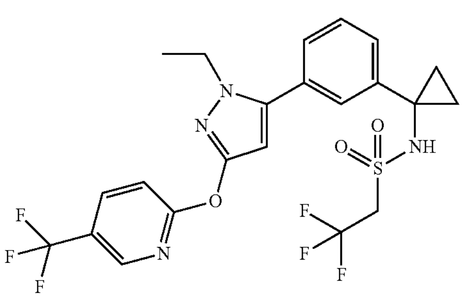 [SMILES: CCn1nc(Oc2ccc(C(F)(F)F)cn2)cc1-c1cccc(C2(NS(=O)(=O)CC(F)(F)F)CC2)c1] | N-{1-[3-(1-ethyl-3-{[5-(trifluoromethyl)pyridin-2-yl]oxy}-1H-pyrazol-5-yl)phenyl]cyclopropyl}-2,2,2-trifluoroethanesulfonamide | 535.1 | 535.1 |

-continued

| # | Structure | Name | Calc Mass (M + 1)+ | Exp Mass (M + 1)+ |
|---|-----------|------|--------------------|--------------------|
| 33 | 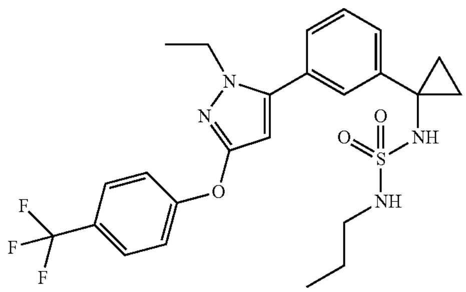 [SMILES: CCCNS(=O)(=O)NC1(c2cccc(-c3cc(Oc4ccc(C(F)(F)F)cc4)nn3CC)c2)CC1] | N-[1-(3-{1-ethyl-3-[4-(trifluoromethyl)phenoxy]-1H-pyrazol-5-yl}phenyl)cyclopropyl]-N'-propylsulfamide | 509.2 | 509.1 |
| 34 | 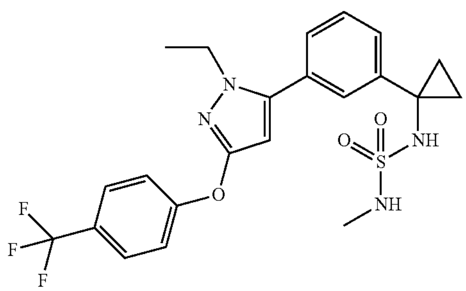 [SMILES: CCn1nc(Oc2ccc(C(F)(F)F)cc2)cc1-c1cccc(C2(NS(=O)(=O)NC)CC2)c1] | N-[1-(3-{1-ethyl-3-[4-(trifluoromethyl)phenoxy]-1H-pyrazol-5-yl}phenyl)cyclopropyl]-N'-methylsulfamide | 481.2 | 481.0 |
| 35 | 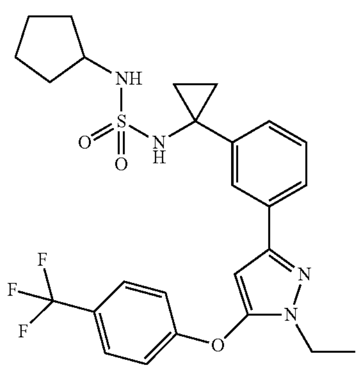 [SMILES: CCn1nc(-c2cccc(C3(NS(=O)(=O)NC4CCCC4)CC3)c2)cc1Oc1ccc(C(F)(F)F)cc1] | N-cyclopentyl-N'-[1-(3-{1-ethyl-5-[4-(trifluoromethyl)phenoxy]-1H-pyrazol-3-yl}phenyl)cyclopropyl]sulfamide | 535.2 | 535.1 |
| 36 | 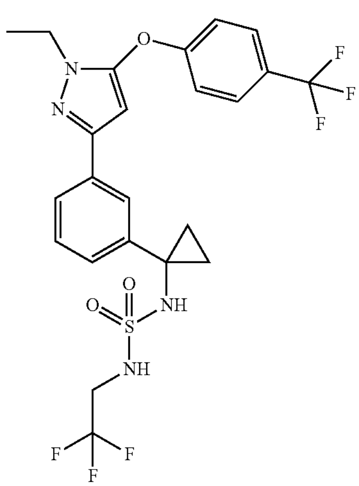 [SMILES: CCn1nc(-c2cccc(C3(NS(=O)(=O)NCC(F)(F)F)CC3)c2)cc1Oc1ccc(C(F)(F)F)cc1] | N-[1-(3-{1-ethyl-5-[4-(trifluoromethyl)phenoxy]-1H-pyrazol-3-yl}phenyl)cyclopropyl]-N'-(2,2,2-trifluoroethyl)sulfamide | 549.1 | 549.1 |

| # | Structure | Name | Calc Mass (M + 1)+ | Exp Mass (M + 1)+ |
|---|---|---|---|---|
| 37 | 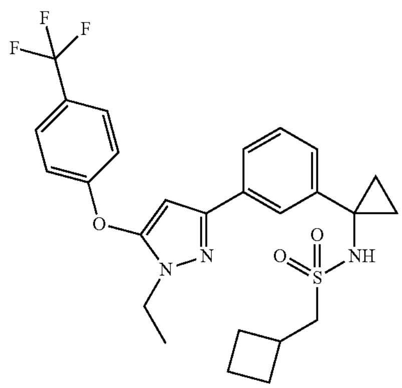 [SMILES: CCn1nc(-c2cccc(C3(NS(=O)(=O)CC4CCC4)CC3)c2)cc1Oc1ccc(C(F)(F)F)cc1] | 1-cyclobutyl-N-[1-(3-{1-ethyl-5-[4-(trifluoromethyl)phenoxy]-1H-pyrazol-3-yl}phenyl)cyclopropyl]methanesulfonamide | 520.2 | 520.1 |
| 38 | 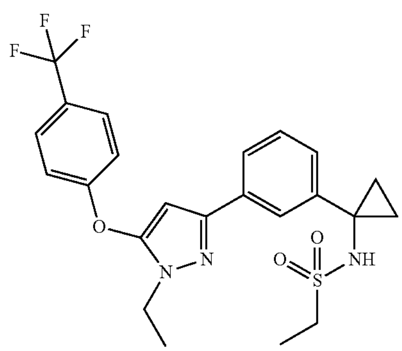 [SMILES: CCn1nc(-c2cccc(C3(NS(=O)(=O)CC)CC3)c2)cc1Oc1ccc(C(F)(F)F)cc1] | N-[1-(3-{1-ethyl-5-[4-(trifluoromethyl)phenoxy]-1H-pyrazol-3-yl}phenyl)cyclopropyl]ethanesulfonamide | 480.2 | 480.1 |
| 39 | 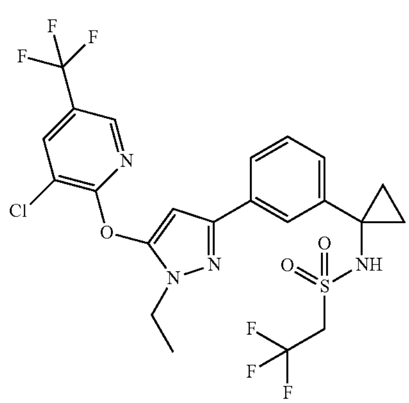 [SMILES: CCn1nc(-c2cccc(C3(NS(=O)(=O)CC(F)(F)F)CC3)c2)cc1Oc1ncc(C(F)(F)F)cc1Cl] | N-{1-[3-(5-{[3-chloro-5-(trifluoromethyl)pyridin-2-yl]oxy}-1-ethyl-1H-pyrazol-3-yl)phenyl]cyclopropyl}-2,2,2-trifluoroethanesulfonamide | 569.1 | 569.0 |
| 40 | 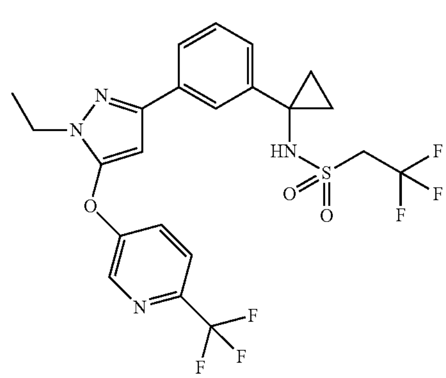 [SMILES: CCn1nc(-c2cccc(C3(NS(=O)(=O)CC(F)(F)F)CC3)c2)cc1Oc1ccc(C(F)(F)F)nc1] | N-{1-[3-(1-ethyl-5-{[6-(trifluoromethyl)pyridin-3-yl]oxy}-1H-pyrazol-3-yl)phenyl]cyclopropyl}-2,2,2-trifluoroethanesulfonamide | 535.1 | 535.0 |

-continued

| # | Structure | Name | Calc Mass (M + 1)+ | Exp Mass (M + 1)+ |
|---|---|---|---|---|
| 41 | 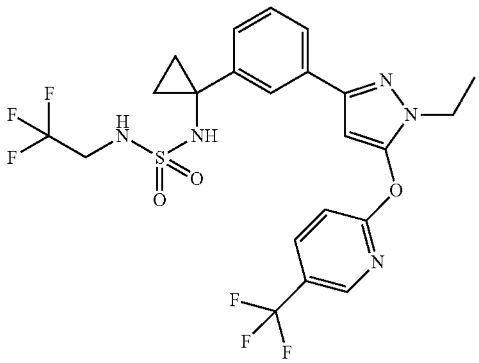 [SMILES: CCn1nc(-c2cccc(C3(NS(=O)(=O)NCC(F)(F)F)CC3)c2)cc1Oc1ccc(C(F)(F)F)cn1] | N-{1-[3-(1-ethyl-5-{[5-(trifluoromethyl)pyridin-2-yl]oxy}-1H-pyrazol-3-yl)phenyl]cyclopropyl}-N'-(2,2,2-trifluoroethyl)sulfamide | 550.1 | 550.0 |
| 42 | 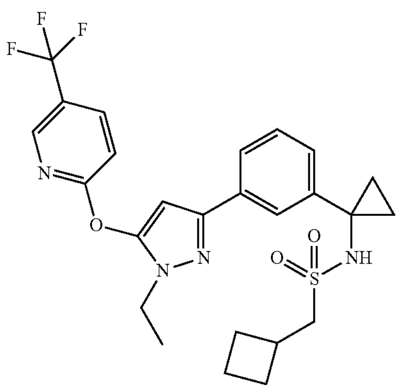 [SMILES: CCn1nc(-c2cccc(C3(NS(=O)(=O)CC4CCC4)CC3)c2)cc1Oc1ccc(C(F)(F)F)cn1] | 1-cyclobutyl-N-{1-[3-(1-ethyl-5-{[5-(trifluoromethyl)pyridin-2-yl]oxy}-1H-pyrazol-3-yl)phenyl]cyclopropyl}methanesulfonamide | 521.2 | 521.1 |
| 43 | 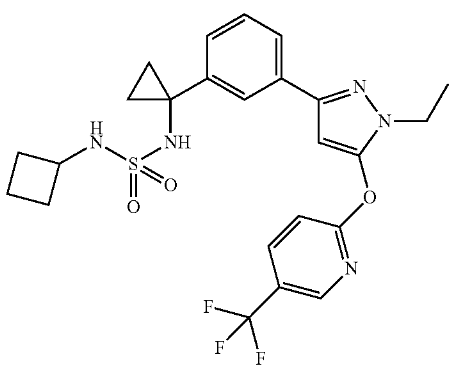 [SMILES: CCn1nc(-c2cccc(C3(NS(=O)(=O)NC4CCC4)CC3)c2)cc1Oc1ccc(C(F)(F)F)cn1] | N-cyclobutyl-N'-{1-[3-(1-ethyl-5-{[5-(trifluoromethyl)pyridin-2-yl]oxy}-1H-pyrazol-3-yl)phenyl]cyclopropyl}sulfamide | 522.2 | 522.1 |
| 44 | 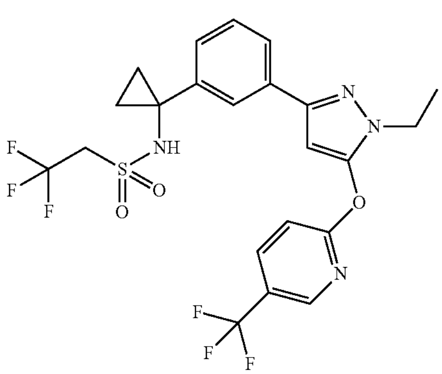 [SMILES: CCn1nc(-c2cccc(C3(NS(=O)(=O)CC(F)(F)F)CC3)c2)cc1Oc1ccc(C(F)(F)F)cn1] | N-{1-[3-(1-ethyl-5-{[5-(trifluoromethyl)pyridin-2-yl]oxy}-1H-pyrazol-3-yl)phenyl]cyclopropyl}-2,2,2-trifluoroethanesulfonamide | 535.1 | 535.0 |

-continued

| # | Structure | Name | Calc Mass (M + 1)+ | Exp Mass (M + 1)+ |
|---|---|---|---|---|
| 45 | 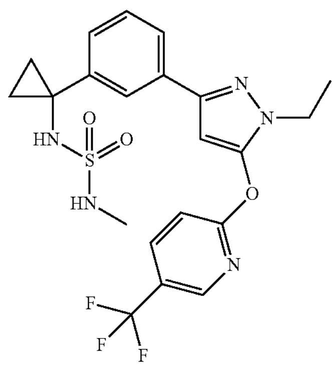 [SMILES: CCn1nc(-c2cccc(C3(NS(=O)(=O)NC)CC3)c2)cc1Oc1ccc(C(F)(F)F)cn1] | N-{1-[3-(1-ethyl-5-{[5-(trifluoromethyl)pyridin-2-yl]oxy}-1H-pyrazol-3-yl)phenyl]cyclopropyl}-N'-methylsulfamide | 482.1 | 482.1 |
| 46 | 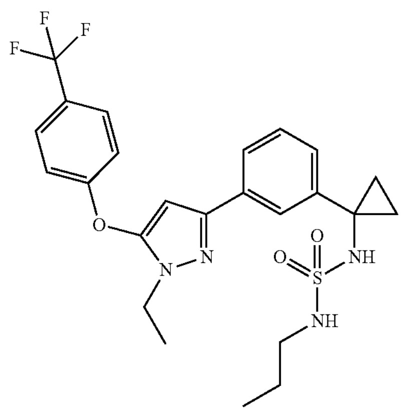 [SMILES: CCCNS(=O)(=O)NC1(c2cccc(-c3cc(Oc4ccc(C(F)(F)F)cc4)n(CC)n3)c2)CC1] | N-[1-(3-{1-ethyl-5-[4-(trifluoromethyl)phenoxy]-1H-pyrazol-3-yl}phenyl)cyclopropyl]-N'-propylsulfamide | 509.2 | 508.9 |
| 47 | 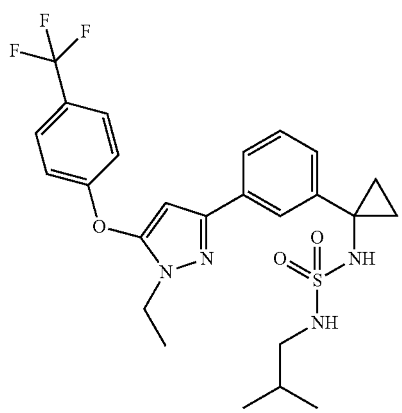 [SMILES: CCn1nc(-c2cccc(C3(NS(=O)(=O)NCC(C)C)CC3)c2)cc1Oc1ccc(C(F)(F)F)cc1] | N-[1-(3-{1-ethyl-5-[4-(trifluoromethyl)phenoxy]-1H-pyrazol-3-yl}phenyl)cyclopropyl]-N'-isobutylsulfamide | 523.2 | 523.1 |
| 48 | 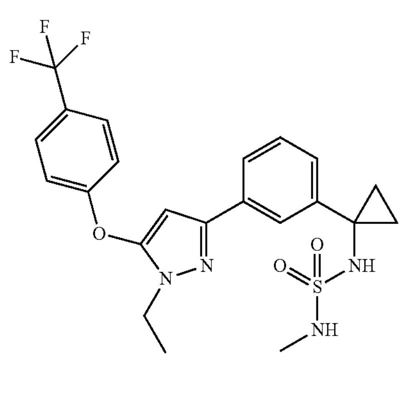 [SMILES: CCn1nc(-c2cccc(C3(NS(=O)(=O)NC)CC3)c2)cc1Oc1ccc(C(F)(F)F)cc1] | N-[1-(3-{1-ethyl-5-[4-(trifluoromethyl)phenoxy]-1H-pyrazol-3-yl}phenyl)cyclopropyl]-N'-methylsulfamide | 481.2 | 481.0 |

-continued

| # | Structure | Name | Calc Mass (M + 1)+ | Exp Mass (M + 1)+ |
|---|---|---|---|---|
| 49 | 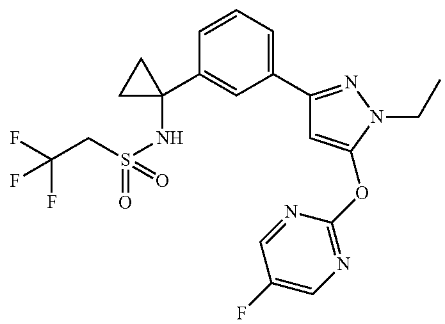 [SMILES: CCn1nc(-c2cccc(C3(NS(=O)(=O)CC(F)(F)F)CC3)c2)cc1Oc1ncc(F)cn1] | N-[1-(3-{1-ethyl-5-[(5-fluoropyrimidin-2-yl)oxy]-1H-pyrazol-3-yl}phenyl)cyclopropyl]-2,2,2-trifluoroethanesulfonamide | 486.1 | 486.0 |
| 50 | 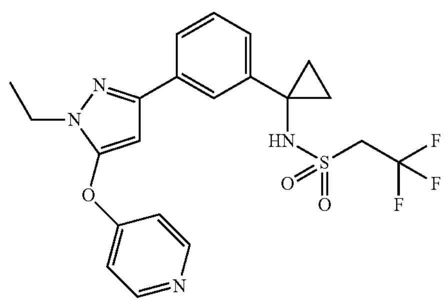 [SMILES: CCn1nc(-c2cccc(C3(NS(=O)(=O)CC(F)(F)F)CC3)c2)cc1Oc1ccncc1] | N-(1-{3-[1-ethyl-5-(pyridin-4-yloxy)-1H-pyrazol-3-yl]phenyl}cyclopropyl)-2,2,2-trifluoroethanesulfonamide | 467.1 | 467.0 |
| 51 | 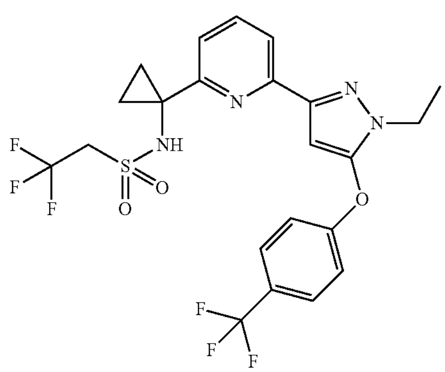 [SMILES: CCn1nc(-c2cccc(C3(NS(=O)(=O)CC(F)(F)F)CC3)n2)cc1Oc1ccc(C(F)(F)F)cc1] | N-[1-(6-{1-ethyl-5-[4-(trifluoromethyl)phenoxy]-1H-pyrazol-3-yl}pyridin-2-yl)cyclopropyl]-2,2,2-trifluoroethanesulfonamide | 535.1 | 535.1 |
| 52 | 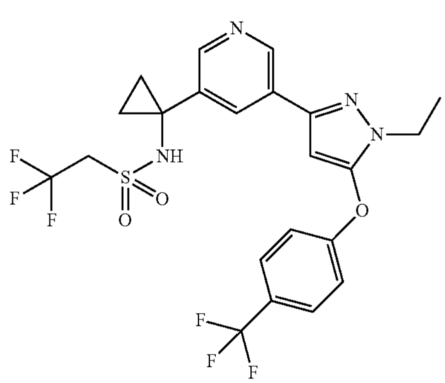 [SMILES: CCn1nc(-c2cncc(C3(NS(=O)(=O)CC(F)(F)F)CC3)c2)cc1Oc1ccc(C(F)(F)F)cc1] | N-[1-(5-{1-ethyl-5-[4-(trifluoromethyl)phenoxy]-1H-pyrazol-3-yl}pyridin-3-yl)cyclopropyl]-2,2,2-trifluoroethanesulfonamide | 535.1 | 535.0 |

Example 53

N-(1-{3-[1-ethyl-3-(4-fluorophenoxy)-1H-pyrazol-5-yl]phenyl}-1-methylethyl)-2,2,2-trifluoroethanesulfonamide

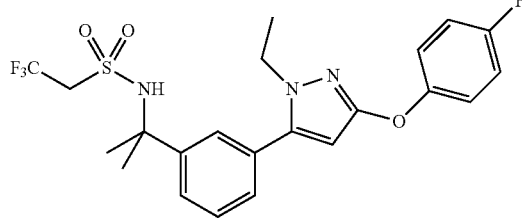

Step 1:

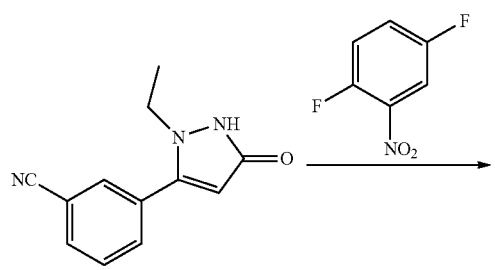

1,4-difluoro-2-nitrobenzene (0.63 mL, 5.9 mmol, 2.5 equiv) was added to a mixture of 3-(2-ethyl-5-oxo-2,5-dihydro-1H-pyrazol-3-yl)benzonitrile (500 mg, 2.3 mmol, 1 equiv) and potassium carbonate (970 mg, 7.0 mmol, 3.0 equiv) in dimethyl sulfoxide (5.9 mL). The reaction mixture was heated to 80° C. for 20 minutes, then cooled to 22° C. The crude reaction mixture was partitioned between ethyl acetate and water. The organic layer was washed with saturated aqueous sodium chloride solution, and the washed solution was dried over sodium sulfate. The dried solution was filtered, and the filtrate was concentrated. The residue was purified by flash-column chromatography on silica gel (hexanes, grading to 50% ethyl acetate-hexanes) to afford 3-[1-ethyl-3-(4-fluoro-2-nitrophenoxy)-1H-pyrazol-5-yl]benzonitrile as light-yellow solid (328 mg, 40%). Calcd (M+1)$^+$: 353.1. Found: 353.0.

Step 2:

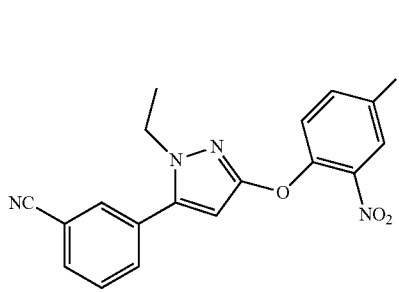

Platinum (3% on carbon, poisoned with 0.6% vanadium, 24 mg, 3.8 mmol, 0.005 equiv) was added to a solution of 3-[1-ethyl-3-(4-fluoro-2-nitrophenoxy)-1H-pyrazol-5-yl]benzonitrile (266 mg, 0.755 mmol, 1 equiv) in methanol (7.6 mL). The reaction flask was capped with a three way valve attached to a vacuum line and a hydrogen balloon. The reaction flask was alternately evacuated and charged with hydrogen for 3 cycles, and finally left under an atmosphere of hydrogen at 22° C. The reaction mixture was stirred for 40 minutes, then filtered through celite with the aid of methanol. Concentrated to afford 3-[3-(2-amino-4-fluorophenoxy)-1-ethyl-1H-pyrazol-5-yl]benzonitrile (243 mg, 90% pure) as a light-yellow solid. Calcd (M+1)$^+$: 323.1. Found: 323.0.

Step 3:

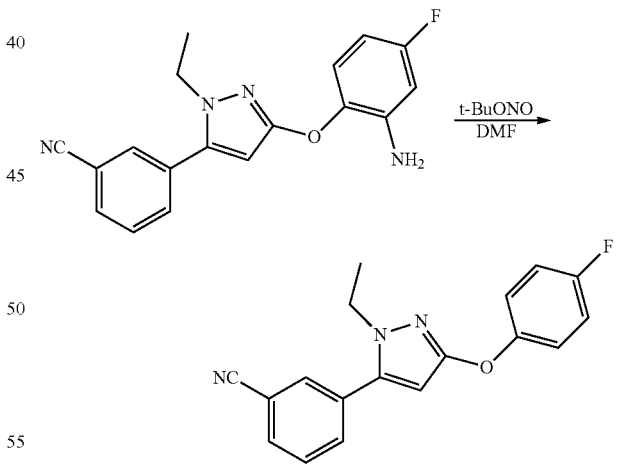

A solution of 3-[3-(2-amino-4-fluorophenoxy)-1-ethyl-1H-pyrazol-5-yl]benzonitrile (262 mg, 0.813 mmol, 1 equiv) in N,N-dimethylformamide (2 mL) was added dropwise over 5 minutes to a solution of t-butylnitrite (0.15 mL, 1.2 mmol, 1.5 equiv) in N,N-dimethylformamide (2.5 mL) at 60° C. The reaction mixture was stirred at 60° C. for 20 minutes, then was partitioned between ethyl acetate and aqueous hydrochloric acid solution (1 M). The organic layer was washed sequentially with an additional portion of aqueous hydrochloric acid solution (1 M) and saturated aqueous sodium chloride solution. The washed organic layer was dried over sodium sulfate, and the dried solution was filtered. The filtrate was concentrated, and the residue was purified by flash-column chromatography on silica gel (hexanes, grading to 50% ethyl acetate-hexanes) to afford 3-[1-ethyl-3-(4-fluorophenoxy)-1H-pyrazol-5-yl]benzonitrile (127 mg, 51%) as a white solid. Calcd (M+1)⁺: 308.1. Found: 308.0.

Step 4:

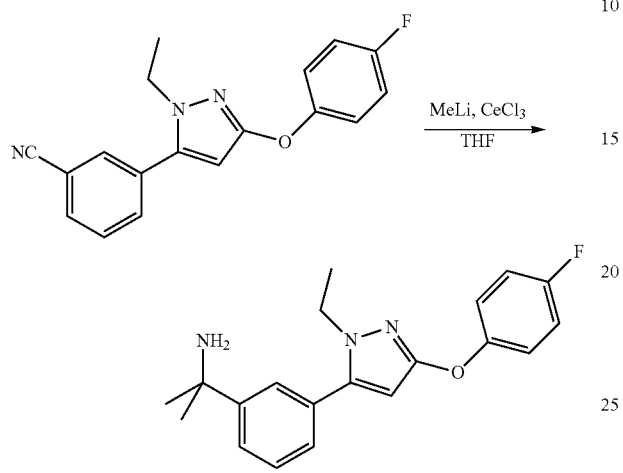

2-{3-[1-ethyl-3-(4-fluorophenoxy)-1H-pyrazol-5-yl]phenyl}propan-2-amine was prepared from 3-[1-ethyl-3-(4-fluorophenoxy)-1H-pyrazol-5-yl]benzonitrile with a procedure similar to that described in Example 1, Step 4. Calcd (M+1)⁺: 340.2. Found: 340.1.

Step 5:

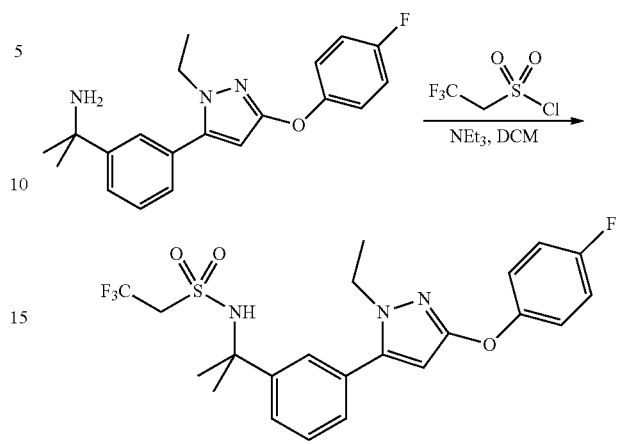

N-(1-{3-[1-ethyl-3-(4-fluorophenoxy)-1H-pyrazol-5-yl]phenyl}-1-methylethyl)-2,2,2-trifluoroethanesulfonamide was prepared from 2-{3-[1-ethyl-3-(4-fluorophenoxy)-1H-pyrazol-5-yl]phenyl}propan-2-amine with a procedure similar to that described in Example 1, Step 5. Calcd (M+1)⁺: 486.1. Found: 486.0.

The following examples were prepared from 2-{3-[1-ethyl-3-(4-fluorophenoxy)-1H-pyrazol-5-yl]phenyl}propan-2-amine with a procedure similar to that described above, substituting sulfamoyl chlorides for 2,2,2-trifluoroethanesulfonyl chloride in Step 5.

| # | Structure | Name | Calc Mass (M + 1)⁺ | Exp Mass (M + 1)⁺ |
|---|-----------|------|--------------------|--------------------|
| 54 | 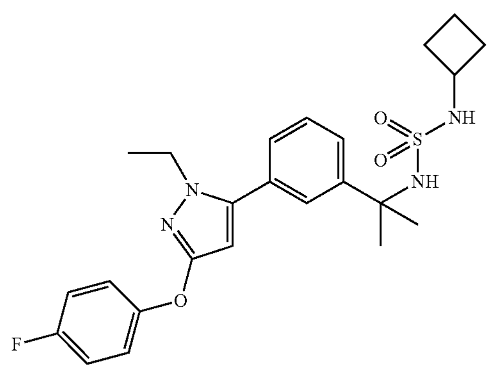 [SMILES: CCn1nc(Oc2ccc(F)cc2)cc1-c1cccc(C(C)(C)NS(=O)(=O)NC2CCC2)c1] | N-cyclobutyl-N'-(1-{3-[1-ethyl-3-(4-fluorophenoxy)-1H-pyrazol-5-yl]phenyl}-1-methylethyl)sulfamide | 473.2 | 473.1 |
| 55 | 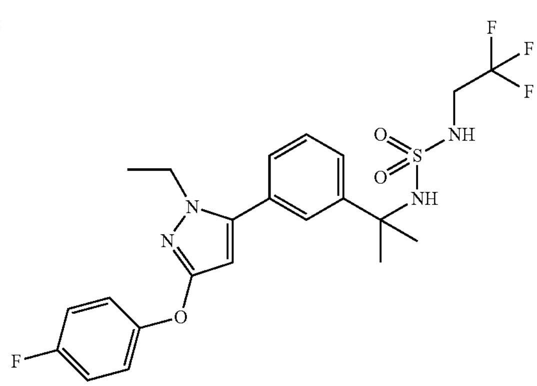 [SMILES: CCn1nc(Oc2ccc(F)cc2)cc1-c1cccc(C(C)(C)NS(=O)(=O)NCC(F)(F)F)c1] | N-(1-{3-[1-ethyl-3-(4-fluorophenoxy)-1H-pyrazol-5-yl]phenyl}-1-methylethyl)-N'-(2,2,2-trifluoroethyl)sulfamide | 501.2 | 501.1 |

Example 56

N-(1-{3-[1-ethyl-5-(4-fluorophenoxy)-1H-pyrazol-3-yl]phenyl}-1-methylethyl)-2,2,2-trifluoroethanesulfonamide

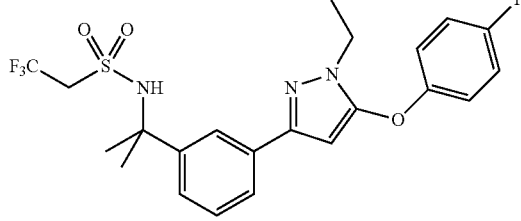

Step 1:

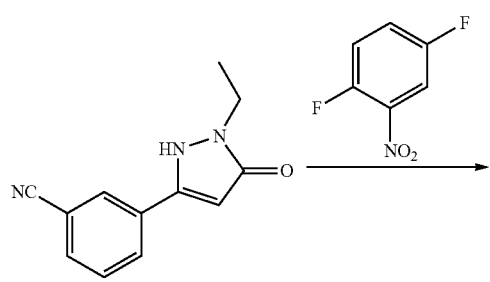

1,4-difluoro-2-nitrobenzene (2.06 g, 9.85 mmol, 3 equiv) was added to a stirring mixture of 3-(1-ethyl-5-oxo-2,5-dihydro-1H-pyrazol-3-yl)benzonitrile (0.70 g, 3.28 mmol, 1 equiv) and potassium carbonate (1.36 g, 9.85 mmol, 3 equiv) in DMSO (6.57 mL). The reaction mixture was stirred at 80° C. for 20 minutes then cooled to 22° C. and diluted with water. The mixture was extracted with ethyl acetate, and then the organic layer was washed sequentially with water (two times) and saturated aqueous sodium chloride. The washed solution was dried over anhydrous magnesium sulfate. The drying agent was filtered, and the filtrate was concentrated in vacuo to give the 3-[1-ethyl-5-(4-fluoro-2-nitrophenoxy)-1H-pyrazol-3-yl]benzonitrile. The crude reaction product was taken into the next step without further purification. Calcd (M+1)$^+$: 353.1. Found: 353.2.

Step 2:

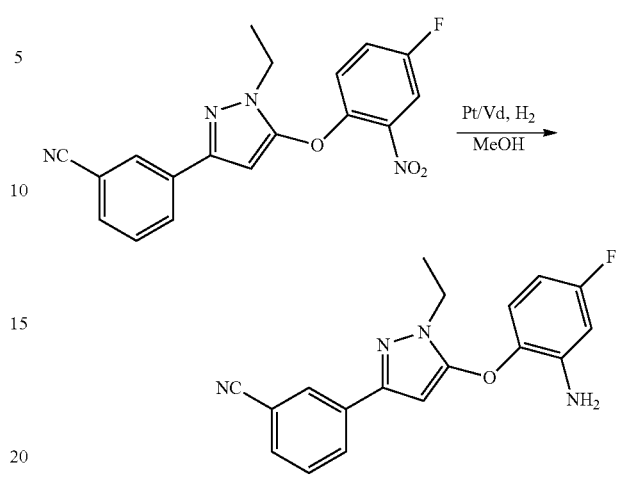

Pt/Vd (3%/0.6% wt/wt on carbon, 50 mg, 0.008 mmol, 0.005 equiv) was added to a stirring solution of 3-[1-ethyl-5-(4-fluoro-2-nitrophenoxy)-1H-pyrazol-3-yl]benzonitrile (0.54 g, 1.53 mmol, 1 equiv) in methanol (15.3 mL). A 3-way stop cock with a hydrogen balloon was installed and the reaction vessel was subjected to alternating vacuum and H$_2$ gas (4×). The resulting mixture was stirred at 22° C. for 2 hours. The mixture was then subjected to alternating vacuum and nitrogen gas (4×) before the mixture was filtered through a nylon syringe filter and concentrated in vacuo to afford 3-[5-(2-amino-4-fluorophenoxy)-1-ethyl-1H-pyrazol-3-yl]benzonitrile. The crude reaction product was carried forward without further purification. Calcd (M+1)$^+$: 323.1. Found: 323.0.

Step 3:

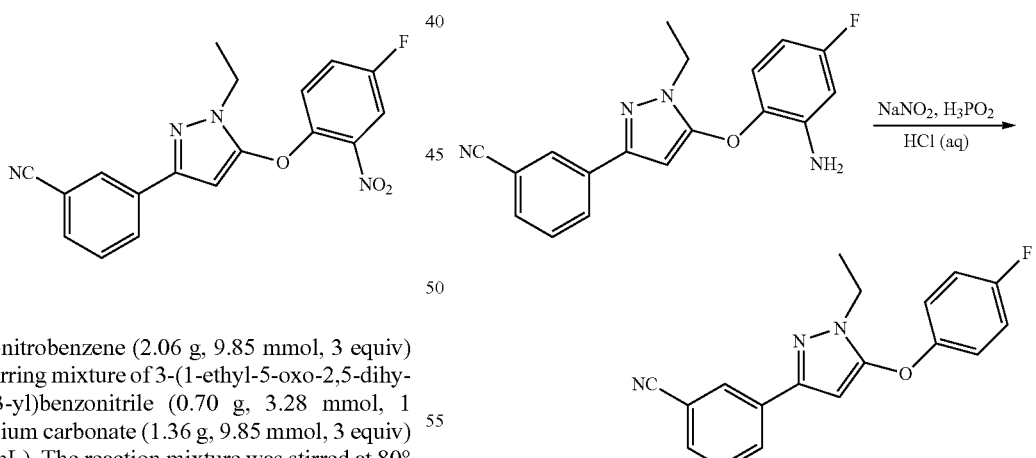

3-[5-(2-amino-4-fluorophenoxy)-1-ethyl-1H-pyrazol-3-yl]benzonitrile (0.25 g, 0.78 mmol, 1 equiv) was dissolved in a mixture of 1:1 36% aq HCl: 50% aq hypophosphoric (12.7 mL) acid and then cooled to −5° C. Sodium nitrite (3 M in water, 0.27 g, 3.88 mmol, 5 equiv) was added dropwise. The resulting mixture was warmed to 22° C. and stirred for 1 hr. The mixture was then diluted with water and extracted with ethyl acetate. The organic layer was washed with saturated aqueous sodium chloride then dried over anhydrous magnesium sulfate. The drying agent was filtered and the filtrate was concentrated in vacuo. The residue (0.24 g) was purified by flash-column chromatography on silica gel (0-45% EtOAc: Hex) to give 3-[1-ethyl-5-(4-fluorophenoxy)-1H-pyrazol-3-yl]benzonitrile. Calcd (M+1)+: 308.1. Found 308.0.

Step 4:

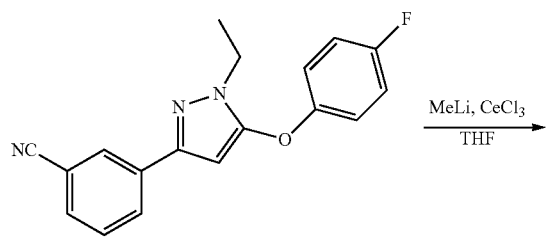

Step 5:

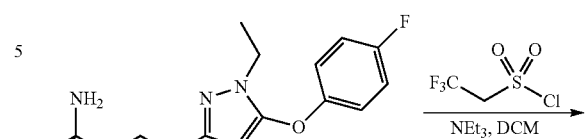

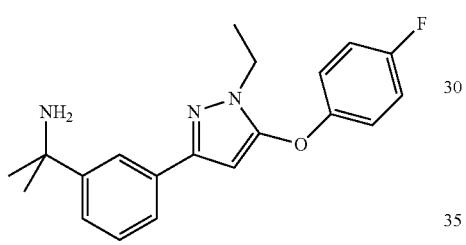

2-{3-[1-ethyl-5-(4-fluorophenoxy)-1H-pyrazol-3-yl]phenyl}propan-2-amine was prepared from 3-[1-ethyl-5-(4-fluorophenoxy)-1H-pyrazol-3-yl]benzonitrile with a procedure similar to that described in Example 1, Step 4. Calcd (M+1)+: 340.2. Found: 340.1.

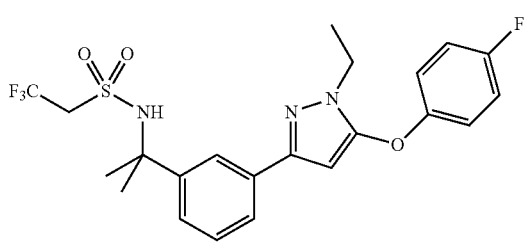 [SMILES: CCn1nc(-c2cccc(C(C)(C)NS(=O)(=O)CC(F)(F)F)c2)cc1Oc1ccc(F)cc1]

N-(1-{3-[1-ethyl-5-(4-fluorophenoxy)-1H-pyrazol-3-yl]phenyl}-1-methylethyl)-2,2,2-trifluoroethanesulfonamide was prepared from 2-{3-[1-ethyl-5-(4-fluorophenoxy)-1H-pyrazol-3-yl]phenyl}propan-2-amine with a procedure similar to that described in Example 1, Step 5. Calcd (M+1)+: 486.1. Found: 486.1.

The following was made by a similar procedure, varying the aryl fluoride used in Step 1.

| # | Structure | Name | Calc Mass (M + 1)+ | Exp Mass (M + 1)+ |
|---|-----------|------|--------------------|--------------------|
| 57 | 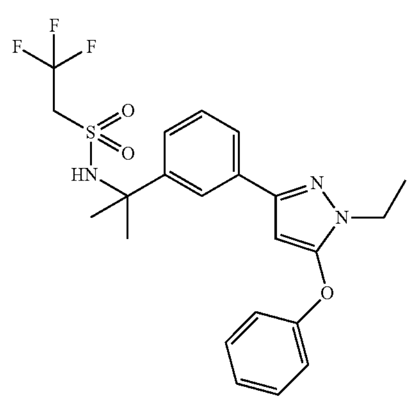 [SMILES: CCn1nc(-c2cccc(C(C)(C)NS(=O)(=O)CC(F)(F)F)c2)cc1Oc1ccccc1] | N-{1-[3-(1-ethyl-5-phenoxy-1H-pyrazol-3-yl)phenyl]-1-methylethyl}-2,2,2-trifluoroethanesulfonamide | 468.2 | 468.1 |

Example 58

N-(1-{3-[1-ethyl-5-(4-isopropylphenoxy)-1H-pyrazol-3-yl]phenyl}-1-methylethyl)-2,2,2-trifluoroethanesulfonamide

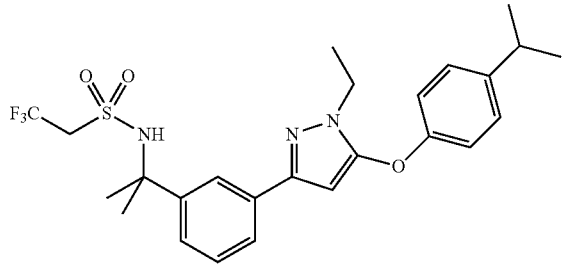 [SMILES: CCn1nc(-c2cccc(C(C)(C)NS(=O)(=O)CC(F)(F)F)c2)cc1Oc1ccc(C(C)C)cc1]

Step 1:

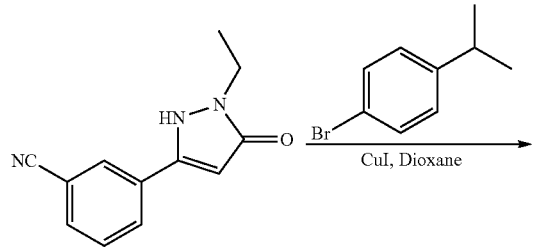

Dioxane (4.7 mL) was added to a mixture of 3-(1-ethyl-5-oxo-2,5-dihydro-1H-pyrazol-3-yl)benzonitrile (500 mg, 2.35 mmol, 1 equiv), cesium carbonate (1.53 g, 4.69 mmol, 2.00 equiv), copper (I) iodide (112 mg, 0.586 mmol, 0.250 equiv) and N,N-dimethylglycine hydrochloride (164 mg, 1.17 mmol, 0.50 equiv). The reaction flask was sealed, and nitrogen gas was bubbled through the reaction mixture for 5 minutes with a needle. The needle was removed, and 1-bromo-4-isopropylbenzene (934 mg, 4.69 mmol, 2.00 equiv) was added. The reaction flask was sealed and heated to 110° C. for 16 hours. The crude reaction mixture was loaded directly onto a silica gel column and purified by flash-column chromatography (hexanes, grading to 50% ethyl acetate-hexanes) to afford 3-[1-ethyl-5-(4-isopropylphenoxy)-1H-pyrazol-3-yl]benzonitrile (165 mg, 21%). Calcd (M+1)$^+$: 332.2. Found: 332.1.

Step 2:

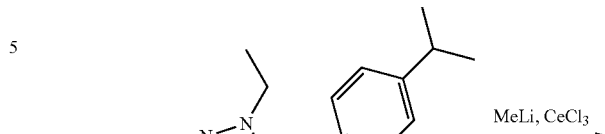

2-{3-[1-ethyl-5-(4-isopropylphenoxy)-1H-pyrazol-3-yl]phenyl}propan-2-amine was prepared from 3-[1-ethyl-5-(4-isopropylphenoxy)-1H-pyrazol-3-yl]benzonitrile with a procedure similar to that described in Example 1, Step 4. Calcd (M+1)$^+$: 364.2. Found: 364.2.

Step 3:

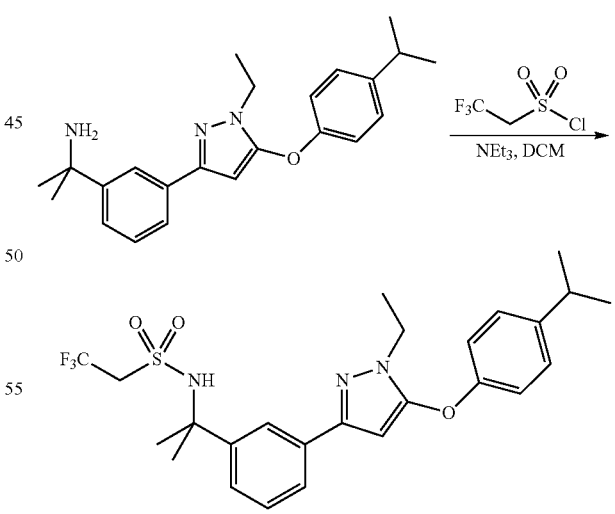

N-(1-{3-[1-ethyl-5-(4-isopropylphenoxy)-1H-pyrazol-3-yl]phenyl}-1-methylethyl)-2,2,2-trifluoroethanesulfonamide was prepared from 2-{3-[1-ethyl-5-(4-isopropylphenoxy)-1H-pyrazol-3-yl]phenyl}propan-2-amine with a procedure similar to that described in Example 1, Step 5. Calcd (M+1)$^+$: 510.2. Found: 510.1.

The following examples were prepared with similar procedures as above, varying the aryl bromide used in Step 1:

| # | Structure | Name | Calc Mass (M + 1)⁺ | Exp Mass (M + 1)⁺ |
|---|-----------|------|---------------------|--------------------|
| 59 | 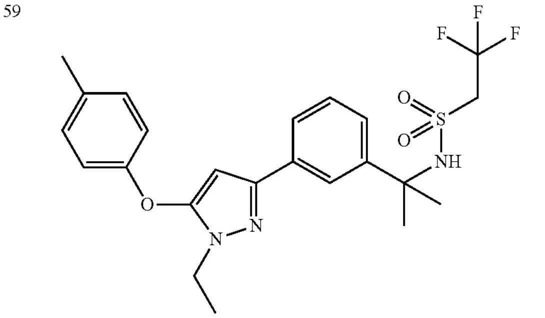 | N-(1-{3-[1-ethyl-5-(4-methylphenoxy)-1H-pyrazol-3-yl]phenyl}-1-methylethyl)-2,2,2-trifluoroethanesulfonamide | 482.2 | 482.1 |
| 60 | 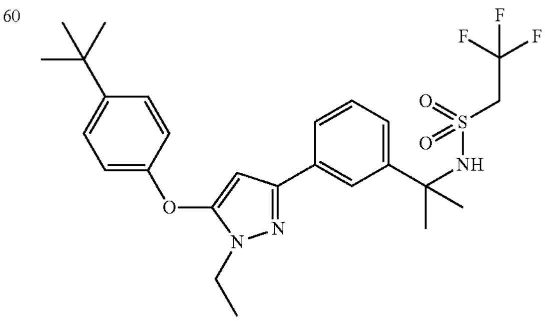 | N-(1-{3-[5-(4-tert-butylphenoxy)-1-ethyl-1H-pyrazol-3-yl]phenyl}-1-methylethyl)-2,2,2-trifluoroethanesulfonamide | 524.2 | 524.1 |

Example 61

N-(1-{3-[1-ethyl-5-(4-formylphenoxy)-1H-pyrazol-3-yl]phenyl}-1-methylethyl)-2,2,2-trifluoroethanesulfonamide

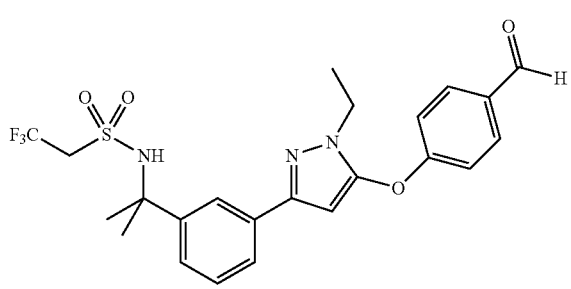 [SMILES: CCn1nc(-c2cccc(C(C)(C)NS(=O)(=O)CC(F)(F)F)c2)cc1Oc1ccc(C=O)cc1]

Step 1:

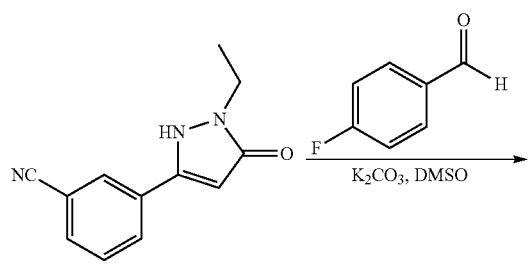

3-[1-ethyl-5-(4-formylphenoxy)-1H-pyrazol-3-yl]benzonitrile was prepared from 3-(1-ethyl-5-oxo-2,5-dihydro-1H-pyrazol-3-yl)benzonitrile and 4-fluorobenzaldehyde with a procedure similar to Example 1, Step 3. Calc'd (M+1) 318.1. Found: 318.0

Step 2:

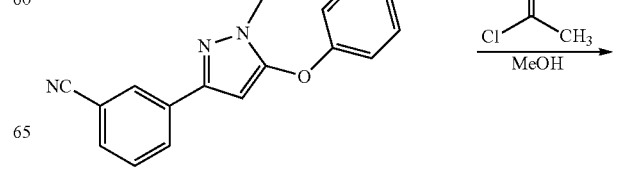

-continued

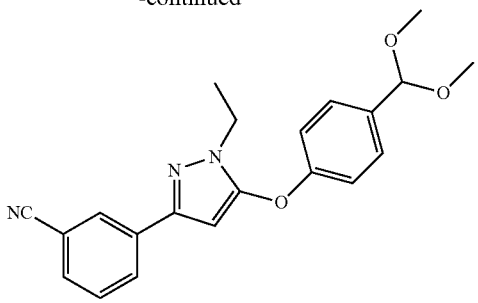

Acetic anhydride (0.24 mL, 3.3 mmol, 0.1 equiv) was added to a stirring solution of 3-[1-ethyl-5-(4-formylphenoxy)-1H-pyrazol-3-yl]benzonitrile (10.5 g, 33.0 mmol, 1 equiv) in methanol (66 mL). 4A molecular sieves were then added and the mixture was stirred at 50° C. for 3 hours. The sieves were filtered away and the filtrate was purified by flash chromatography (0-40% EtOAc:Hex) to give 3-{5-[4-(dimethoxymethyl)phenoxy]-1-ethyl-1H-pyrazol-3-yl}benzonitrile (77% yield). Calc'd (M+1) 364.2. Found: 364.1

Step 3:

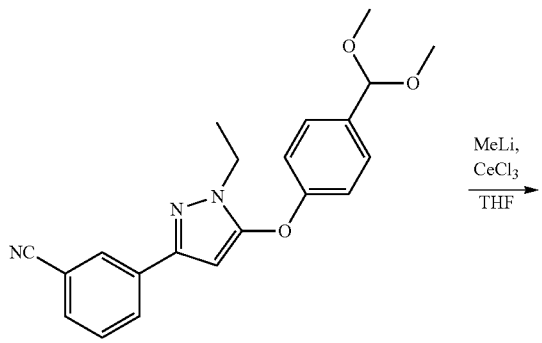

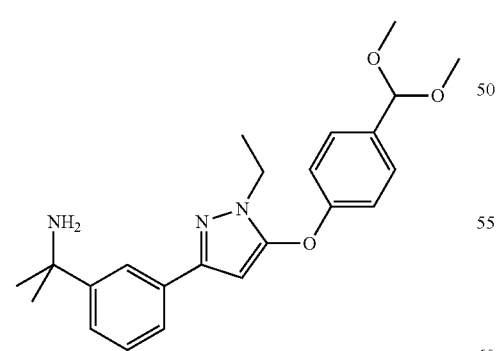

2-(3-{5-[4-(dimethoxymethyl)phenoxy]-1-ethyl-1H-pyrazol-3-yl}phenyl)propan-2-amine was prepared from 3-{5-[4-(dimethoxymethyl)phenoxy]-1-ethyl-1H-pyrazol-3-yl}benzonitrile with a procedure similar to that described in Example 1, Step 4. Calcd (M+1)+: 396.2. Found: 396.1. (page 0080)

Step 4:

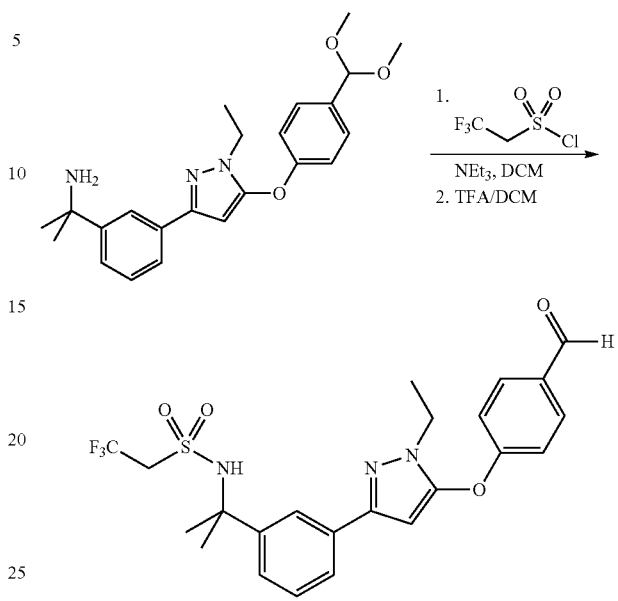

2-(3-{5-[4-(dimethoxymethyl)phenoxy]-1-ethyl-1H-pyrazol-3-yl}phenyl)propan-2-amine (8.84 g, 22.35 mmol, 1 equiv) was stirred at −78° C. in anhydrous DCM (224 mL). 2,2,2-trifluoroethanesulfonyl chloride (4.90 g, 26.80 mmol, 1.2 equiv) was added, followed by triethylamine (4.67 mL, 33.50 mmol, 1.5 equiv). After stirring at −78° C. for 10 minutes the cooling bath was removed and the mixture was allowed to slowly warm to 22° C. Upon reaching 22° C. 7:1 Water:TFA (4.5 equiv) was added to the vigorously stirring reaction mixture. After stirring for 1 hour the mixture was partitioned between water and DCM. The organic layer was washed with brine, dried over anhydrous magnesium sulfate and concentrated in vacuo to give the N-(2-{3-[1-ethyl-5-(4-formylphenoxy)-1H-pyrazol-3-yl]phenyl}propan-2-yl)-2,2,2-trifluoroethanesulfonamide (98% Yield). Calcd (M+1)+: 496.1. Found: 496.1.

Example 62

N-[1-(3-{1-ethyl-5-[4-(hydroxymethyl)phenoxy]-1H-pyrazol-3-yl}phenyl)-1-methylethyl]-2,2,2-trifluoroethanesulfonamide

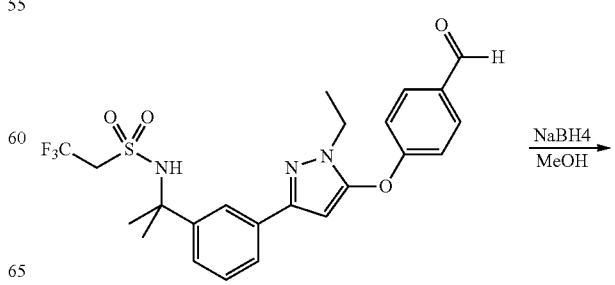

-continued

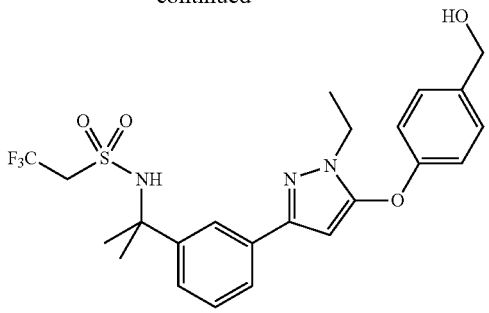

Sodium borohydride (13 mg, 0.35 mmol, 2.0 equiv) was added to a solution of N-(1-{3-[1-ethyl-5-(4-formylphenoxy)-1H-pyrazol-3-yl]phenyl}-1-methylethyl)-2,2,2-trifluoroethanesulfonamide (87 mg, 0.18 mmol, 1 equiv) in methanol (1.8 mL) at 0° C. The reaction mixture was stirred for 60 minutes at 0° C., then added aqueous hydrochloric acid solution (1 M) and stirred for an additional 5 minutes. The quenched solution was partitioned between ethyl acetate and water. The organic layer was washed with saturated aqueous sodium chloride solution, and the washed solution was dried over sodium sulfate. The dried solution was filtered, and the filtrate was concentrated. The residue was purified by flash-column chromatography (hexanes, grading to 75% ethyl acetate-hexanes) to afford N-[1-(3-{1-ethyl-5-[4-(hydroxymethyl)phenoxy]-1H-1-pyrazol-3-yl}phenyl)-1-methylethyl]-2,2,2-trifluoroethanesulfonamide (80 mg 92%). Calcd (M+1)$^+$: 498.2. Found: 498.1.

Example 63

N-[1-(3-{1-ethyl-5-[4-(fluoromethyl)phenoxy]-1H-pyrazol-3-yl}phenyl)-1-methylethyl]-2,2,2-trifluoroethanesulfonamide

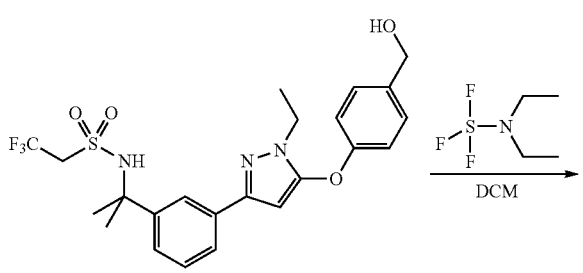

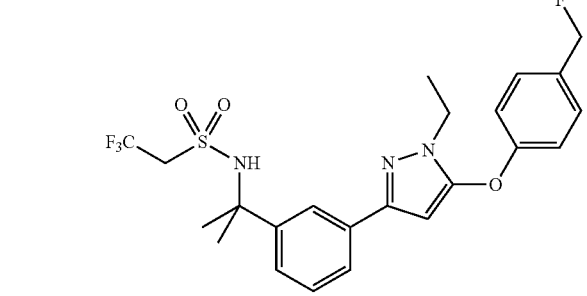

N-ethyl-N-(trifluoro-λ$^4$-sulfanyl)ethanamine (DAST, 0,021 mL, 0.16 mmol, 1.3 equiv) was added to a solution of N-[1-(3-{1-ethyl-5-[4-(hydroxymethyl)phenoxy]-1H-pyrazol-3-yl}phenyl)-1-methylethyl]-2,2,2-trifluoroethanesulfonamide (62 mg, 0.13 mmol, 1 equiv) in dichloromethane (1.2 mL) at -78° C. The reaction mixture was stirred at -78° C. for 5 minutes, then saturated sodium hydrogencarbonate was added. The crude mixture was extracted with ethyl acetate. The organic layer was washed with saturated aqueous sodium chloride solution, and the washed solution was dried over sodium sulfate. The dried solution was filtered, and the filtrate was concentrated. The residue was purified by flash-column chromatography (hexanes, grading to 50% ethyl acetate-hexanes) to afford N-[1-(3-{1-ethyl-5-[4-(fluoromethyl)phenoxy]-1H-pyrazol-3-yl}phenyl)-1-methylethyl]-2,2,2-trifluoroethanesulfonamide (22 mg, 35%). Calcd (M+1)$^+$: 500.2. Found: 500.1.

Example 64

N-[1-(3-{5-[4-(difluoromethyl)phenoxy]-1-ethyl-1H-pyrazol-3-yl}phenyl)-1-methylethyl]-2,2,2-trifluoroethanesulfonamide

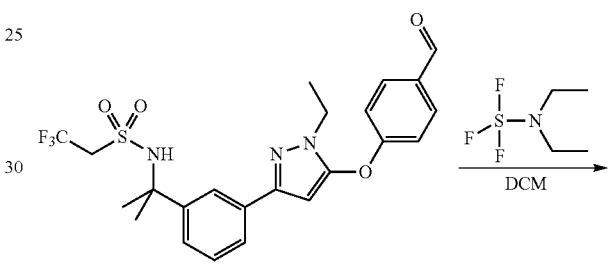

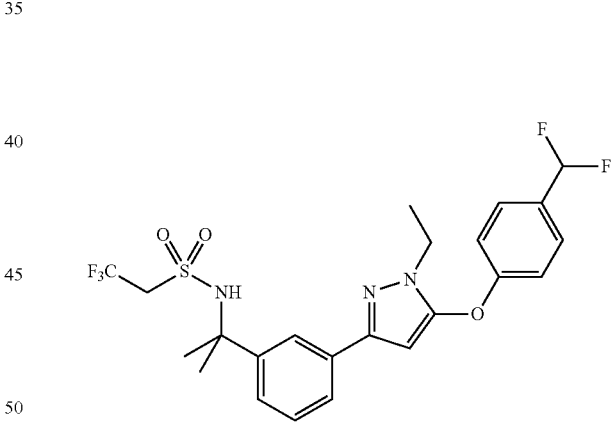

N-ethyl-N-(trifluoro-λ$^4$-sulfanyl)ethanamine (DAST, 0.033 mL, 0.25 mmol, 2.5 equiv) was added to a solution of N-(1-{3-[1-ethyl-5-(4-formylphenoxy)-1H-pyrazol-3-yl]phenyl}-1-methylethyl)-2,2,2-trifluoroethanesulfonamide (50 mg, 0.10 mmol, 1 equiv) in dichloromethane (1.0 mL) at -78° C. The cooling bath was removed, and after stirring for 90 minutes at 22° C., and additional portion of DAST (0.033 mL, 0.25 mmol, 2.5 equiv) was added. Stirred for 40 h, then partitioned between ethyl acetate and water. The organic layer was washed with saturated aqueous sodium chloride solution, and the washed solution was dried over sodium sulfate. The dried solution was filtered, and the filtrate was concentrated. The residue was purified by flash-column chromatography (hexanes, grading to 50% ethyl acetate-hexanes) to afford N-[1-(3-{5-[4-(difluoromethyl)phenoxy]-1-ethyl-1H-pyrazol-3-yl}phenyl)-1-methylethyl]-2,2,2-trifluoroethane-sulfonamide (14 mg, 27%). Calcd (M+1)⁺: 518.2. Found: 518.0.

Example 65

N-[1-(3-{1-ethyl-5-[4-(1-hydroxyethyl)phenoxy]-1H-pyrazol-3-yl}phenyl)-1-methylethyl]-2,2,2-trifluoroethanesulfonamide

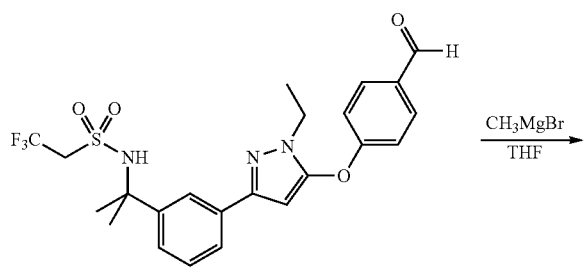

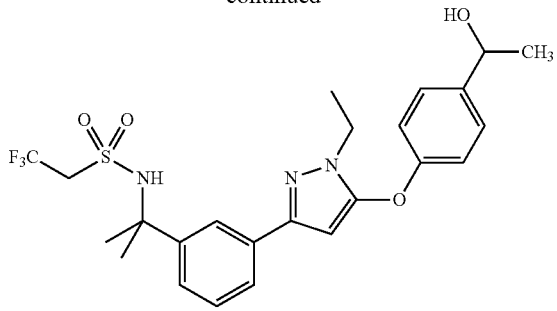

Methylmagnesium bromide (3.00 M in diethyl ether, 0.135 mL, 0.404 mmol, 2.00 equiv) was added to a solution of N-(1-{3-[1-ethyl-5-(4-formylphenoxy)-1H-pyrazol-3-yl]phenyl}-1-methylethyl)-2,2,2-trifluoroethanesulfonamide (100 mg, 0.202 mmol, 1 equiv) in tetrahydrofuran (2.0 mL) at 0° C. The reaction mixture was stirred at 0° C. for 5 minutes, then was treated with saturated aqueous ammonium chloride solution. The biphasic mixture was partitioned between ethyl acetate and water. The organic layer was washed with saturated aqueous sodium chloride solution, and the washed solution was dried over sodium sulfate. The dried solution was filtered, and the filtrate was concentrated. The residue was purified by flash-column chromatography (hexanes, grading to 90% ethyl acetate-hexanes) to afford N-[1-(3-{1-ethyl-5-[4-(1-hydroxyethyl)phenoxy]-1H-pyrazol-3-yl}phenyl)-1-methylethyl]-2,2,2-trifluoroethanesulfonamide (79 mg, 77%). Calcd (M+1)⁺: 512.2. Found: 512.1.

The following examples were prepared from N-(1-{3-[1-ethyl-5-(4-formylphenoxy)-1H-pyrazol-3-yl]phenyl}-1-methylethyl)-2,2,2-trifluoroethanesulfonamide with similar procedures, varying the alkylmagnesium halide used above:

| # | Structure | Name | Calc Mass (M + 1)⁺ | Exp Mass (M + 1)⁺ |
|---|-----------|------|--------------------|--------------------|
| 66 | 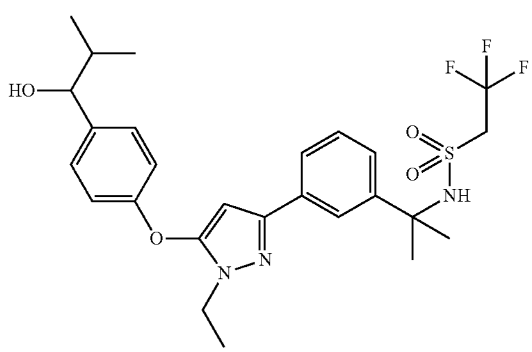 | N-[1-(3-{1-ethyl-5-[4-(1-hydroxy-2-methylpropyl)phenoxy]-1H-pyrazol-3-yl}phenyl)-1-methylethyl]-2,2,2-trifluoroethanesulfonamide | 540.2 | 540.1 |
| 67 | 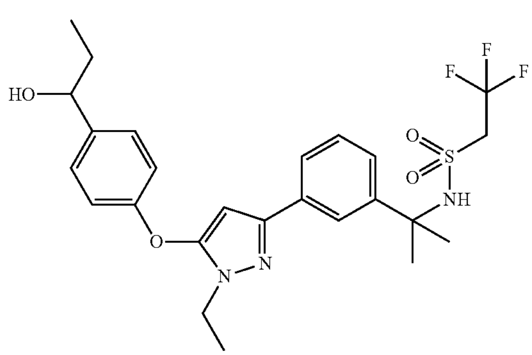 [SMILES: CCC(O)c1ccc(Oc2cc(-c3cccc(C(C)(C)NS(=O)(=O)CC(F)(F)F)c3)nn2CC)cc1] | N-[1-(3-{1-ethyl-5-[4-(1-hydroxypropyl)phenoxy]-1H-pyrazol-3-yl}phenyl)-1-methylethyl]-2,2,2-trifluoroethanesulfonamide | 526.2 | 526.1 |

Example 68

N-[1-(3-{1-ethyl-5-[4-(1-fluoroethyl)phenoxy]-1H-pyrazol-3-yl}phenyl)-1-methylethyl]-2,2,2-trifluoroethanesulfonamide

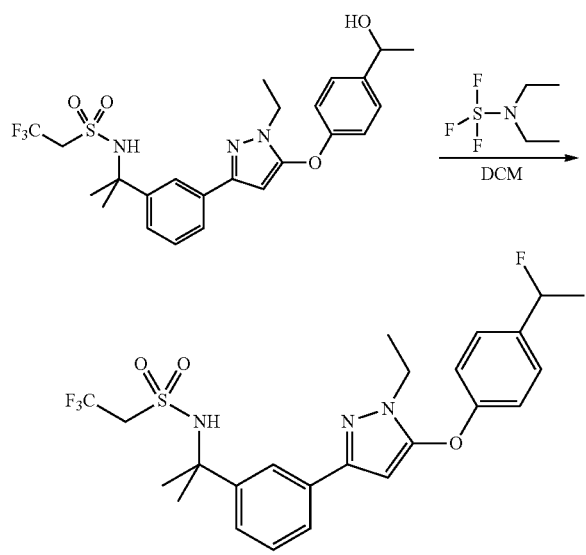

N-ethyl-N-(trifluoro-λ⁴-sulfanyl)ethanamine (DAST, 0.020 mL, 0.15 mmol, 1.3 equiv) was added to a solution of N-[1-(3-{1-ethyl-5-[4-(1-hydroxyethyl)phenoxy]-1H-pyrazol-3-yl}phenyl)-1-methylethyl]-2,2,2-trifluoroethanesulfonamide (62 mg, 0.12 mmol, 1 equiv) in dichloromethane (1.2 mL) at −78° C. The reaction mixture was stirred at −78° C. for 5 minutes, then saturated sodium hydrogencarbonate was added. The crude mixture was extracted with ethyl acetate. The organic layer was washed with saturated aqueous sodium chloride solution, and the washed solution was dried over sodium sulfate. The dried solution was filtered, and the filtrate was concentrated. The residue was purified by flash-column chromatography (hexanes, grading to 50% ethyl acetate-hexanes) to afford N-[1-(3-{1-ethyl-5-[4-(1-fluoroethyl)phenoxy]-1H-pyrazol-3-yl}phenyl)-1-methylethyl]-2,2,2-trifluoroethanesulfonamide (40 mg, 64%). Calcd $(M+1)^+$: 514.2. Found: 514.1.

Example 69

N-(1-{3-[5-(4-acetylphenoxy)-1-ethyl-1H-pyrazol-3-yl]phenyl}-1-methylethyl)-2,2,2-trifluoroethanesulfonamide

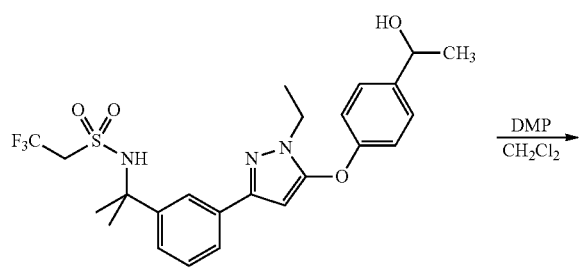

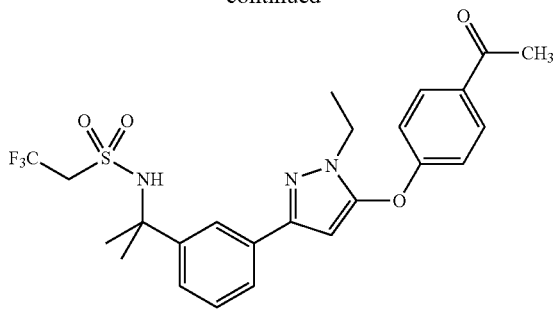

Dess-Martin periodinane (415 mg, 0.977 mmol, 2.00 equiv) was added to a solution of N-[1-(3-{1-ethyl-5-[4-(1-hydroxyethyl)phenoxy]-1H-pyrazol-3-yl}phenyl)-1-methylethyl]-2,2,2-trifluoroethanesulfonamide (250 mg, 0.489 mmol, 1 equiv) in dichloromethane (4.9 mL) at 22° C. The reaction mixture was stirred for 2 hours, and then saturated aqueous sodium thiosulfate solution (3 mL) and saturated aqueous sodium bicarbonate solution (3 mL) were added. The biphasic mixture was stirred for 15 minutes, then was partitioned between ethyl acetate and water. The organic layer was washed with saturated aqueous sodium chloride solution, and the washed solution was dried over sodium sulfate. The dried solution was filtered, and the filtrate was concentrated. The residue was purified by flash-column chromatography (hexanes, grading to 90% ethyl acetate-hexanes) to afford N-(1-{3-[5-(4-acetylphenoxy)-1-ethyl-1H-pyrazol-3-yl]phenyl}-1-methylethyl)-2,2,2-trifluoroethanesulfonamide (139 mg, 56%) Calcd $(M+1)^+$: 510.2. Found: 510.1.

Example 70

N-[1-(3-{1-ethyl-5-[4-(1-hydroxy-1-methylethyl)phenoxy]-1H-pyrazol-3-yl}phenyl)-1-methylethyl]-2,2,2-trifluoroethanesulfonamide N-[1-(3-{1-ethyl-5-[4-(1,2,2,2-tetrafluoroethyl)phenoxy]-1H-pyrazol-3-yl}phenyl)-1-methylethyl]-2,2,2-trifluoroethanesulfonamide was prepared from N-(1-{3-[5-(4- acetylphenoxy)-1-ethyl-1H-pyrazol-3-yl]phenyl}-1-methylethyl)-2,2,2-trifluoroethanesulfonamide with a procedure similar to that reported for Example 65. Calcd (M+1)$^+$: 526.2. Found: 526.1.

Example 71

N-[1-(3-{1-ethyl-5-[4-(2,2,2-trifluoro-1-hydroxyethyl)phenoxy]-1H-pyrazol-3-yl}phenyl)-1-methylethyl]-2,2,2-trifluoroethanesulfonamide

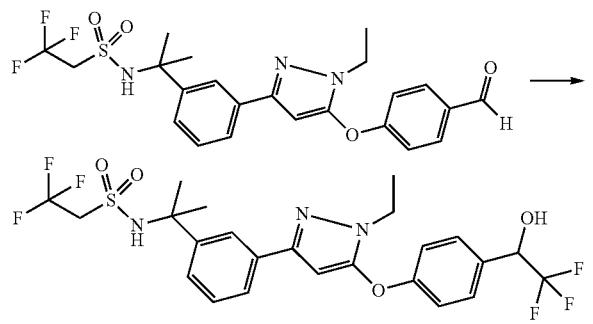

Trimethyl(trifluoromethyl)silane (0.62 mL, 4.0 mmol, 1.2 equiv) and tetrabutylammonium fluoride (1.0 M in THF, 0.67 mL, 0.67 mmol, 0.20 equiv) were added sequentially to a solution of N-(1-{3-[1-ethyl-5-(4-formylphenoxy)-1H-pyrazol-3-yl]phenyl}-1-methylethyl)-2,2,2-trifluoroethanesulfonamide (1.65 g, 3.33 mmol, 1 equiv) in tetrahydrofuran (3.3 mL) at 0° C. The reaction mixture was stirred for 15 minutes at 0° C., and then was warmed to 22° C. After stirring for 2.5 hours, aqueous hydrochloric acid solution (2 N) was added and the reaction mixture was stirred for an additional 40 minutes. The crude product was partitioned between ethyl acetate and water. The organic layer was washed with saturated aqueous sodium chloride solution, and the washed solution was dried over sodium sulfate. The dried solution was filtered, and the filtrate was concentrated. The residue was purified by flash-column chromatography (hexanes, grading to 45% ethyl acetate-hexanes) to afford N-[1-(3-{1-ethyl-5-[4-(2,2,2-trifluoro-1-hydroxyethyl)phenoxy]-1H-pyrazol-3-yl}phenyl)-1-methylethyl]-2,2,2-trifluoroethanesulfonamide (43 mg, 2%). Calcd (M+1)$^+$: 566.2. Found: 566.0.

Example 72

N-[1-(3-{1-ethyl-5-[4-(1,2,2,2-tetrafluoroethyl)phenoxy]-1H-pyrazol-3-yl}phenyl)-1-methylethyl]-2,2,2-trifluoroethanesulfonamide

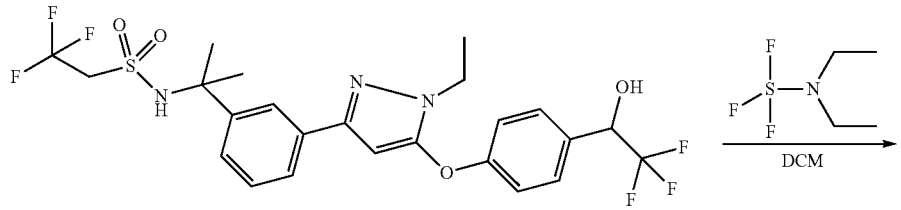

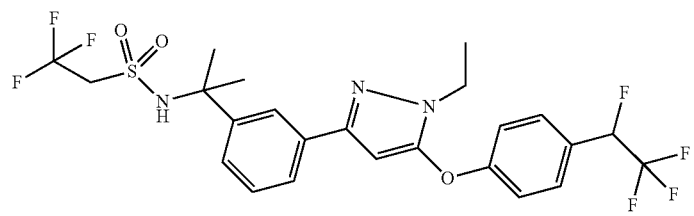

N-[1-(3-{1-ethyl-5-[4-(1,2,2,2-tetrafluoroethyl)phenoxy]-1H-pyrazol-3-yl}phenyl)-1-methylethyl]-2,2,2-trifluoroethanesulfonamide was prepared from N-[1-(3-{1-ethyl-5-[4-(2,2,2-trifluoro-1-hydroxyethyl)phenoxy]-1H-pyrazol-3-yl}phenyl)-1-methylethyl]-2,2,2-trifluoroethanesulfonamide with a procedure similar to that used for Example 68. Calcd (M+1)+: 568.2. Found: 568.1.

Example 73

N-[1-(3-{1-ethyl-5-[4-(trifluoroacetyl)phenoxy]-1H-pyrazol-3-yl}phenyl)-1-methylethyl]-2,2,2-trifluoroethanesulfonamide

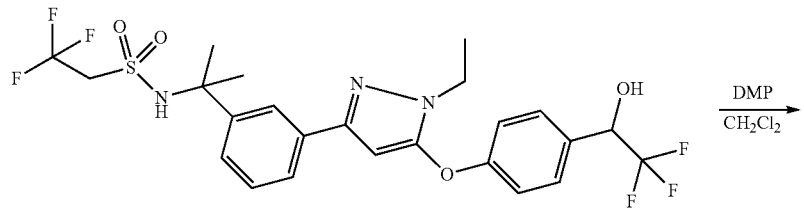

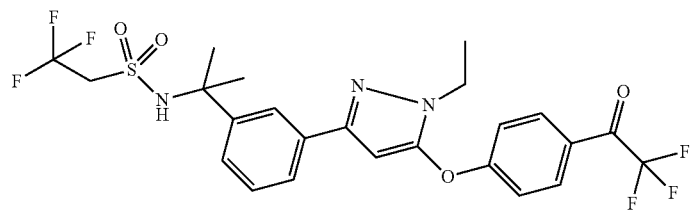

N-[1-(3-{1-ethyl-5-[4-(trifluoroacetyl)phenoxy]-1H-pyrazol-3-yl}phenyl)-1-methylethyl]-2,2,2-trifluoroethanesulfonamide was prepared from N-[1-(3-{1-ethyl-5-[4-(2,2,2-trifluoro-1-hydroxyethyl)phenoxy]-1H-pyrazol-3-yl}phenyl)-1-methylethyl]-2,2,2-trifluoroethanesulfonamide with a procedure similar to that used for Example 69. Calcd (M+1)+: 564.1. Found: 564.1.

Example 74

4-({1-ethyl-3-[3-(1-methyl-1-{[(2,2,2-trifluoroethyl)sulfonyl]amino}ethyl)phenyl]-1H-pyrazol-5-yl}oxy)-N-(tetrahydrofuran-2-ylmethyl)benzamide

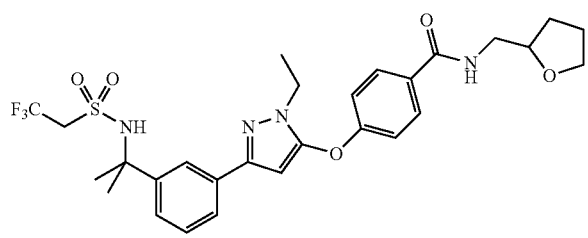 [SMILES: CCn1nc(-c2cccc(C(C)(C)NS(=O)(=O)CC(F)(F)F)c2)cc1Oc1ccc(C(=O)NCC2CCCO2)cc1]

Step 1:

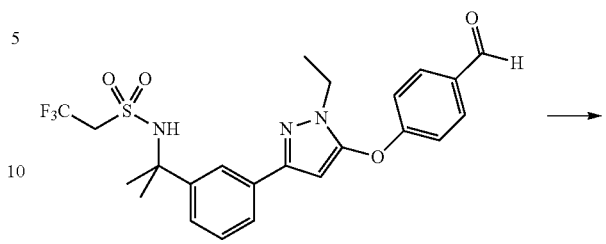

-continued

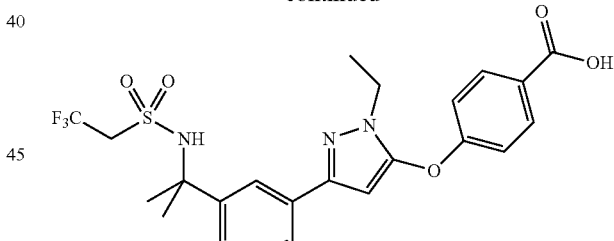

Sodium chlorite (71 mg, 0.78 mmol, 4.0 equiv) was added to a mixture of N-(1-{3-[1-ethyl-5-(4-formylphenoxy)-1H-pyrazol-3-yl]phenyl}-1-methylethyl)-2,2,2-trifluoroethanesulfonamide (97 mg, 0.20 mmol, 1 equiv), 2-methyl-2-butene (1 mL), aqueous sodium dihydrogenphosphate solution (20% w/w, 0.7 mL) and methanol (2.8 mL). The biphasic mixture was stirred for 90 minutes, then was partitioned between ethyl acetate and saturated aqueous sodium chloride solution. The organic layer was dried over sodium sulfate. The dried solution was filtered, and the filtrate was concentrated to afford 4-({1-ethyl-3-[3-(1-methyl-1-{[(2,2,2-trifluoroethyl)sulfonyl]amino}ethyl)phenyl]-1H-pyrazol-5-yl}oxy)benzoic acid. Calcd (M+1)+: 512.1. Found: 512.1.

Step 2:

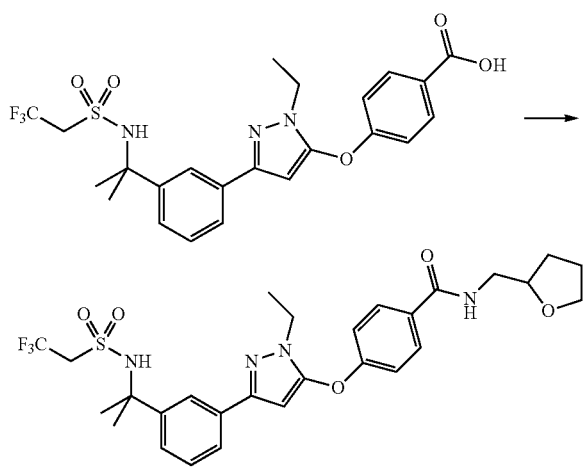

(1-benzotriazol-1-yloxy)[tris(dimethylamino)]phosphonium hexafluorophosphate (52 mg, 0.12 mmol, 1.2 equiv) and diisopropylethylamine (38 mg, 0.29 mmol, 3 equiv) were added to a stirring solution of 4-({1-ethyl-3-[3-(2-{[(2,2,2-trifluoroethyl)sulfonyl]amino}propan-2-yl)phenyl]-1H-pyrazol-5-yl}oxy)benzoic acid (50 mg, 0.10 mmol, 1 equiv) in DMF (1 mL). 1-(tetrahydrofuran-2-yl)methanamine (20 mg, 0.20 mmol, 2 equiv) was then added and the mixture was stirred at 22° C. for 16 hours. The mixture was purified directly by reversed phase HPLC (0-95% acetonitrile:water with 0.025% TFA). Pure fractions were identified, combined, and lyophilized to give 4-({1-ethyl-3-[3-(2-{[(2,2,2-trifluoroethyl)sulfonyl]amino}propan-2-yl)phenyl]-1H phenyl]-1H-pyrazol-5-yl}oxy)-N-(tetrahydrofuran-2-ylmethyl)benzamide (38% yield). Calc'd (M+1)$^+$: 595.2. Found: 595.1

Example 75

N-[1-(3-{1-ethyl-5-[4-(5-methyl-1,3,4-oxadiazol-2-yl)phenoxy]-1H-pyrazol-3-yl}phenyl)-1-methylethyl]-2,2,2-trifluoroethanesulfonamide

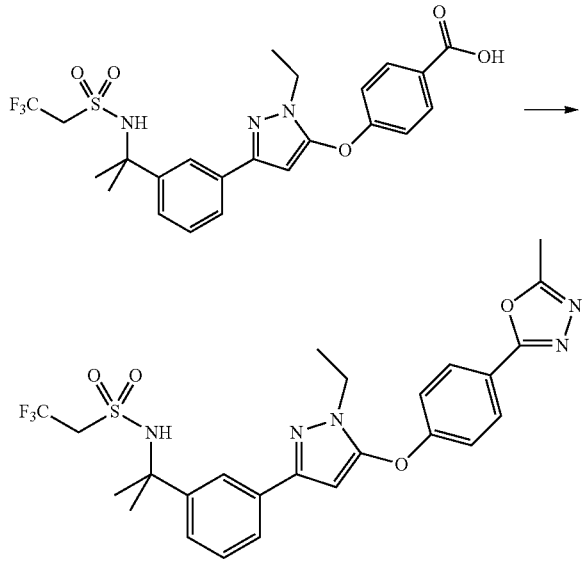

(1-benzotriazol-1-yloxy)[tris(dimethylamino)]phosphonium hexafluorophosphate (161 mg, 0.36 mmol, 1.2 equiv) and diisopropylethylamine (117 mg, 0.91 mmol, 3 equiv) were added to a stirring solution of 4-({1-ethyl-3-[3-(2-{[(2,2,2-trifluoroethyl)sulfonyl]amino}propan-2-yl)phenyl]-1H-pyrazol-5-yl}oxy)benzoic acid (155 mg, 0.30 mmol, 1 equiv) in DMF (3 mL). Acetohydrazide (45 mg, 0.61 mmol, 2 equiv) was then added and the mixture was stirred at 22° C. for 16 hours. The mixture was purified directly by reversed phase HPLC (0-95% acetonitrile:water with 0.025% TFA). Pure fractions were identified, combined, and lyophilized to give N-{2-[3-(5-{4-[(2-acetylhydrazinyl)carbonyl]phenoxy}-1-ethyl-1H-pyrazol-3-yl)phenyl]propan-2-yl}-2,2,2-trifluoroethanesulfonamide (35% yield). This material was stirred in THF (1 mL) at 22° C. and 3,3,3-triethyl-1-(methoxycarbonyl)diazathian-3-ium-1-ide 2,2-dioxide (38 mg, 0.16 mmol, 1.5 equiv) was added. The resulting mixture was stirred at 22° C. for 16 hours then purified directly by reversed phase HPLC (0-95% acetonitrile:water with 0.025% TFA). Pure fractions were identified, combined, and lyophilized to give the title compound (21% yield). Calc'd (M+1)$^+$: 550.2. Found: 550.1.

Example 76

N-[1-(3-{1-ethyl-5-[4-(1,3-oxazol-5-yl)phenoxy]-1H-pyrazol-3-yl}phenyl)-1-methylethyl]-2,2,2-trifluoroethanesulfonamide

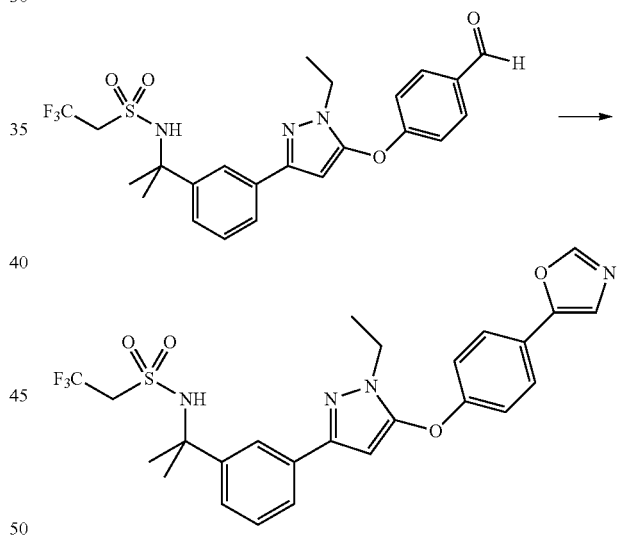

N-(2-{3-[1-ethyl-5-(4-formylphenoxy)-1H-pyrazol-3-yl]phenyl}propan-2-yl)-2,2,2-trifluoroethanesulfonamide (340 mg, 0.69 mmol, 1 equiv) was added to a suspension of potassium carbonate (237 mg, 1.72 mmol, 2.5 equiv) stirring in MeOH (3.4 mL) at 22° C. 1-[(isocyanomethyl)sulfonyl]-4-methylbenzene isocyanomethyl 4-methylphenyl sulfone (161 mg, 0.82 mmol, 1.2 equiv) was added and the resulting mixture was stirred at 22° C. for 30 minutes. The reaction was diluted with water and extracted with ethyl acetate. The organic layer was washed with saturated aqueous ammonium chloride, dried over anhydrous magnesium sulfate and concentrated in vacuo. The residue was purified by flash chromatography (0-40% EtOAc:Hex). Fractions were identified, combined and concentrated in vacuo but the isolated material was not pure. The residue was then purified by reversed phase HPLC (0-95% acetonitrile:water with 0.025% TFA). Pure fractions were identified, combined, basified with saturated aqueous sodium bicarbonate, and extracted with ethyl acetate. The organic layer was washed with saturated aqueous sodium chloride, dried over anhydrous magnesium sulfate and concentrated in vacuo to give the title compound (3% yield). Calc'd (M+1)⁺: 535.1. Found: 535.1.

Example 77a

N-(1-{3-[1-ethyl-5-(4-{[(tetrahydrofuran-2-ylmethyl)amino]methyl}phenoxy)-1H-pyrazol-3-yl]phenyl}-1-methylethyl)-2,2,2-trifluoroethanesulfonamide

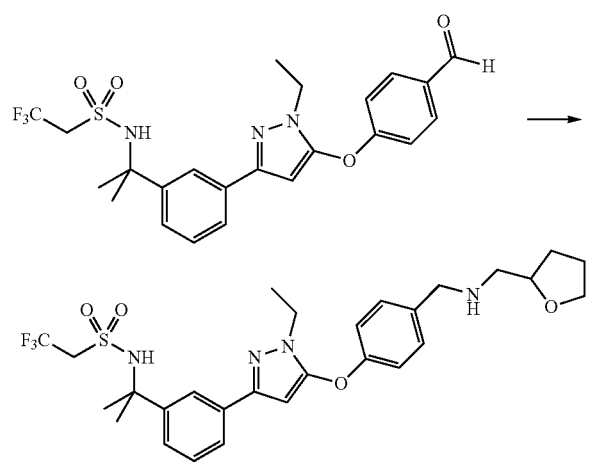

1-(tetrahydrofuran-2-yl)methanamine (12.3 mgs, 0.121 mmol, 1.2 equiv) followed by Si-bound cyanoborohydride (322 mg, 0.303 mmol, 3.0 equiv, 0.94 mmol/g) were added to N-(2-{3-[1-ethyl-5-(4-formylphenoxy)-1H-pyrazol-3-yl]phenyl}propan-2-yl)-2,2,2-trifluoroethanesulfonamide (50.0 mg, 0.101 mmol, 1 equiv) stirring in DMF (with 0.05% acetic acid v:v, 0.5 mL). The resulting mixture was stirred at 22° C. for 16 hours then filtered through a 0.45 micron nylon syringe filter and flushed with methanol. The filtrate was purified by reversed phase HPLC (0-95% acetonitrile:water with 0.025% TFA v:v). Pure fractions were identified, combined, basified with saturated aqueous sodium bicarbonate and extracted with ethyl acetate. The organic layer was washed with saturated aqueous sodium chloride and dried over anhydrous magnesium sulfate. The drying agent was filtered away and the filtrate was concentrated in vacuo to give N-(2-{3-[1-ethyl-5-(4-{[(tetrahydrofuran-2-ylmethyl)amino]methyl}phenoxy)-1H-pyrazol-3-yl]phenyl}propan-2-yl)-2,2,2-trifluoroethanesulfonamide. Calc'd (M+1) 581.2. Found: 581.2

The following examples were made from N-(1-{3-[1-ethyl-5-(4-formylphenoxy)-1H-pyrazol-3-yl]phenyl}-1-methylethyl)-2,2,2-trifluoroethanesulfonamide using a similar procedure, varying the amine used in the reductive amination:

| # | Structure | Name | Calc Mass (M + 1)⁺ | Exp Mass (M + 1)⁺ |
|---|---|---|---|---|
| 77 | 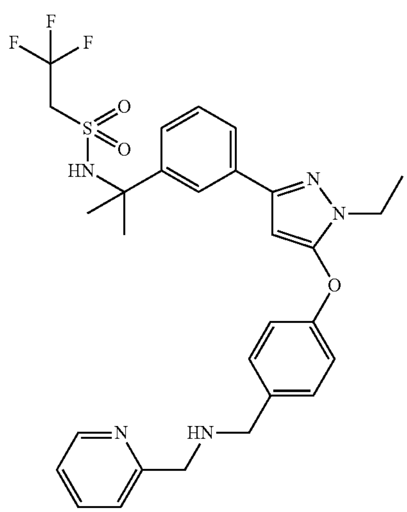 [SMILES: CCn1nc(-c2cccc(C(C)(C)NS(=O)(=O)CC(F)(F)F)c2)cc1Oc1ccc(CNCc2ccccn2)cc1] | N-(1-{3-[1-ethyl-5-(4-{[(pyridin-2-ylmethyl)amino]methyl}phenoxy)-1H-pyrazol-3-yl]phenyl}-1-methylethyl)-2,2,2-trifluoroethanesulfonamide | 588.2 | 588.1 |

| # | Structure | Name | Calc Mass (M + 1)+ | Exp Mass (M + 1)+ |
|---|-----------|------|--------------------|--------------------|
| 78 | 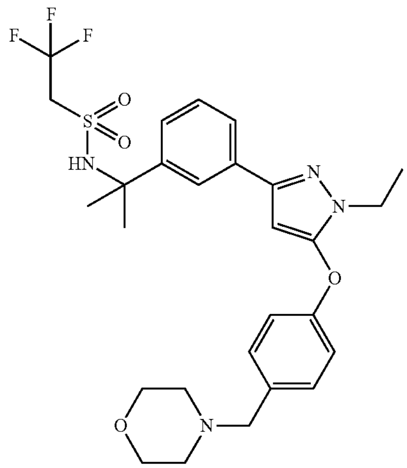 [SMILES: CCn1nc(-c2cccc(C(C)(C)NS(=O)(=O)CC(F)(F)F)c2)cc1Oc1ccc(CN2CCOCC2)cc1] | N-[1-(3-{1-ethyl-5-[4-(morpholin-4-ylmethyl)phenoxy]-1H-pyrazol-3-yl}phenyl)-1-methylethyl]-2,2,2-trifluoroethanesulfonamide | 567.2 | 567.1 |
| 79 | 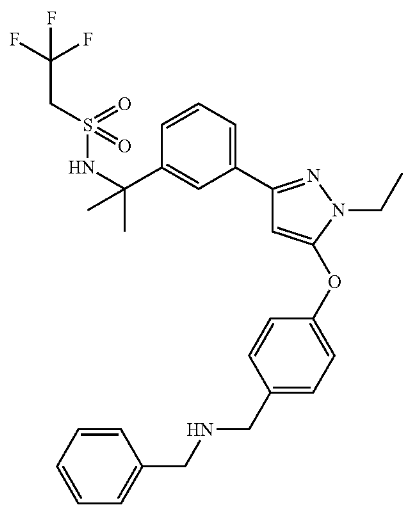 [SMILES: CCn1nc(-c2cccc(C(C)(C)NS(=O)(=O)CC(F)(F)F)c2)cc1Oc1ccc(CNCc2ccccc2)cc1] | N-{1-[3-(5-{4-[(benzylamino)methyl]phenoxy}-1-ethyl-1H-pyrazol-3-yl)phenyl]-1-methylethyl}-2,2,2-trifluoroethanesulfonamide | 587.2 | 587.1 |
| 80 | 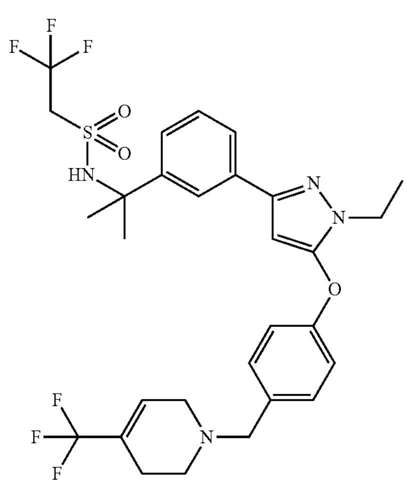 [SMILES: CCn1nc(-c2cccc(C(C)(C)NS(=O)(=O)CC(F)(F)F)c2)cc1Oc1ccc(CN2CC=C(C(F)(F)F)CC2)cc1] | N-(1-{3-[1-ethyl-5-(4-{[4-(trifluoromethyl)-3,6-dihydropyridin-1(2H)-yl]methyl}phenoxy)-1H-pyrazol-3-yl]phenyl}-1-methylethyl)-2,2,2-trifluoroethanesulfonamide | 631.2 | 631.1 |

-continued

| # | Structure | Name | Calc Mass (M + 1)+ | Exp Mass (M + 1)+ |
|---|---|---|---|---|
| 81 | 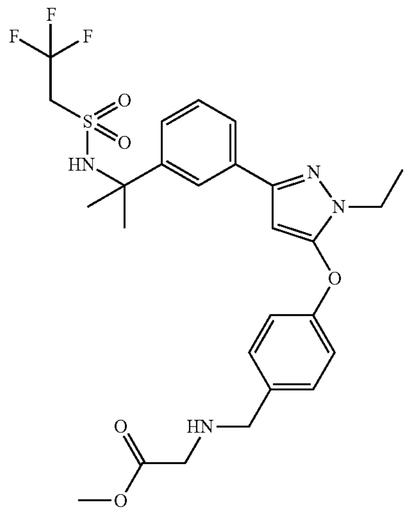 [SMILES: CCn1nc(-c2cccc(C(C)(C)NS(=O)(=O)CC(F)(F)F)c2)cc1Oc1ccc(CNCC(=O)OC)cc1] | methyl N-[4-({1-ethyl-3-[3-(1-methyl-1-{[(2,2,2-trifluoroethyl)sulfonyl]amino}ethyl)phenyl]-1H-pyrazol-5-yl}oxy)benzyl]glycinate | 569.2 | 569.1 |
| 82 | 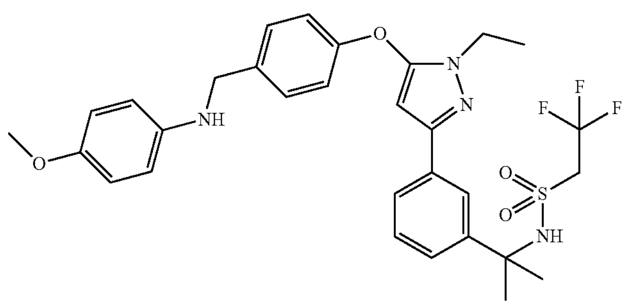 [SMILES: CCn1nc(-c2cccc(C(C)(C)NS(=O)(=O)CC(F)(F)F)c2)cc1Oc1ccc(CNc2ccc(OC)cc2)cc1] | N-(1-{3-[1-ethyl-5-(4-{[(4-methoxyphenyl)amino]methyl}phenoxy)-1H-pyrazol-3-yl]phenyl}-1-methoxyethyl)-2,2,2-trifluoroethanesulfonamide | 603.2 | 603.1 |
| 83 | 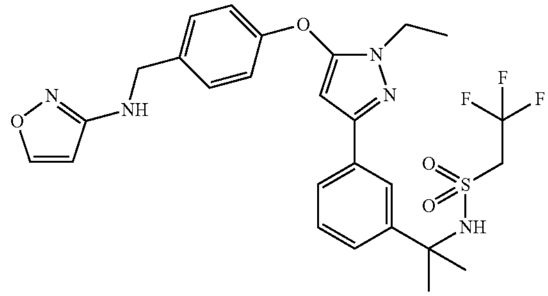 [SMILES: CCn1nc(-c2cccc(C(C)(C)NS(=O)(=O)CC(F)(F)F)c2)cc1Oc1ccc(CNc2ccon2)cc1] | N-{1-[3-(1-ethyl-5-{4-[(isoxazol-3-ylamino)methyl]phenoxy}-1H-pyrazol-3-yl)phenyl]-1-methylethyl}-2,2,2-trifluoroethanesulfonamide | 564.2 | 564.1 |
| 84 | 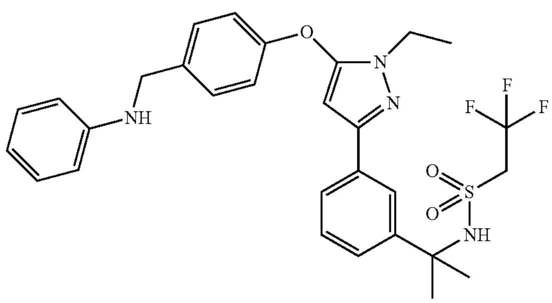 [SMILES: CCn1nc(-c2cccc(C(C)(C)NS(=O)(=O)CC(F)(F)F)c2)cc1Oc1ccc(CNc2ccccc2)cc1] | N-[1-(3-{5-[4-(anilinomethyl)phenoxy]-1-ethyl-1H-pyrazol-3-yl}phenyl)-1-methylethyl]-2,2,2-trifluoroethanesulfonamide | 573.2 | 573.1 |

| # | Structure | Name | Calc Mass (M + 1)+ | Exp Mass (M + 1)+ |
|---|---|---|---|---|
| 85 | 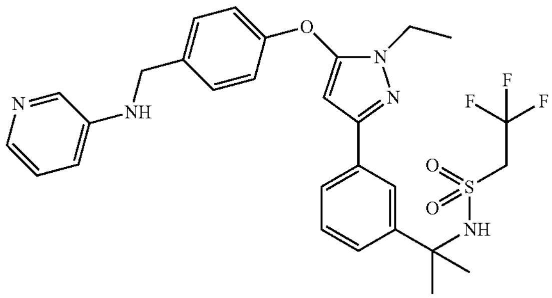 [SMILES: CCn1nc(-c2cccc(C(C)(C)NS(=O)(=O)CC(F)(F)F)c2)cc1Oc1ccc(CNc2cccnc2)cc1] | N-{1-[3-(1-ethyl-5-{4-[(pyridin-3-ylamino)methyl]phenoxy}-1H-pyrazol-3-yl)phenyl]-1-methylethyl}-2,2,2-trifluoroethanesulfonamide | 574.2 | 574.1 |
| 86 | 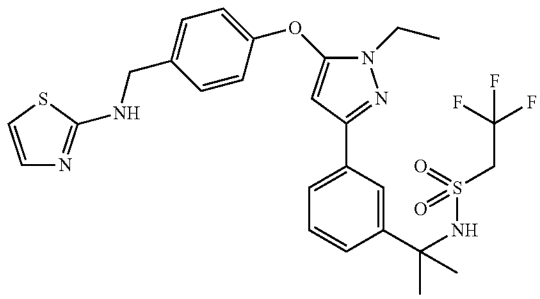 [SMILES: CCn1nc(-c2cccc(C(C)(C)NS(=O)(=O)CC(F)(F)F)c2)cc1Oc1ccc(CNc2nccs2)cc1] | N-{1-[3-(1-ethyl-5-{4-[(1,3-thiazol-2-ylamino)methyl]phenoxy}-1H-pyrazol-3-yl)phenyl]-1-methylethyl}-2,2,2-trifluoroethanesulfonamide | 580.2 | 580.1 |
| 87 | 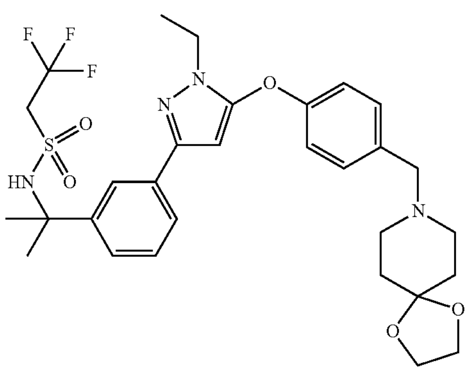 [SMILES: CCn1nc(-c2cccc(C(C)(C)NS(=O)(=O)CC(F)(F)F)c2)cc1Oc1ccc(CN2CCC3(CC2)OCCO3)cc1] | N-[1-(3-{5-[4-(1,4-dioxa-8-azaspiro[4.5]dec-8-ylmethyl)phenoxy]-1-ethyl-1H-pyrazol-3-yl}phenyl)-1-methylethyl]-2,2,2-trifluoroethanesulfonamide | 623.3 | 623.2 |
| 88 | 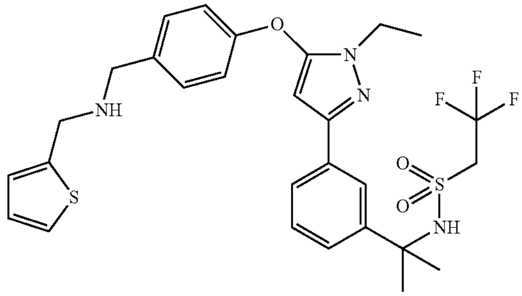 [SMILES: CCn1nc(-c2cccc(C(C)(C)NS(=O)(=O)CC(F)(F)F)c2)cc1Oc1ccc(CNCc2cccs2)cc1] | N-(1-{3-[1-ethyl-5-(4-{[(2-thienylmethyl)amino]methyl}phenoxy)-1H-pyrazol-3-yl]phenyl}-1-methylethyl)-2,2,2-trifluoroethanesulfonamide | 593.2 | 593.1 |

-continued

| # | Structure | Name | Calc Mass (M + 1)⁺ | Exp Mass (M + 1)⁺ |
|---|---|---|---|---|
| 89 | 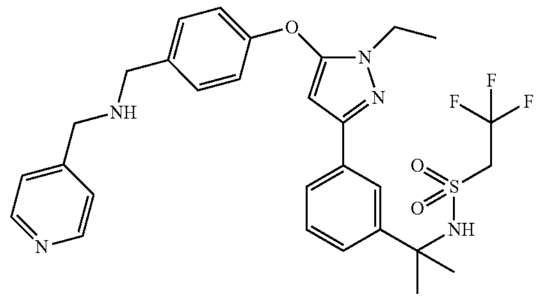 [SMILES: CCn1nc(-c2cccc(C(C)(C)NS(=O)(=O)CC(F)(F)F)c2)cc1Oc1ccc(CNCc2ccncc2)cc1] | N-(1-{3-[1-ethyl-5-(4-{[(pyridin-4-ylmethyl)amino]methyl}phenoxy)-1H-pyrazol-3-yl]phenyl}-1-methylethyl)-2,2,2-trifluoroethanesulfonamide | 588.2 | 588.1 |
| 90 | 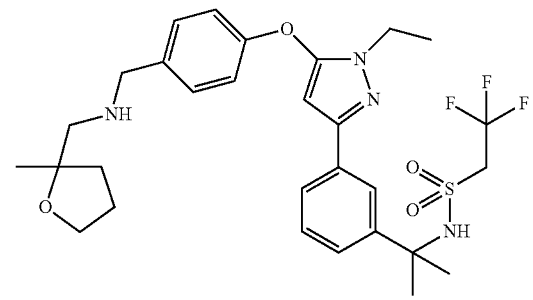 [SMILES: CCn1nc(-c2cccc(C(C)(C)NS(=O)(=O)CC(F)(F)F)c2)cc1Oc1ccc(CNCC2(C)CCCO2)cc1] | N-[1-(3-{1-ethyl-5-[4-({[(2-methyltetrahydrofuran-2-yl)methyl]amino}methyl)phenoxy]-1H-pyrazol-3-yl}phenyl)-1-methylethyl]-2,2,2-trifluoroethanesulfonamide | 595.3 | 595.1 |
| 91 | 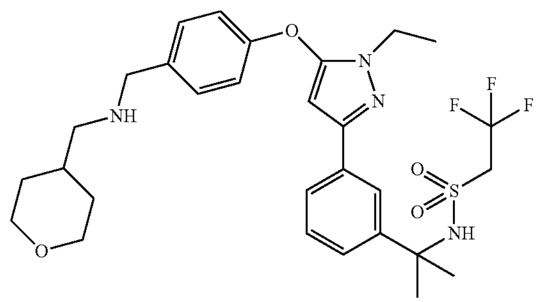 [SMILES: CCn1nc(-c2cccc(C(C)(C)NS(=O)(=O)CC(F)(F)F)c2)cc1Oc1ccc(CNCC2CCOCC2)cc1] | N-(1-{3-[1-ethyl-5-(4-{[(tetrahydro-2H-pyran-4-ylmethyl)amino]methyl}phenoxy)-1H-pyrazol-3-yl]phenyl}-1-methylethyl)-2,2,2-trifluoroethanesulfonamide | 595.3 | 595.5 |
| 92 | 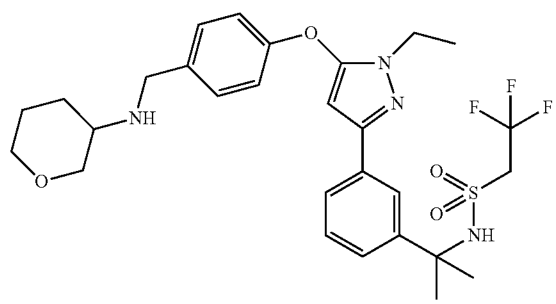 [SMILES: CCn1nc(-c2cccc(C(C)(C)NS(=O)(=O)CC(F)(F)F)c2)cc1Oc1ccc(CNC2CCCOC2)cc1] | N-{1-[3-(1-ethyl-5-{4-[(tetrahydro-2H-pyran-3-ylamino)methyl]phenoxy}-1H-pyrazol-3-yl)phenyl]-1-methylethyl}-2,2,2-trifluoroethanesulfonamide | 581.2 | 581.1 |
| 93 | 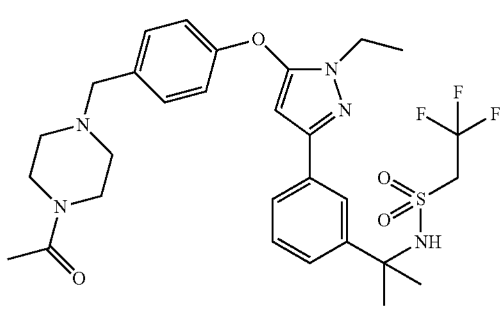 [SMILES: CCn1nc(-c2cccc(C(C)(C)NS(=O)(=O)CC(F)(F)F)c2)cc1Oc1ccc(CN2CCN(C(C)=O)CC2)cc1] | N-{1-[3-(5-{4-[(4-acetylpiperazin-1-yl)methyl]phenoxy}-1-ethyl-1H-pyrazol-3-yl)phenyl]-1-methylethyl}-2,2,2-trifluoroethanesulfonamide | 608.3 | 608.1 |

| # | Structure | Name | Calc Mass (M + 1)+ | Exp Mass (M + 1)+ |
|---|---|---|---|---|
| 94 | 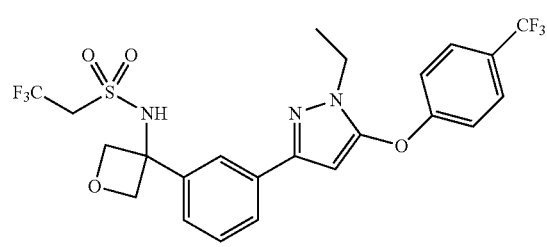 [SMILES: CCn1nc(-c2cccc(C3(NS(=O)(=O)CC(F)(F)F)COC3)c2)cc1Oc1ccc(C(F)(F)F)cc1] | N-(1-{3-[1-ethyl-5-(4-{[(pyridin-3-ylmethyl)amino]methyl}phenoxy)-1H-pyrazol-3-yl]phenyl}-1-methylethyl)-2,2,2-trifluoroethanesulfonamide | 588.2 | 588.1 |

Example 95

N-[3-(3-{1-ethyl-5-[4-(trifluoromethyl)phenoxy]-1H-pyrazol-3-yl}phenyl)oxetan-3-yl]-2,2,2-trifluoro-ethanesulfonamide Step 1:

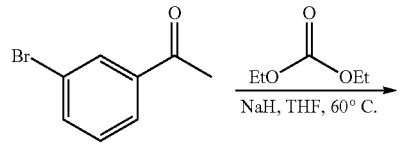

Ethyl 3-(3-bromophenyl)-3-oxopropanoate was prepared from 1-(3-bromophenyl)ethanone with a procedure similar to that used in Example 1, Step 1. Calc'd (M+1)+: 271.0. Found: 271.0.

Step 2:

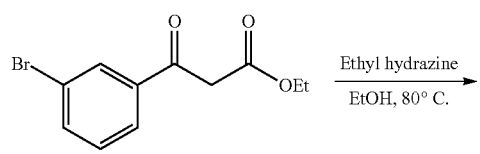

5-(3-bromophenyl)-2-ethyl-1,2-dihydro-3H-pyrazol-3-one was prepared from Ethyl 3-(3-bromophenyl)-3-oxopropanoate with a procedure similar to that used in Example 1, Step 2. Calc'd (M+1)+: 267.0. Found: 266.9.

Step 3:

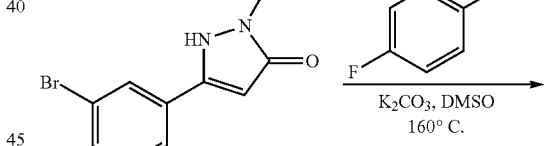

3-(3-bromophenyl)-1-ethyl-5-[4-(trifluoromethyl)phenoxy]-1H-pyrazole was prepared from 5-(3-bromophenyl)-2-ethyl-1,2-dihydro-3H-pyrazol-3-one with a procedure similar to that used in Example 1, Step 3. Calc'd (M+1)+: 411.0. Found: 411.0.

Step 4:

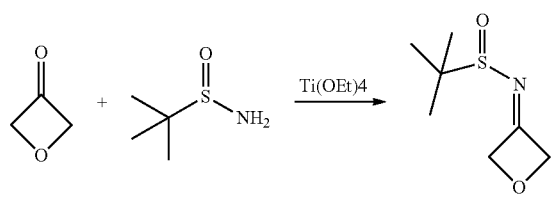

Titanium (IV) ethoxide (0.25 mL, 1.2 mmol, 2.0 equiv) was added to a solution of oxetane-3-one (43 mg, 0.59 mmol, 1 equiv) and 2-methylpropane-2-sulfinamide (72 mg, 0.59 mmol, 1 equiv) in tetrahydrofuran (1.1 mL) at 22° C. The reaction mixture was heated to 50° C. for 16 hours, then was cooled to 22° C. and poured over stirring saturated aqueous sodium chloride solution (3 mL). The suspension was filtered through celite with the aid of ethyl acetate, and the filtrate was partitioned between ethyl acetate and saturated aqueous sodium chloride solution. The organic layer was dried over sodium sulfate, and the dried solution was filtered. The filtrate was concentrated to give 2-methyl-N-oxetan-3-ylidenepropane-2-sulfinamide (43 mg, 43%) as a light-yellow oil. Calc'd (M+1)+: 176.1. Found: 176.1.

Step 5:

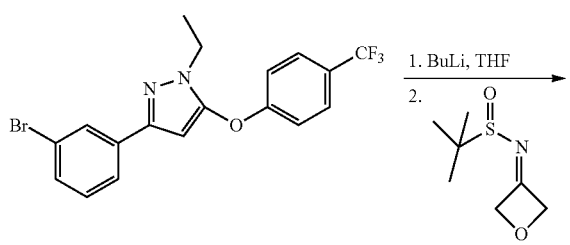

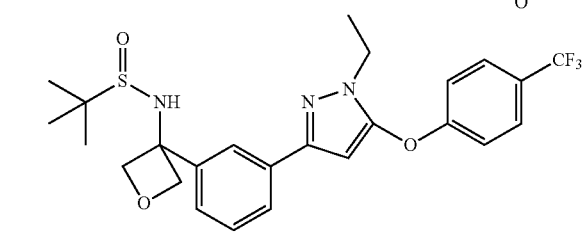

A solution of n-butyllithium in hexanes (2.50 M, 1.3 mL, 3.2 mmol, 1.5 equiv) was added to a solution of -(3-bromophenyl)-1-ethyl-5-[4-(trifluoromethyl)phenoxy]-1H-pyrazole (1.32 g, 3.21 mmol, 1.5 equiv) in tetrahydrofuran (18 mL) at −78° C. The reaction mixture was stirred at −78° C. for 20 minutes, and then a solution of 2-methyl-N-oxetan-3-ylidenepropane-2-sulfinamide (375 mg, 2.14 mmol, 1 equiv) in tetrahydrofuran (2 mL) was added via syringe. The reaction mixture was stirred at −78° C. for 5 minutes, then the cooling bath was removed. After stirring for an additional 15 minutes, saturated aqueous ammonium chloride solution was added, and the crude product was partitioned between ethyl acetate and water. The organic layer was washed with saturated aqueous sodium chloride solution, and the washed solution was dried over sodium sulfate. The dried solution was filtered, and the filtrate was concentrated. The residue was purified by flash-column chromatography (10% ethyl acetate-hexanes, grading to 100% ethyl acetate, then flushing with 10% methanol-dichloromethane) to afford N-[3-(3-{1-ethyl-5-[4-(trifluoromethyl)phenoxy]-1H-pyrazol-3-yl}phenyl)oxetan-3-yl]-2-methylpropane-2-sulfinamide (894 mg, 82%). Calc'd (M+1)+: 508.2. Found: 507.9.

Step 6:

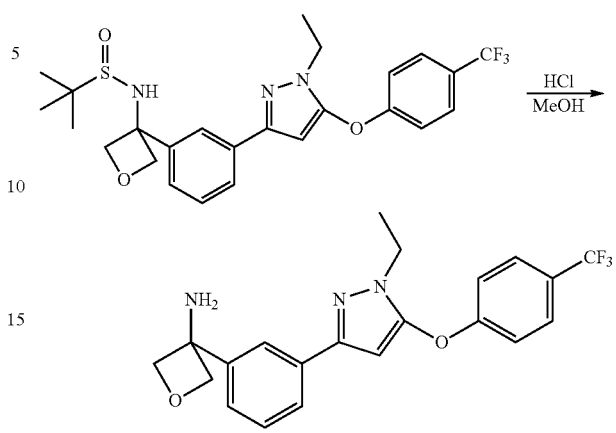

A solution of hydrochloric acid in dioxane (4 M, 1.55 mL, 6.2 mmol, 4.0 equiv) was added to a solution of N-[3-(3-{1-ethyl-5-[4-(trifluoromethyl)phenoxy]-1H-pyrazol-3-yl}phenyl)oxetan-3-yl]-2-methylpropane-2-sulfinamide (785 mg, 1.55 mmol, 1 equiv) in methanol (3.5 mL) at 22° C. The reaction mixture was stirred for 15 minutes, then was partitioned between ethyl acetate and saturated aqueous sodium bicarbonate solution. The organic layer was washed with saturated aqueous sodium chloride solution, and the washed solution was dried over sodium sulfate. The dried solution was filtered, and the filtrate was concentrated to afford 3-(3-{1-ethyl-5-[4-(trifluoromethyl)phenoxy]-1H-pyrazol-3-yl}phenyl)oxetan-3-amine, which was used in the next step without further purification. Calc'd (M+1)+: 404.2. Found: 404.1.

Step 7:

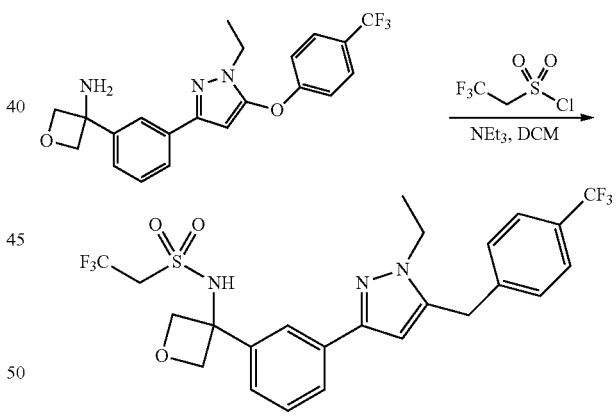

N-[3-(3-{1-ethyl-5-[4-(trifluoromethyl)phenoxy]-1H-pyrazol-3-yl}phenyl)oxetan-3-yl]-2,2,2-trifluoroethanesulfonamide was prepared from 3-(3-{1-ethyl-5-[4-(trifluoromethyl)phenoxy]-1H-pyrazol-3-yl}phenyl)oxetan-3-amine with a procedure similar to that used in Example 1, Step 5. Calc'd (M+1)+: 550.1. Found: 549.9.

$^1$H NMR (600 MHz, cdcl3) δ 7.82-7.77 (m, 2H), 7.66 (d, J=8.7, 2H), 7.50 (t, J=8.0, 1H), 7.35 (d, J=7.8, 1H), 7.23 (d, J=8.6, 2H), 6.05 (s, 1H), 5.73 (s, 1H), 5.16 (d, J=7.2, 2H), 5.04 (d, J=7.2, 2H), 4.13 (q, J=7.3, 2H), 3.02 (q, J=8.7, 2H), 1.47 (t, J=7.3, 3H).

The following compounds were prepared from N-[3-(3-{1-ethyl-5-[4-(trifluoromethyl)phenoxy]-1H-pyrazol-3-yl}phenyl)oxetan-3-yl]-2,2,2-trifluoroethanesulfonamide with similar procedures, varying the sulfonyl/sulfonyl chloride used.

| # | Structure | Name | Calc Mass (M + 1)+ | Exp Mass (M + 1)+ |
| --- | --- | --- | --- | --- |
| 96 | 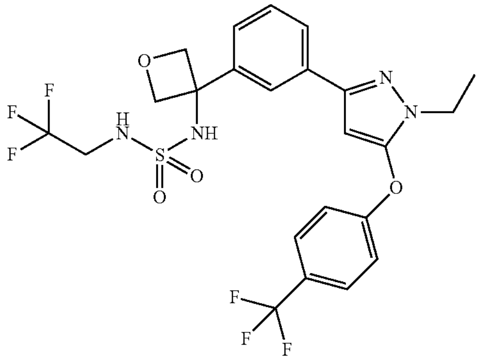 [SMILES: CCn1nc(-c2cccc(C3(NS(=O)(=O)NCC(F)(F)F)COC3)c2)cc1Oc1ccc(C(F)(F)F)cc1] | N-[3-(3-{1-ethyl-5-[4-(trifluoromethyl)phenoxy]-1H-pyrazol-3-yl}phenyl)oxetan-3-yl]-N'-(2,2,2-trifluoroethyl)sulfamide | 565.1 | 565.0 |
| 97 | 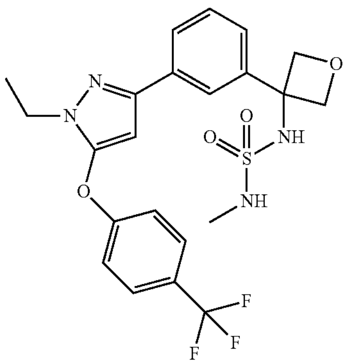 [SMILES: CCn1nc(-c2cccc(C3(NS(=O)(=O)NC)COC3)c2)cc1Oc1ccc(C(F)(F)F)cc1] | N-[3-(3-{1-ethyl-5-[4-(trifluoromethyl)phenoxy]-1H-pyrazol-3-yl}phenyl)oxetan-3-yl]-N'-methylsulfamide | 497.1 | 497.0 |
| 98 | 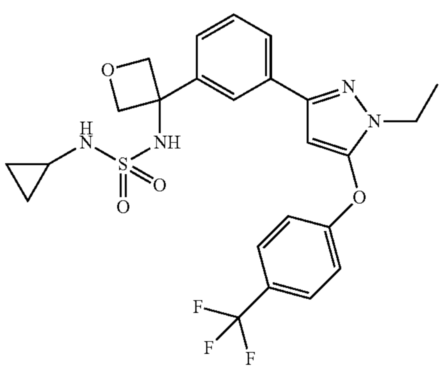 [SMILES: CCn1nc(-c2cccc(C3(NS(=O)(=O)NC4CC4)COC3)c2)cc1Oc1ccc(C(F)(F)F)cc1] | N-cyclopropyl-N-[3-(3-{1-ethyl-5-[4-(trifluoromethyl)phenoxy]-1H-pyrazol-3-yl}phenyl)oxetan-3-yl]sulfamide | 523.2 | 523.1 |
| 99 | 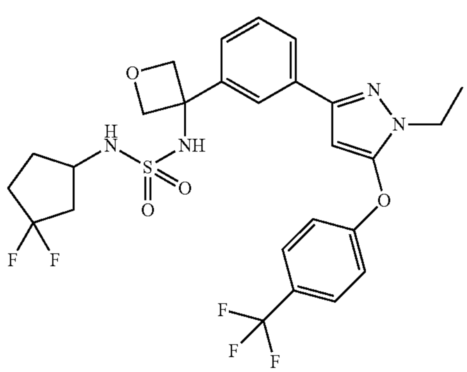 [SMILES: CCn1nc(-c2cccc(C3(NS(=O)(=O)NC4CCC(F)(F)C4)COC3)c2)cc1Oc1ccc(C(F)(F)F)cc1] | N-(3,3-difluorocyclopentyl)-N-[3-(3-{1-ethyl-5-[4-(trifluoromethyl)phenoxy]-1H-pyrazol-3-yl}phenyl)oxetan-3-yl]sulfamide | 587.6 | 587.5 |

Example 100

N-[3-(3-{1-ethyl-3-[4-(trifluoromethyl)phenoxy]-1H-pyrazol-5-yl}phenyl)oxetan-3-yl]-2,2,2-trifluoro-ethanesulfonamide

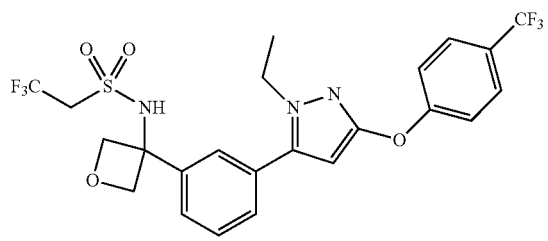

Step 1:

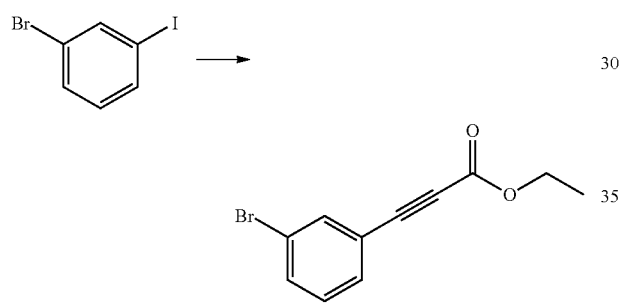

Ethyl propiolate (2.15 mL, 21.2 mmol, 1.20 equiv) was added to a mixture of 1-bromo-3-iodobenzene (5.00 g, 17.7 mmol, 1 equiv), $PdCl_2(CH_3CN)_2$ (367 mg, 1.41 mmol, 0.080 equiv), copper (I) iodide (135 mg, 0.707 mmol, 0.040 equiv) and potassium carbonate (2.93 g, 21.2 mmol, 1.20 equiv) in N,N-dimethylformamide (44 mL) at 22° C. The reaction mixture was stirred for 1 hour, then was partitioned between ethyl acetate and saturated aqueous ammonium chloride solution. The organic layer was washed sequentially with water and saturated aqueous sodium chloride solution. The washed solution was dried over sodium sulfate, and the dried solution was filtered. The filtrate was concentrated, and the residue was purified by flash-column chromatography on silica gel (hexanes, grading to 40% ethyl acetate-hexanes) to afford ethyl 3-(3-bromophenyl)prop-2-ynoate (1.08 g, 24%). Calc'd (M+1)$^+$: 253.0. Found: 252.9.

Step 2:

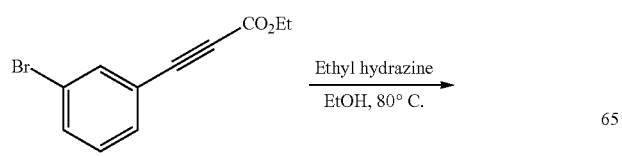

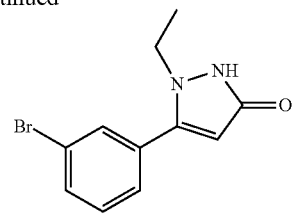

5-(3-bromophenyl)-1-ethyl-1,2-dihydro-3H-pyrazol-3-one was prepared from ethyl 3-(3-bromophenyl)prop-2-ynoate with a procedure similar to that used for Example 16 Step 2. Calc'd (M+1)$^+$: 267.0. Found: 266.9.

Step 3:

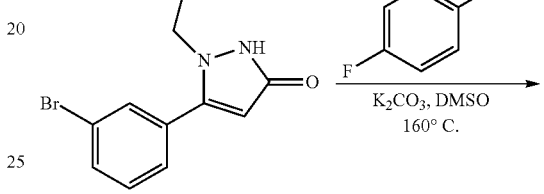

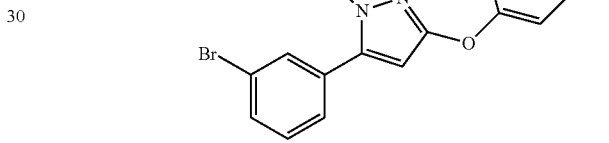

5-(3-bromophenyl)-1-ethyl-3-[4-(trifluoromethyl)phenoxy]-1H-pyrazole was prepared from 5-(3-bromophenyl)-1-ethyl-1,2-dihydro-3H-pyrazol-3-one with a procedure similar to that used for Example 16, Step 3. Calc'd (M+1)$^+$: 411.0. Found: 410.9.

Step 4:

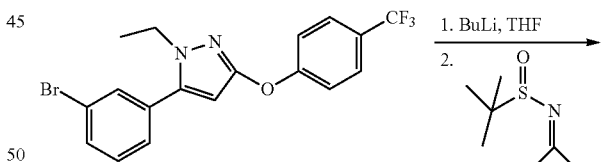

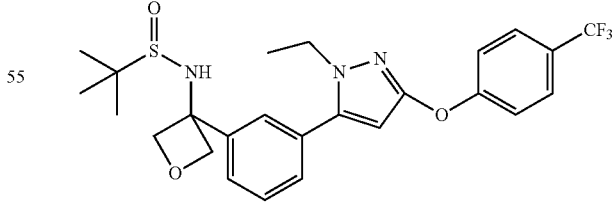

N-[3-(3-{1-ethyl-3-[4-(trifluoromethyl)phenoxy]-1H-pyrazol-5-yl}phenyl)oxetan-3-yl]-2-methylpropane-2-sulfinamide was prepared from 5-(3-bromophenyl)-1-ethyl-3-[4-(trifluoromethyl)phenoxy]-1H-pyrazole with a sequence similar to that used for Example 95, Step 5. Calc'd (M+1)$^+$: 508.2. Found: 508.1.

Step 5:

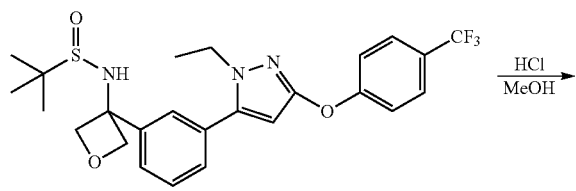

3-(3-{1-ethyl-3-[4-(trifluoromethyl)phenoxy]-1H-pyrazol-5-yl}phenyl)oxetan-3-amine was prepared from N-[3-(3-{1-ethyl-3-[4-(trifluoromethyl)phenoxy]-1H-pyrazol-5-yl}phenyl)oxetan-3-yl]-2-methylpropane-2-sulfinamide with a procedure similar to that used for Example 95, Step 6. Calc'd (M+1)$^+$: 404.2. Found: 404.0.

Step 6:

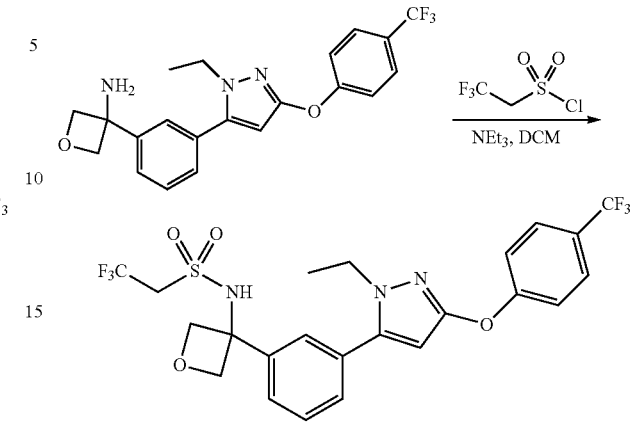

N-[3-(3-{1-ethyl-3-[4-(trifluoromethyl)phenoxy]-1H-pyrazol-5-yl}phenyl)oxetan-3-yl]-2,2,2-trifluoroethanesulfonamide was prepared from 3-(3-{1-ethyl-3-[4-(trifluoromethyl)phenoxy]-1H-pyrazol-5-yl}phenyl)oxetan-3-amine with a procedure similar to that used for Example 95, Step 7. Calc'd (M+1)$^+$: 550.1. Found: 550.0.

| # | Structure | Name | Calc Mass (M + 1)$^+$ | Exp Mass (M + 1)$^+$ |
|---|---|---|---|---|
| 101 | 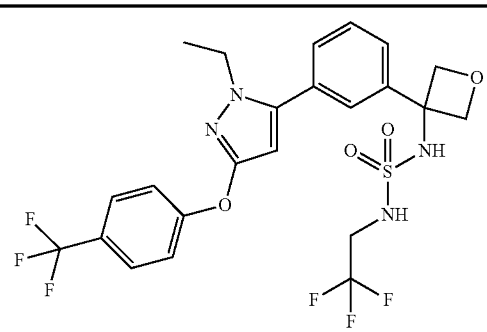 | N-[3-(3-{1-ethyl-3-[4-(trifluoromethyl)phenoxy]-1H-pyrazol-5-yl}phenyl)oxetan-3-yl]-N'-(2,2,2-trifluoroethyl)sulfamide | 565.1 | 565.0 |
| 102 | 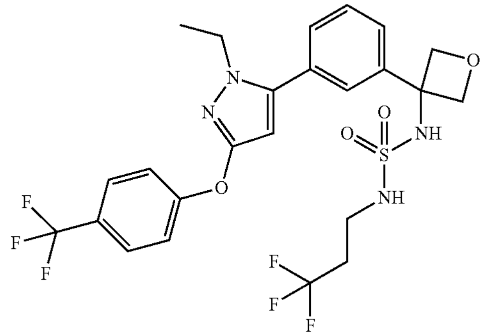 [SMILES: CCn1nc(Oc2ccc(C(F)(F)F)cc2)cc1-c1cccc(C2(NS(=O)(=O)NCCC(F)(F)F)COC2)c1] | N-[3-(3-{1-ethyl-3-[4-(trifluoromethyl)phenoxy]-1H-pyrazol-5-yl}phenyl)oxetan-3-yl]-N'-(2,2,2-trifluoropropyl)sulfamide | 579.6 | 579.5 |

| # | Structure | Name | Calc Mass (M + 1)+ | Exp Mass (M + 1)+ |
|---|---|---|---|---|
| 103 | 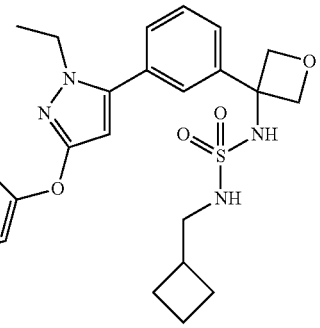 | N-(cyclobutylmethyl)-N-[3-(3-{1-ethyl-3-[4-(trifluoromethyl)phenoxy]-1H-pyrazol-5-yl}phenyl)oxetan-3-yl]sulfamide | 551.6 | 551.5 |
| 104 | 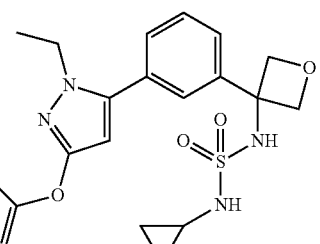 | N-cyclopropyl-N-[3-(3-{1-ethyl-3-[4-(trifluoromethyl)phenoxy]-1H-pyrazol-5-yl}phenyl)oxetan-3-yl]sulfamide | 523.2 | 523.2 |

The following examples were prepared by a similar route as Example 1 and Example 28, varying the alkylhydrazine used in Step 2 of Example 1:

| # | Structure | Name | Calc Mass (M + 1)+ | Exp Mass (M + 1)+ |
|---|---|---|---|---|
| 105 | 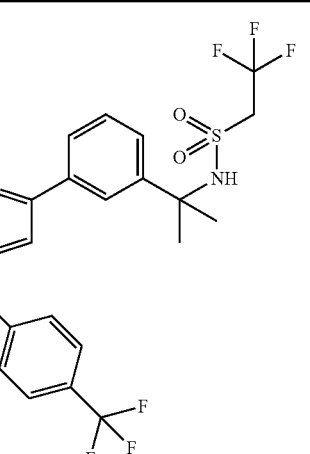 | 2,2,2-trifluoro-N-[1-(3-{1-(2-hydroxyethyl)-5-[4-(trifluoromethyl)phenoxy]-1H-pyrazol-3-yl}phenyl)-1-methylethyl]ethanesulfonamide | 552.1 | 552.0 |

| # | Structure | Name | Calc Mass (M + 1)+ | Exp Mass (M + 1)+ |
|---|-----------|------|--------------------|--------------------|
| 106 | 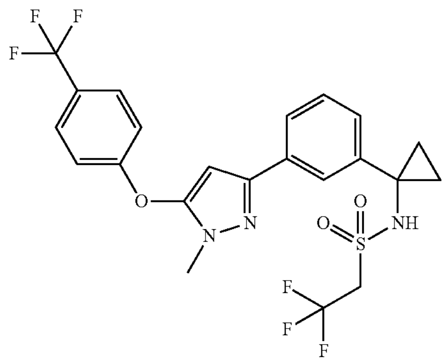 [SMILES: Cn1nc(-c2cccc(C3(NS(=O)(=O)CC(F)(F)F)CC3)c2)cc1Oc1ccc(C(F)(F)F)cc1] | 2,2,2-trifluoro-N-[1-(3-{1-methyl-5-[4-(trifluoromethyl)phenoxy]-1H-pyrazol-3-yl}phenyl)cyclopropyl]ethanesulfonamide | 520.1 | 520.2 |
| 107 | 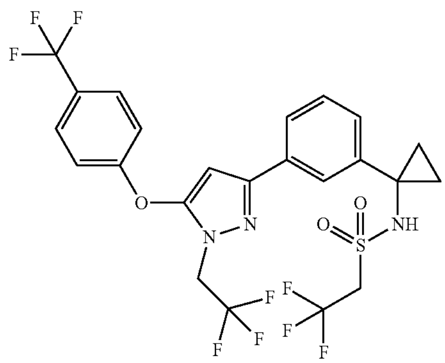 [SMILES: O=S(=O)(CC(F)(F)F)NC1(c2cccc(-c3cc(Oc4ccc(C(F)(F)F)cc4)n(CC(F)(F)F)n3)c2)CC1] | 2,2,2-trifluoro-N-[1-(3-{1-(2,2,2-trifluoroethyl)-5-[4-(trifluoromethyl)phenoxy]-1H-pyrazol-3-yl}phenyl)cyclopropyl]ethanesulfonamide | 588.1 | 588.1 |

Example 108

N-(1-{3-[5-(4-cyanophenoxy)-1-ethyl-1H-pyrazol-3-yl]phenyl}-1-methylethyl)-2,2,2-trifluoroethanesulfonamide Step 1:

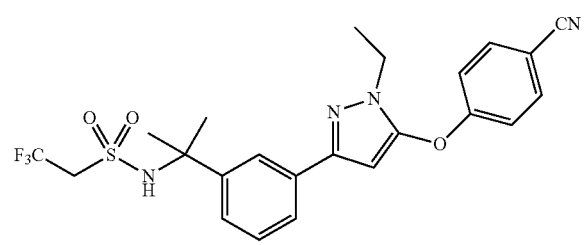 [SMILES: CCn1nc(-c2cccc(C(C)(C)NS(=O)(=O)CC(F)(F)F)c2)cc1Oc1ccc(C#N)cc1]

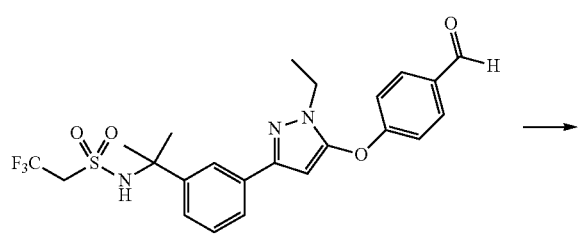

→

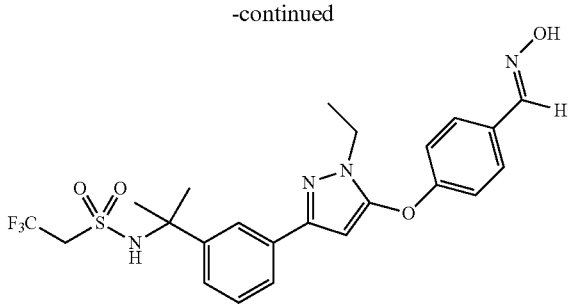

To a solution of N-(2-{3-[1-ethyl-5-(4-formylphenoxy)-1H-pyrazol-3-yl]phenyl}propan-2-yl)-2,2,2-trifluoroethanesulfonamine (0.51 g, 1.03 mmol) in methanol (5 ml) was added hydroxylamide hydrochloride (0.072 g, 1.04 mmol) and then pyridine (0.09 ml, 1.11 mmol). The reaction was allowed to heat at reflux and was complete within two hours and forty-five minutes. The cooled reaction was diluted with water and ethyl acetate. The layers were separated. The aqueous layer was extracted one time with ethyl acetate. The combined organic extracts were washed with brine. The organic extract was dried over sodium sulfate, filtered, and concentrated to yield N-(2-[3-(1-ethyl-5-{4-[(E/Z)-(hydroxylamine)methyl]phenoxy}-1H-pyrazol-3-yl)phenyl]propan-2-yl)-2,2,2-trifluoroethanesulfonamide Calc'd (M+1): 511. Found: 511.

Step 2:

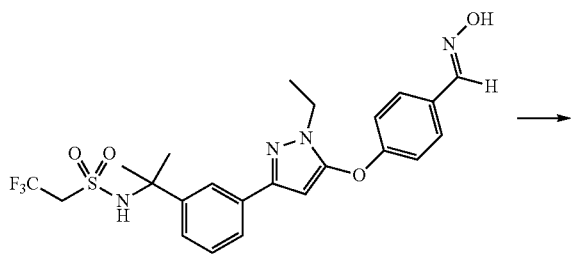

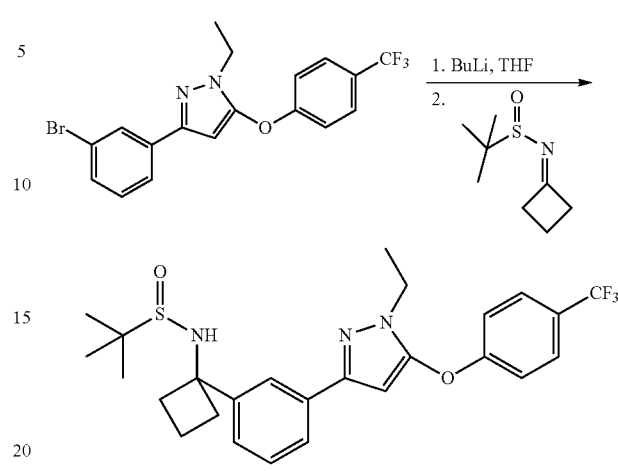

To a solution of N-(2-[3-(1-ethyl-5-{4-[(E/Z)-(hydroxylamine)methyl]phenoxy}-1H-pyrazol-3-yl)phenyl]propan-2-yl}-2,2,2-trifluoroethanesulfonamide (0.498 g, 0.98 mmol) in THF (5 ml) was added Burgess reagent (0.358 g, 1.46 mmol). The reaction was allowed to reflux for approximately three hours. The cooled reaction was absorbed onto silica and purified by column chromatography on silica gel, eluting with EtOAc/hexane to yield N-(2-{3-[5-4-cyanophenoxy)-1H-pyrazol-3-yl]phenyl}propan-2-yl)-2,2,2-trifluoroethane sulfonamide. Calc'd (M+1): 493. Found: 493.

Example 109

N-[1-(3-{1-ethyl-5-[4-(trifluoromethyl)phenoxy]-1H-pyrazol-3-yl}phenyl)cyclobutyl]-2,2,2-trifluoroethanesulfonamide

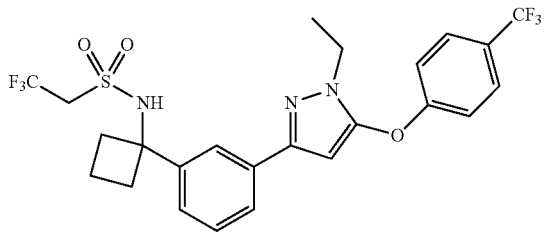 [SMILES: CCn1nc(-c2cccc(C3(NS(=O)(=O)CC(F)(F)F)CCC3)c2)cc1Oc1ccc(C(F)(F)F)cc1]

Step 1:

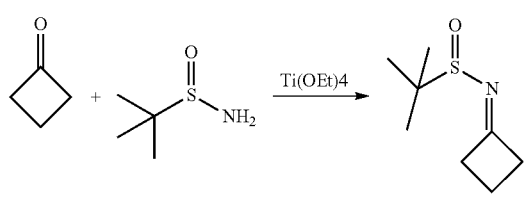

N-cyclobutylidene-2-methylpropane-2-sulfinamide was prepared from cyclobutanone with a procedure similar to that used for Example 95, Step 4. Calc'd (M+1)$^+$: 174.1. Found: 174.1.

N-[1-(3-{1-ethyl-5-[4-(trifluoromethyl)phenoxy]-1H-pyrazol-3-yl}phenyl)cyclobutyl]-2-methylpropane-2-sulfinamide was prepared from 3-(3-bromophenyl)-1-ethyl-5-[4-(trifluoromethyl)phenoxy]-1H-pyrazole with a procedure similar to that used for Example 95, Step 5. Calc'd (M+1)$^+$: 506.2. Found: 506.1.

Step 3:

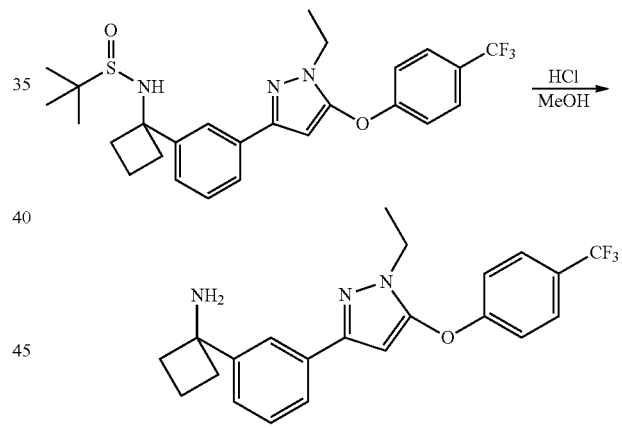

1-(3-{1-ethyl-5-[4-(trifluoromethyl)phenoxy]-1H-pyrazol-3-yl}phenyl)cyclobutanamine was prepared from N-[1-(3-{1-ethyl-5-[4-(trifluoromethyl)phenoxy]-1H-pyrazol-3-yl}phenyl)cyclobutyl]-2-methylpropane-2-sulfinamide with a procedure similar to that used for Example 95 Step 6. Calc'd (M+1)$^+$: 402.2. Found: 402.1.

Step 4:

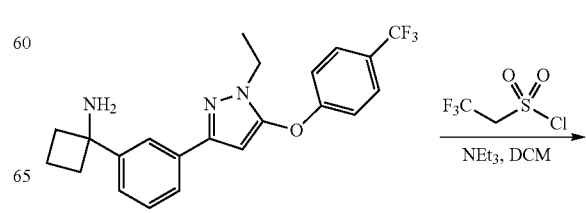

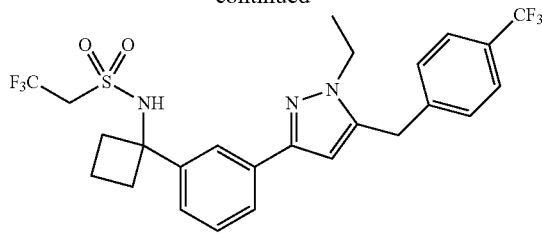

N-[1-(3-{1-ethyl-5-[4-(trifluoromethyl)phenoxy]-1H-pyrazol-3-yl}phenyl)cyclobutyl]-2,2,2-trifluoroethanesulfonamide was prepared from 1-(3-{1-ethyl-5-[4-(trifluoromethyl)phenoxy]-1H-pyrazol-3-yl}phenyl)cyclobutanamine with a procedure similar to that used for Example 95, Step 7. Calc'd (M+1)$^+$: 548.1. Found: 548.1.

Example 110

N-[1-(3-{1-ethyl-4-fluoro-3-[4-(trifluoromethyl)phenoxy]-1H-pyrazol-5-yl}phenyl)cyclopropyl]-2,2,2-trifluoroethanesulfonamide

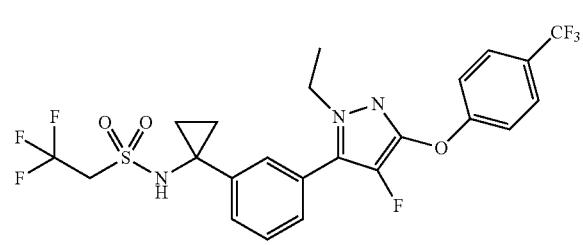

Step 1:

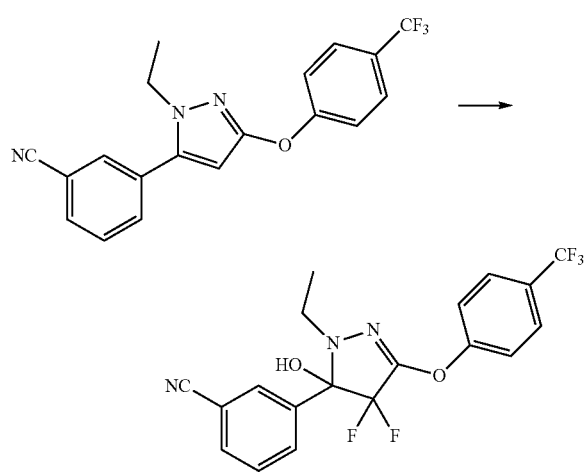

A mixture of 3-{1-ethyl-3-[4-(trifluoromethyl)phenoxy]-1H-pyrazol-5-yl}benzonitrile (2.00 g, 5.60 mmol) and selectfluor (9.91 g, 28.0 mmol) was taken into DMF (17.0 mL) and the suspension heated to 60° C. The reaction was followed by LCMS for 2 h. The reaction was cooled, diluted with EtOAc and washed with 50% saturated brine 3×, brine, dried (MgSO$_4$) and concentrated to afford 3-{1-ethyl-4,4-difluoro-5-hydroxy-3-[4-(trifluoromethyl)phenoxy]-4,5-dihydro-1H-pyrazol-5-yl}benzonitrile, used crude in the next reaction: MS: cal'd 412 (MH+), exp 412 (MH+).

Step 2:

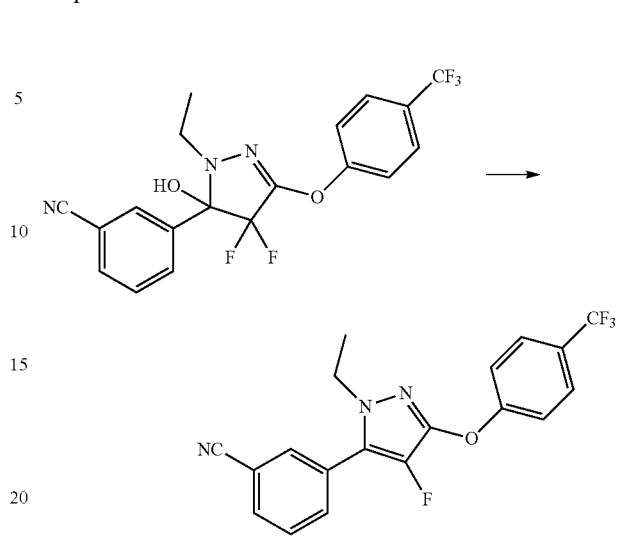

A solution of 3-{1-ethyl-4,4-difluoro-5-hydroxy-3-[4-(trifluoromethyl)phenoxy]-4,5-dihydro-1H-pyrazol-5-yl}benzonitrile (crude, 2.1 g, 5.11 mmol), DCM (25.5 mL) and triethylsilane (2.45 mL, 15.3 mmol) was cooled to −78° C. and treated with BF3 etherate (1.94 mL, 15.3 mmol) in a single portion. The reaction was allowed to warm to rt overnight and checked via LCMS at 16 h. The reaction was treated with DBU (3.85 mL, 25.6 mmol) dropwise and checked via LCMS after 30 minutes, requisite product dominates. The reaction was diluted with EtOAc and washed with sat aq. NaHCO$_3$ 2×, brine, dried (MgSO$_4$) and concentrated to afford an opaque brown residue purified via MPLC, 100 g silica, 5-35% EtOAc in heptanes to afford 3-{1-ethyl-4-fluoro-3-[4-(trifluoromethyl)phenoxy]-1H-pyrazol-5-yl}benzonitrile as a clear, colorless oil. MS: cal'd 376 (MH+), exp 376 (MH+).

Step 3:

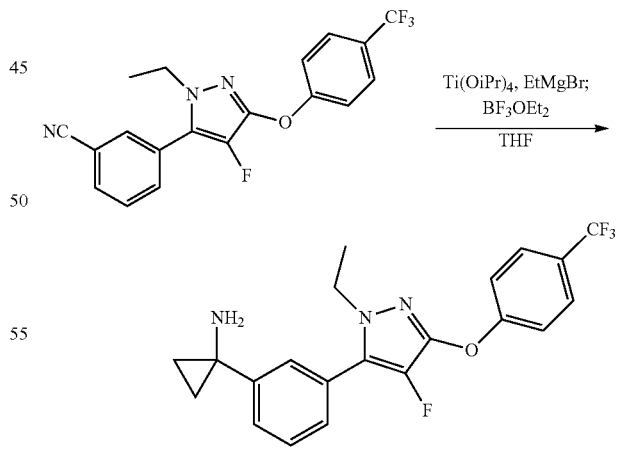

1-(3-{1-ethyl-4-fluoro-3-[4-(trifluoromethyl)phenoxy]-1H-pyrazol-5-yl}phenyl)cyclopropanamine was prepared from 3-{1-ethyl-4-fluoro-3-[4-(trifluoromethyl)phenoxy]-1H-pyrazol-5-yl}benzonitrile with a procedure similar to that used in Example 46, Step 1. MS: cal'd 406 (MH+), exp 406 (MH+).

Step 4:

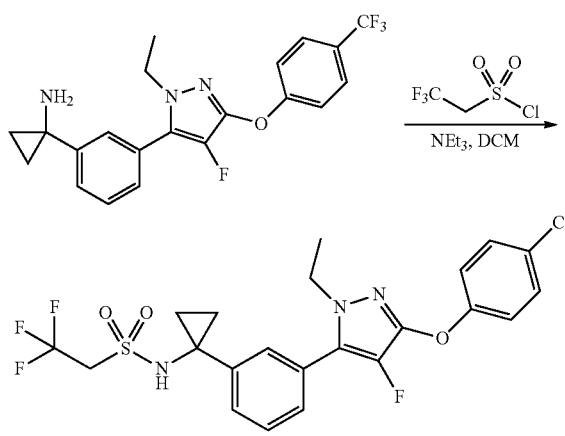

N-[1-(3-{1-ethyl-4-fluoro-3-[4-(trifluoromethyl)phenoxy]-1H-pyrazol-5-yl}phenyl)cyclopropyl]-2,2,2-trifluoroethanesulfonamide was prepared from 1-(3-{1-ethyl-4-fluoro-3-[4-(trifluoromethyl)phenoxy]-1H-pyrazol-5-yl}phenyl)cyclopropanamine with a procedure similar to that used in Example 46, Step 2. MS: cal'd 552 (MH+), exp 552 (MH+).

Example 111

N-[1-(3-{4-chloro-1-ethyl-5-[4-(trifluoromethyl)phenoxy]-1H-pyrazol-3-yl}phenyl)cyclopropyl]-2,2,2-trifluoroethanesulfonamide

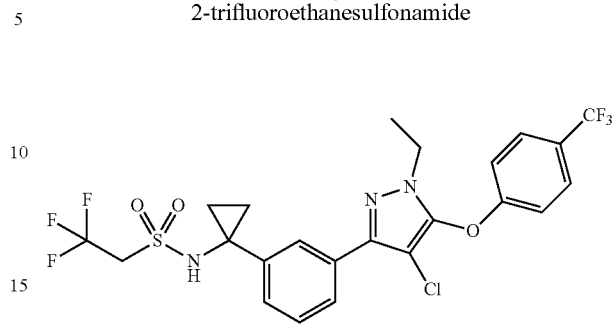

A solution of N-[1-(3-{1-ethyl-5-[4-(trifluoromethyl)phenoxy]-1H-pyrazol-3-yl}phenyl)cyclopropyl]-2,2,2-trifluoroethanesulfonamide (135 mg, 0.253 mmol) and chloroform (1.69 mL) was treated with NCS (43.9, 0.329 mmol), sealed in a vial and heated to 65° C. overnight. The reaction was cooled, diluted with EtOAc and washed with water, water spiked with a splash of sat. aq. NaHCO₃ 2×, brine, dried (MgSO₄) and concentrated to afford a clear light yellow oil purified via MPLC, 25 g silica, 5-50% EtOAc in heptanes affording a white solid: MS: cal'd 568 (MH+), exp 568 (MH+).

The following compounds were prepared by similar procedures, varying the compound subjected to NCS:

| # | Structure | Name | Calc Mass $(M+1)^+$ | Exp Mass $(M+1)^+$ |
|---|-----------|------|---------------------|--------------------|
| 112 | 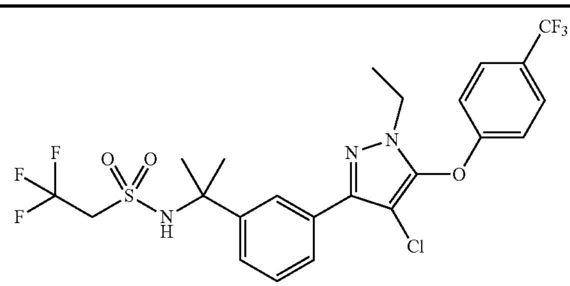 | N-[2-(3-{4-chloro-1-ethyl-5-[4-(trifluoromethyl)phenoxy]-1H-pyrazol-3-yl}phenyl)propan-2-yl]-2,2,2-trifluoroethanesulfonamide | 570 | 570 |
| 113 | 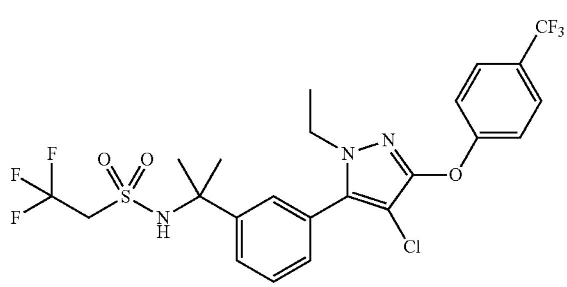 [SMILES: CCn1nc(Oc2ccc(C(F)(F)F)cc2)c(Cl)c1-c1cccc(C(C)(C)NS(=O)(=O)CC(F)(F)F)c1] | N-[2-(3-{4-chloro-1-ethyl-3-[4-(trifluoromethyl)phenoxy]-1H-pyrazol-5-yl}phenyl)propan-2-yl]-2,2,2-trifluoroethanesulfonamide | 570 | 570 |

Example 114

N-[2-(3-{4-Bromo-1-ethyl-3-[4-(trifluoromethyl)phenoxy]-1H-pyrazol-5-yl}phenyl)propan-2-yl]-2,2,2-trifluoroethanesulfonamide

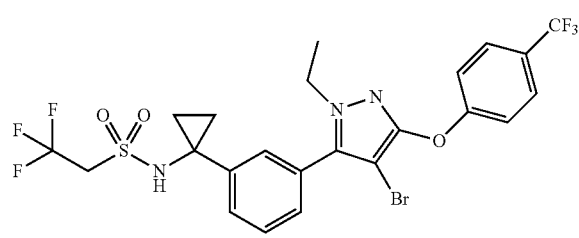

A solution of N-[2-(3-{1-ethyl-3-[4-(trifluoromethyl)phenoxy]-1H-pyrazol-5-yl}phenyl)propan-2-yl]-2,2,2-trifluoroethanesulfonamide (20 mg, 0.037 mmol) and DCM (0.25 mL) was cooled to 0° C. and treated with NBS (8.0 mg, 0.045 mmol). After 30 minutes the reaction was diluted with water and extracted with DCM 2×. The combined organic layers were dried (MgSO$_4$), concentrated to afford a clear, colorless residue purified via MPLC, 10 g silica, 5-40% EtOAc in heptanes to afford a clear, colorless residue: MS: car'd 614 and 616 (MH+), exp 614 and 616 (MH+).

The following compound was prepared by similar procedures, varying the compound subjected to NBS:

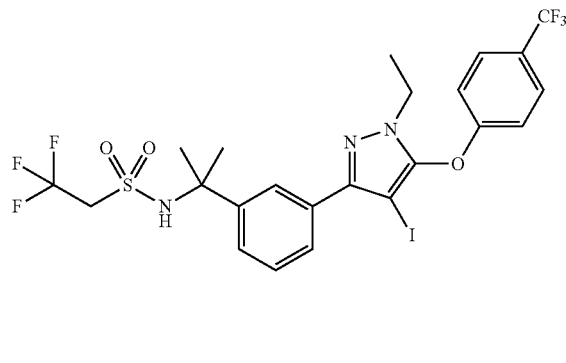

A solution of N-[2-(3-{1-ethyl-5-[4-(trifluoromethyl)phenoxy]-1H-pyrazol-3-yl}phenyl)propan-2-yl]-2,2,2-trifluoroethanesulfonamide (560 mg, 10.5 mmol) and DCM (6.97 mL) was cooled to 0° C., treated with NIS (706 mg, 3.14 mmol) in a single portion. The mixture was protected from light and allowed to warm to rt as it was stirred overnight. The reaction was diluted with EtOAc and washed with water 2×, sat. aq. NaHCO$_3$, brine, dried (MgSO$_4$) and concentrated to

| # | Structure | Name | Calc Mass (M + 1)$^+$ | Exp Mass (M + 1)$^+$ |
|---|-----------|------|------|------|
| 115 | 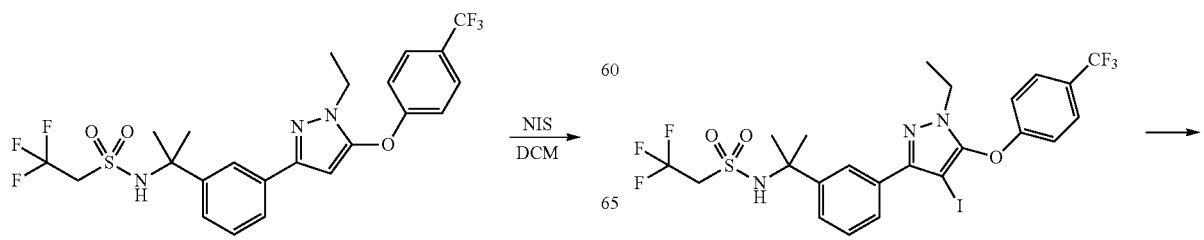 | N-[2-(3-{4-bromo-1-ethyl-5-[4-(trifluoromethyl)phenoxy]-1H-pyrazol-3-yl}phenyl)propan-2-yl]-2,2,2-trifluoroethanesulfonamide | 614 | 614 |

Example 116

N-[2-(3-{1-ethyl-4-iodo-5-[4-(trifluoromethyl)phenoxy]-1H-pyrazol-3-yl}phenyl)propan-2-yl]-2,2,2-trifluoroethanesulfonamide afford a white solid purified via MPLC, 25 g silica, 10-60% EtOAc in heptanes to afford a white solid: MS: cal'd 662 (MH+), exp 662 (MH+).

Example 117

N-[2-(3-{4-cyano-1-ethyl-5-[4-(trifluoromethyl)phenoxy]-1H-pyrazol-3-yl}phenyl)propan-2-yl]-2,2,2-trifluoroethanesulfonamide

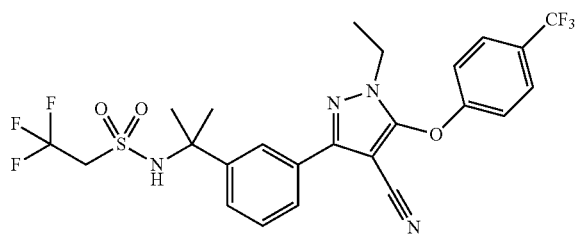

A suspension of N-[2-(3-{1-ethyl-4-iodo-5-[4-(trifluoromethyl)phenoxy]-1H-pyrazol-3-yl}phenyl)propan-2-yl]-2,2,2-trifluoroethanesulfonamide (538 mg, 0.813 mmol), copper (I) cyanide (729 mg, 8.13 mmol) and DMA (0.813 mL) was heated to 150° C. for 16 h. The reaction was cooled, partitioned between EtOAc and sat aq NaHCO₃, and filtered. The organic layer was washed with sat aq. NaHCO₃ 2×, dried (MgSO₄) and concentrated to afford a light yellow purified twice via MPLC, 50 g silica, 10-50% EtOAc in heptanes to afford 146 mg of a white solid: MS: cal'd 561 (MH+), exp 561 (MH+).

Example 118

N-[2-(3-{1-ethyl-4-formyl-5-[4-(trifluoromethyl)phenoxy]-1H-pyrazol-3-yl}phenyl)propan-2-yl]-2,2,2-trifluoroethanesulfonamide

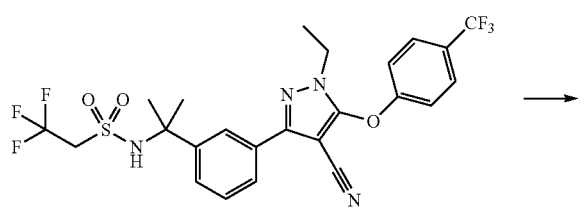

A solution of N-[2-(3-{4-cyano-1-ethyl-5-[4-(trifluoromethyl)phenoxy]-1H-pyrazol-3-yl}phenyl)propan-2-yl]-2,2,2-trifluoroethanesulfonamide (20.3 mg, 0.036 mmol) and DCM (0.362 mL) under nitrogen was cooled to 0° C. and treated with DIBAL (91 µL, 0.091 mmol, 1M in hexanes) dropwise. After 1.5 h the reaction was quenched with 1M aq. HCl and extracted with DCM 2×. The combined organic layers were dried (MgSO₄) and concentrated to afford a clear, colorless residue purified via MPLC, 5-60% EtOAc in heptanes to afford a clear, colorless residue: MS: cal'd 564 (MH+), exp 564 (MH+).

Example 119

N-[2-(3-{1-ethyl-4-(phenylethynyl)-5-[4-(trifluoromethyl)phenoxy]-1H-pyrazol-3-yl}phenyl)propan-2-yl]-2,2,2-trifluoroethanesulfonamide

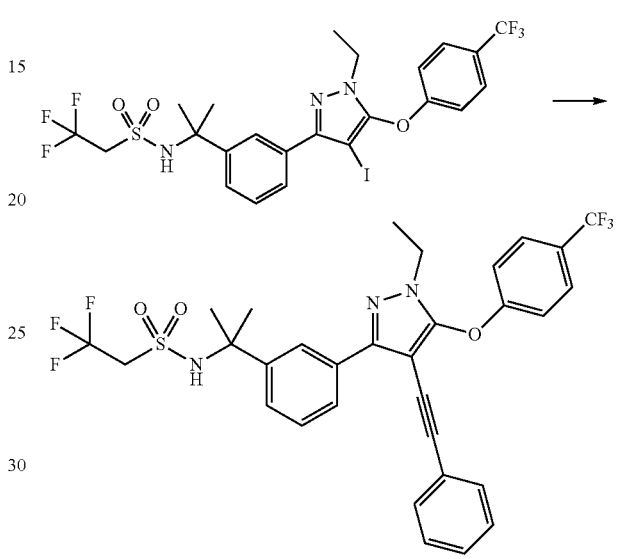

A solution of N-[2-(3-{1-ethyl-4-iodo-5-[4-(trifluoromethyl)phenoxy]-1H-pyrazol-3-yl}phenyl)propan-2-yl]-2,2,2-trifluoroethanesulfonamide (51.2 mg, 0.077 mmol) and pyridine (387 µL) was treated with copper (I) phenylacetylide (12 mg, 0.085 mmol), degassed with argon, sealed in a microwave vial and heated to 100° C. via a block heater. After 2 days the resulting brown solution was cooled, diluted with EtOAc, washed with 50% sat. aq. NaHCO₃ 2×, sat. aq NaHCO₃, dried (MgSO₄) and concentrated to afford a black residue purified via MPLC, 10 g silica, 5-30% EtOAc in heptanes to afford a light yellow solid: MS: cal'd 636 (MH+), exp 636 (MH+).

Example 120

(N-[5-(1-Ethyl-3-(4-trifluoromethylphenoxy)-1H-pyrazol-5-yl]-2,3-dihydro-1H-inden-2-yl]-N'-(2,2,2-trifluoroethyl)sulfuric diamide)

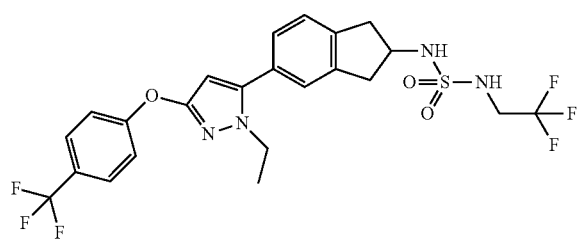 [SMILES: CCn1nc(Oc2ccc(C(F)(F)F)cc2)cc1-c1ccc2c(c1)CC(NS(=O)(=O)NCC(F)(F)F)C2]

Step 1:

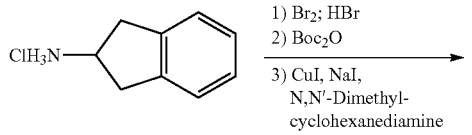

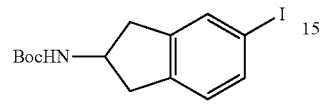

A solution of 2-amino-2,3-dihydro-1H-indene hydrochloride salt (10.0 g, 58.9 mmol) in water (50 mL) was warmed to 60° C. Next, bromine was added dropwise (3.50 mL, 67.9 mmol) over a 50 min period. Stirred for 1 hour, cooled to RT, stirred 1 hour, treated with 5 mL of 48% HBr (aq) and filtered. The residue was dried in a vacuum oven overnight (40° C.) to give 2-amino-5-bromo-2,3-dihydro-1H-indene hydrobromide salt (14.5 g, 84% yield) as a single isomer: $^1$H NMR (600 MHz, DMSO-$d_6$) δ 8.08 (br s, 3H), 7.47 (s, 1H), 7.35 (dd, J=7.9, 0.9 Hz, 1H), 7.21 (d, J=7.9 Hz, 1H), 3.97 (br s, 1H), 3.18-3.26 (m, 2H), 2.85-2.94 (m, 2H).

A mixture of 2-amino-5-bromo-2,3-dihydro-1H-indene hydrobromide salt (10.0 g, 34.1 mmol) in DCM (50 mL) was treated at 0° C. with Boc$_2$O (8.0 g, 37 mmol). The mixture was then stirred overnight at RT, diluted with EtOAc and washed with 1 N HCl, 1 N NaOH, water, dried (Na$_2$SO$_4$), and concentrated. Triturated with hexanes to a remove pale yellow color, providing N-Boc-2-amino-5-bromo-2,3-dihydro-1H-indene (9.5 g; 89% yield): $^1$H NMR (600 MHz, CDCl$_3$) δ 7.33 (s, 1H), 7.26 (dd, J=7.9, 1.8 Hz, 1H), 7.05 (d, J=8.2 Hz, 1H), 4.70 (br s, 1H), 4.43 (br s, 1H), 3.17-3.25 (m, 2H), 2.68-2.77 (m, 2H), 1.41 (s, 9H).

A mixture of N-Boc-2-amino-5-bromo-2,3-dihydro-1H-indene (2.78 g, 8.90 mmol) in n-butanol (20 mL) was treated with CuI (0.17 g, 0.89 mmol), NaI (2.67 g, 17.8 mmol) and trans-dimethylcyclohexanediamine (0.25 g, 1.8 mmol). The suspension was deoxygenated by bubbling Argon gas for 20 min, warmed to 100° C. and stirred overnight. Cooled, diluted with EtOAc and extracted with 1 N NH$_4$OH, water, dried (Na$_2$SO$_4$), and conc. Evaporated off benzene three times to remove residual solvent to provide a 3.05 g (91% yield) of a 19:1 mixture of the 5-iodo to 5-bromo precursor. Major 5-Iodo product: $^1$H NMR (600 MHz, CDCl$_3$) δ 7.55 (s, 1H), 7.47 (d, J=7.3 Hz, 1H), 6.95 (d, 0.1-7.9 Hz, 1H), 4.71 (br s, 1H), 4.42 (br s, 1H), 3.17-3.24 (m, 2H), 2.69-2.76 (m, 2H), 1.42 (s, 9H).

Step 2:

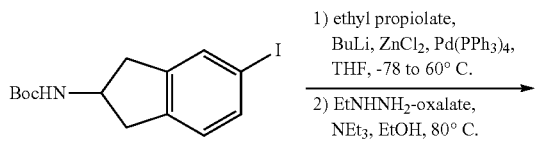

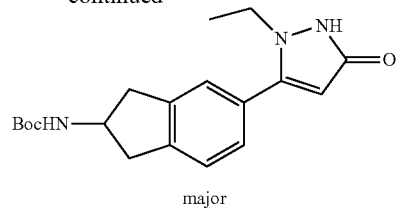

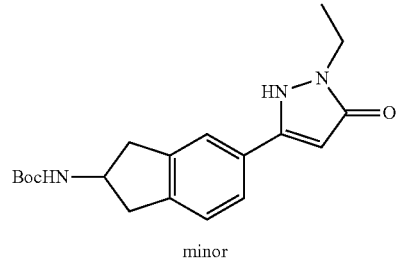

A mixture of ethyl propiolate (0.85 mL, 8.36 mmol) in THF (20 mL) was treated with a 2.5 M solution of n-BuLi in THF (3.3 mL, 8.3 mmol) at −78° C., stirred for 10 min, followed by addition of a 1.0 M solution of zinc chloride in THF (8.4 mL, 8.4 mmol). Warmed reaction to RT, added a solution of N-Boc-2-amino-5-iodo-2,3-dihydro-1H-indene (0.800 g, 2.22 mmol) in THF (1 mL) followed by Pd(PPh$_3$)$_4$ (0.30 g, 0.26 mmol). Warmed reaction mixture to 60° C., stirred for 2 hours, then cooled. Diluted with DCM, washed with 1 N HCl, water, dried (Na$_2$SO$_4$), conc. Chromatography on SiO$_2$ (0-50% EtOAc/hexanes) gave the intermediate ethyl 3-{2-[(tert-butoxycarbonyl)amino]-2,3-dihydro-1H-inden-5-yl}prop-2-ynoate (392 mg, 54% yield): $^1$H NMR (600 MHz, CDCl$_3$) δ 7.41 (s, 1H), 7.39 (d, J=8.5 Hz, 1H), 7.19 (d, J=7.6 Hz, 1H), 4.71 (br s, 1H), 4.45 (br s, 1H), 4.27 (q, J=7.0 Hz, 2H), 3.23-3.28 (m, 2H), 2.75-2.81 (m, 2H), 1.42 (s, 9H), 1.33 (t, J=Hz, 3H); MS cal'd for C$_{19}$H$_{23}$NO$_4$Na [M+Na]$^+$352.2. found 352.1.

A solution of the intermediate alkyne (1.20 g, 3.63 mmol) in EtOH (20 mL) was treated with EtNHNH$_2$-oxalate (1.50 g, 9.99 mmol) and NEt$_3$ (1.50 mL, 10.8 mmol). The reaction mixture was heated to reflux for 2 hours, cooled and concentrated. Diluted with DCM, extracted with 1 N HCl, 1 N NaOH, water, dried (Na$_2$SO$_4$) and conc. Filtered through a pad of silica (1:2 MeOH/DCM) giving a 3:1 mixture of isomeric products (388 mg, 31%), which was separated by trituration in DCM wherein the major isomer is soluble in DCM. Major isomer (tert-Butyl [5-(2-Ethyl-5-oxo-2,5-dihydro-1H-pyrazol-3-yl)-2,3-dihydro-1H-inden-2-yl]carbamate): $^1$H NMR (600 MHz, CDCl$_3$) δ 7.27 (d, J=7.6 Hz, 1H), 7.21 (s, 1H), 7.17 (d, J=7.6 Hz, 1H), 5.62 (s, 1H), 4.75 (br s, 1H), 4.49 (br s, 1H), 3.95 (q, J=7.3 Hz, 2H), 3.30 (m, 2H), 2.80-2.83 (m, 2H), 1.43 (s, 9H), 1.37 (t, J=7.0 Hz, 3H); MS cal'd for C$_{19}$H$_{26}$N$_3$O$_3$ [M+H]$^+$ 344.2. found 344.1. Minor isomer (tert-Butyl [5-(1-Ethyl-5-oxo-2,5-dihydro-1H-pyrazol-3-yl)-2,3-dihydro-1H-inden-2-yl]carbamate): $^1$H NMR (600 MHz, DMSO-$d_6$) δ 7.12 (d, J=7.7 Hz, 1H), 7.02 (s, 1H), 6.98 (d, J=8.0 Hz, 1H), 4.83 (s, 1H), 4.14-4.16 (m, 1H), 3.55 (q, J=7.1 Hz, 2H), 3.15 (s, 1H), 3.00-3.05 (m, 2H), 2.57-2.70 (m, 2H), 1.33 (s, 9H), 1.08 (t, J=7.1 Hz, 3H); MS cal'd for C$_{19}$H$_{26}$N$_3$O$_3$ [M+H]$^+$344.2. found 344.1.

Step 3:

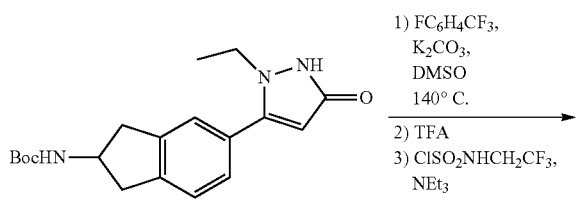

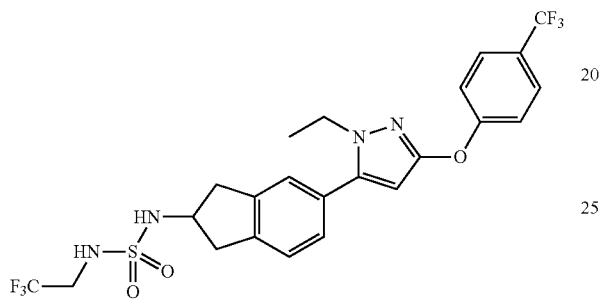

A mixture of tert-butyl [5-(2-ethyl-5-oxo-2,5-dihydro-1H-pyrazol-3-yl)-2,3-dihydro-1H-inden-2-yl]carbamate (28 mg, 0.082 mmol) in DMSO (1 mL) was treated with fluoro-4-(trifluoromethyl)benzene (100 mg, 0.609 mmol) and $K_2CO_3$ (20 mg, 0.15 mmol). The suspension was stirred for 40 min at 140° C. until no SM remained. Significant Boc thermolysis was observed under these conditions. The reaction was cooled, diluted with DCM, extracted with 1 N NaOH, water, dried ($Na_2SO_4$), concentrated. The residue was dissolved in 0.9 mL of DCM and 0.1 mL of TFA, then stirred for 1 hour, diluted with DCM, extracted with 1 N NaOH, water, dried ($Na_2SO_4$), and finally concentrated to give 5-{1-ethyl-3-[4-(trifluoromethyl)phenoxy]-1H-pyrazol-5-yl}-2,3-dihydro-1H-inden-2-amine (18 mg, 57%): MS cal'd for $C_{21}H_{21}F_3N_3O$ $[M+H]^+$ 388.2. found 388.1.

A solution of 5-{1-ethyl-3-[4-(trifluoromethyl)phenoxy]-1H-pyrazol-5-yl}-2,3-dihydro-1H-inden-2-amine (18 mg, 0.046 mmol) in DCM (1 mL) was treated at −78° C. with a 1.0 M solution of 2,2,2-trifluoroethylsulfuryl chloride in DCM (0.10 mL, 0.10 mmol) and $NEt_3$ (0.020 mL, 0.12 mmol). The reaction mixture was stirred 1 h, diluted with DCM, extracted with 1 N NaOH, water, dried ($Na_2SO_4$), and concentrated. Chromatography on $SiO_2$ (0-100% EtOAc/DCM) gave 21 mg (82% yield) of N-[5-(1-ethyl-3-(4-trifluoromethylphenoxy)-1H-pyrazol-5-yl)-2,3-dihydro-1H-inden-2-yl]-N'-(2,2,2-trifluoroethyl)sulfuric diamide: $^1$H NMR (600 MHz, $CDCl_3$) d 7.56 (d, J=8.5 Hz, 2H), 7.30 (d, J=7.6 Hz, 1H), 7.21-7.24 (m, 4H), 5.82 (s, 1H), 4.71 (t, J=7.0 Hz, 1H), 4.55 (d, J=8.5 Hz, 1H), 4.26-4.29 (m, 1H), 4.06 (q, J=7.3 Hz, 2H), 3.70 (m, 2H), 3.33-3.37 (m, 2H), 2.96-3.01 (m, 2H), 1.39 (t, J=7.3 Hz, 3H); MS cal'd for $C_{23}H_{23}F_6N_4O_3S$ $[M+H]^+$ 549.1. found 549.1.

Example 121

N-[5-(1-Ethyl-5-(4-trifluoromethylphenoxy)-1H-pyrazol-3-yl)-2,3-dihydro-1H-inden-2-yl]-N'-(2,2,2-trifluoroethyl)sulfuric diamide)

N-[5-(1-Ethyl-5-(4-trifluoromethylphenoxy)-1H-pyrazol-3-yl)-2,3-dihydro-1H-inden-2-yl]-N-(2,2,2-trifluoroethyl) sulfuric diamide was prepared from (tert-Butyl [5-(1-Ethyl-5-oxo-2,5-dihydro-1H-pyrazol-3-yl)-2,3-dihydro-1H-inden-2-yl]carbamate): as above: MS cal'd for $C_{23}H_{23}F_6N_4O_3S$ $[M+H]^+$549.1. found 549.1.

The following examples were made by similar procedures:

| # | Structure | Name | Calc Mass $(M + 1)^+$ | Exp Mass $(M + 1)^+$ |
|---|---|---|---|---|
| 122 | 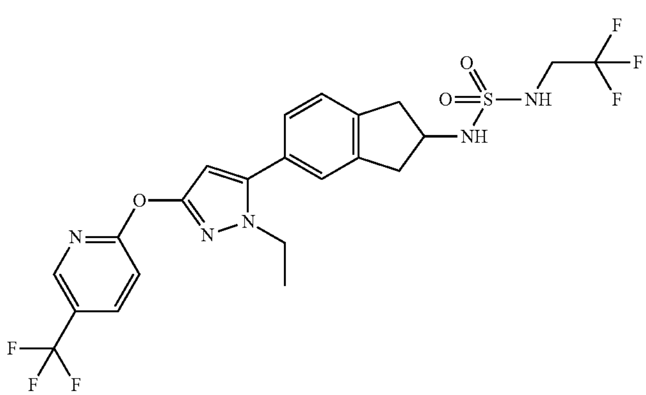 [SMILES: CCn1nc(Oc2ccc(C(F)(F)F)cn2)cc1-c1ccc2c(c1)CC(NS(=O)(=O)NCC(F)(F)F)C2] | N-[5-(1-ethyl-3-{[5-(trifluoromethyl)pyridin-2-yl]oxy}-1H-pyrazol-5-yl)-2,3-dihydro-1H-inden-2-yl]-N'-(2,2,2-trifluoroethyl)sulfamide | 550.1 | 550.1 |

-continued
| # | Structure | Name | Calc Mass (M + 1)+ | Exp Mass (M + 1)+ |
|---|---|---|---|---|
| 123 | 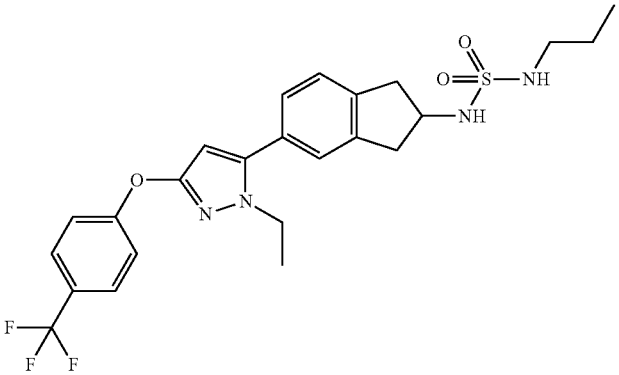 [SMILES: CCCNS(=O)(=O)NC1Cc2ccc(-c3cc(Oc4ccc(C(F)(F)F)cc4)nn3CC)cc2C1] | N-(5-{1-ethyl-3-[4-(trifluoromethyl)phenoxy]-1H-pyrazol-5-yl}-2,3-dihydro-1H-inden-2-yl)-N'-propylsulfamide | 509.2 | 590.1 |
| 124 | 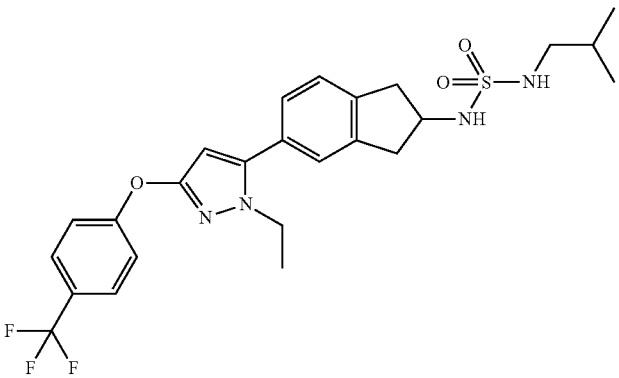 [SMILES: CCn1nc(Oc2ccc(C(F)(F)F)cc2)cc1-c1ccc2c(c1)CC(NS(=O)(=O)NCC(C)C)C2] | N-(5-{1-ethyl-3-[4-(trifluoromethyl)phenoxy]-1H-pyrazol-5-yl}-2,3-dihydro-1H-inden-2-yl)-N'-isobutylsulfamide | 523.2 | 523.1 |
| 125 | 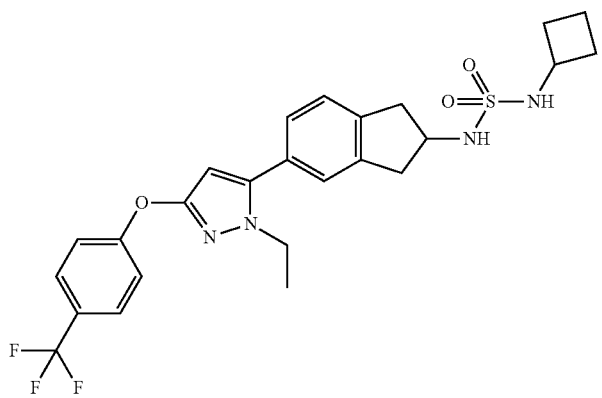 [SMILES: CCn1nc(Oc2ccc(C(F)(F)F)cc2)cc1-c1ccc2c(c1)CC(NS(=O)(=O)NC1CCC1)C2] | N-cyclobutyl-N'-(5-{1-ethyl-3-[4-(trifluoromethyl)phenoxy]-1H-pyrazol-5-yl}-2,3-dihydro-1H-inden-2-yl)sulfamide | 521.2 | 521.1 |

Example 126

N-[3-(5-{1-ethyl-5-[4-(trifluoromethyl)phenoxy]-1H-pyrazol-3-yl}pyridine-3-yl)oxetan-3-yl]-2,2,2-trifluoroethanesulfonamide

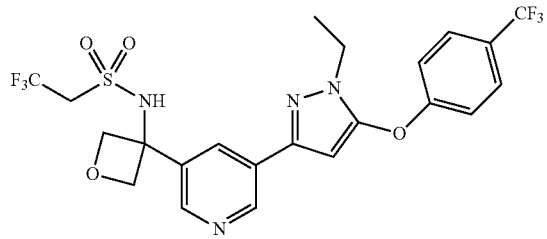 [SMILES: CCn1nc(-c2cncc(C3(NS(=O)(=O)CC(F)(F)F)COC3)c2)cc1Oc1ccc(C(F)(F)F)cc1]

Step 1:

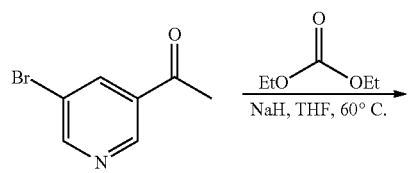

Ethyl 3-(5-bromopyridin-3-yl)-3-oxopropanoate was prepared from 1-(5-bromopyridin-3-yl)ethanone with a procedure similar to that used in Example 1, Step 1. Calc'd (M+): 272.1. Found: 272.2.

Step 2:

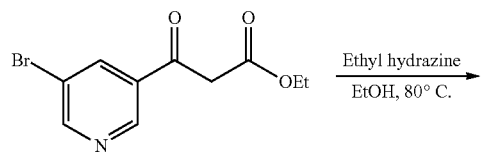

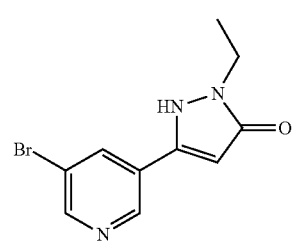

5-(5-bromopyridin-3-yl)-2-ethyl-1,2-dihydro-3H-pyrazol-3-one was prepared from ethyl 3-(5-bromopyridin-3-yl)-3-oxopropanoate with a procedure similar to that used in Example 1, Step 2. Calc'd (M+): 268.1. Found: 268.2.

Step 3:

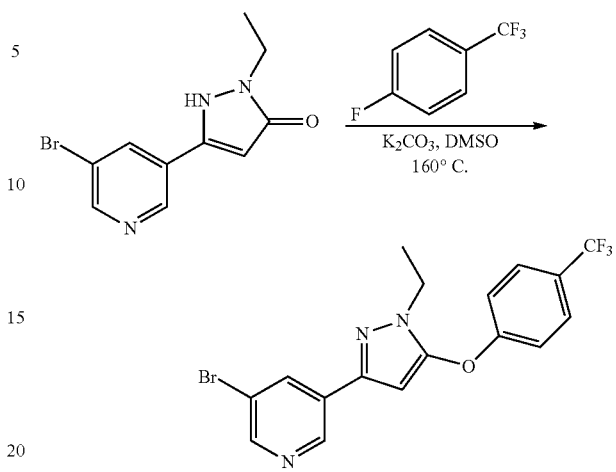

3-bromo-5-{1-ethyl-5-[4-(trifluoromethyl)phenoxy]-1H-pyrazol-3-yl}pyridine was prepared from 5-(5-bromopyridin-3-yl)-2-ethyl-1,2-dihydro-3H-pyrazol-3-one with a procedure similar to that used in Example 1, Step 3. Calc'd (M+): 412.2. Found: 412.3.

Step 4:

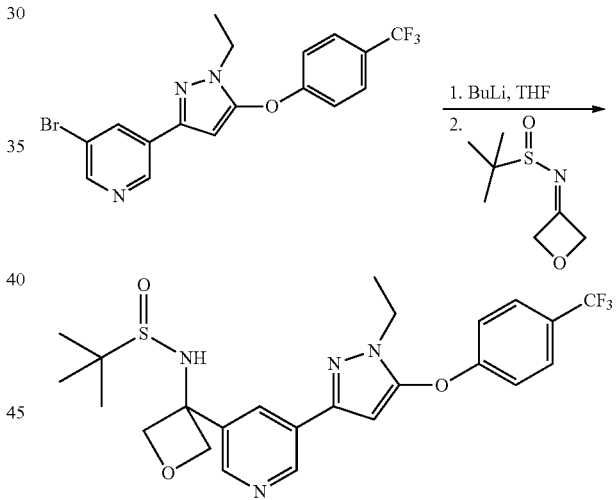

A solution of n-butyllithium in hexanes (1.6 M, 0.35 mL, 0.56 mmol, 1.5 equiv) was added to a solution of 3-bromo-5-{1-ethyl-5-[4-(trifluoromethyl)phenoxy]-1H-pyrazol-3-yl}pyridine (152 mg, 0.37 mmol, 1.0 equiv) in tetrahydrofuran (1.5 mL) and hexanes (1.5 mL) at −78° C. The reaction mixture was stirred at −78° C. for 10 minutes, and then 2-methyl-N-oxetan-3-ylidenepropane-2-sulfinamide (Example 95, Step 4, 75 mg, 0.43 mmol, 1.15 equiv) was added neat via syringe. The reaction mixture was stirred at −78° C. for 5 minutes, then the cooling bath was removed. After 5 minutes, the mixture was quenched with water (2 mL) and extracted with EtOAc (3×5 mL). The combined organic layer was dried over MgSO$_4$, filtered, and concentrated. The crude residue was purified by silica gel chromatography (50-100% EtOAc/hexane, then 0-5% MeOH/EtOAc) to give N-[3-(5-{1-ethyl-5-[4-(trifluoromethyl)phenoxy]-1H-pyrazol-3-yl}pyridine-3-yl)oxetan-3-yl]-2-methylpropane-2-sulfinamide (125 mg, 57%). Calc'd (M+1)$^+$: 508.6. Found: 509.5.

Step 5:

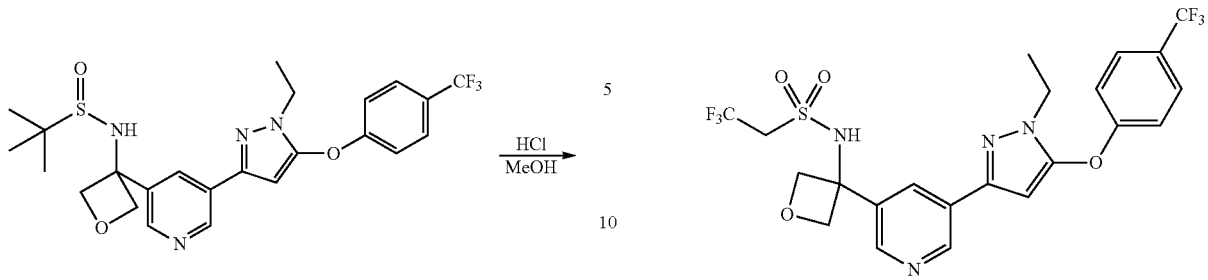

N-[3-(5-{1-ethyl-5-[4-(trifluoromethyl)phenoxy]-1H-pyrazol-3-yl}pyridine-3-yl)oxetan-3-yl]-2,2,2-trifluoroethanesulfonamide was prepared from 3-(5-{1-ethyl-5-[4-(trifluoromethyl)phenoxy]-1H-pyrazol-3-yl}pyridine-3-yl)oxetan-3-amine with a procedure similar to that used in Example 1, Step 5. HRMS Calc'd (M+1)$^+$: 551.1182. Found: 551.1186. $^1$H NMR (400 MHz, CDCl$_3$) δ 8.99 (d, J=1.6, 1H), 8.71 (d, J=1.6, 1H), 8.34 (s, 1H), 7.68 (d, J=9.2, 2H) 7.24 (d, J=9.2, 2H), 6.13 (s, 1H), 6.01 (s, 1H), 5.10 (d, J=7.2, 2H), 5.07 (d, J=7.2, 2H), 4.15 (q, J=7.2, 2H), 3.43 (q, J=8.4, 2H), 1.48 (t, J=7.2, 3H).

The following compound was prepared from 3-(5-{1-ethyl-5-[4-(trifluoromethyl)phenoxy]-1H-pyrazol-3-yl}pyridine-3-yl)oxetan-3-amine with a similar procedure, varying the sulfonyl/sulfomyl chloride used.

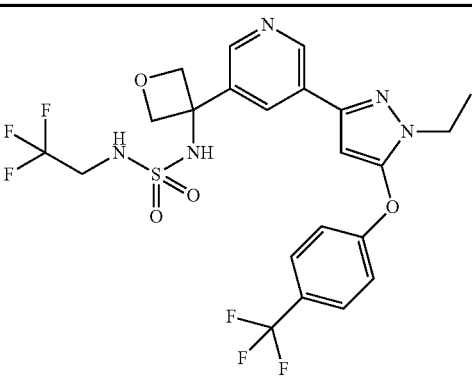

| # | Structure | Name | Calc Mass (M + 1)$^+$ | Exp Mass (M + 1)$^+$ |
|---|-----------|------|------------------------|----------------------|
| 127 | 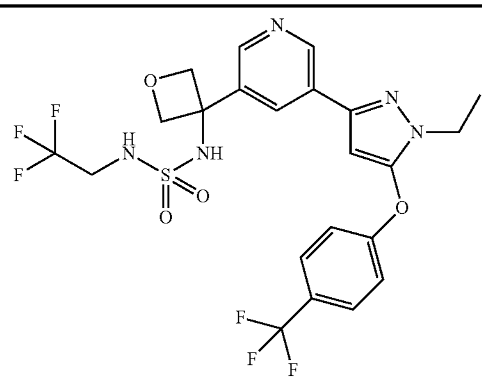 | N-[3-(5-{1-ethyl-5-[4-(trifluoromethyl)phenoxy]-1H-pyrazol-3-yl}pyridine-3-yl)oxetan-3-yl]-N'-(2,2,2-trifluoroethyl)sulfamide | 566.5 | 566.4 |

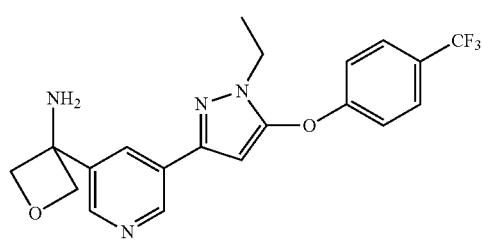

3-(5-{1-ethyl-5-[4-(trifluoromethyl)phenoxy]-1H-pyrazol-3-yl}pyridine-3-yl)oxetan-3-amine was prepared from N-[3-(5-{1-ethyl-5-[4-(trifluoromethyl)phenoxy]-1H-pyrazol-3-yl}pyridine-3-yl)oxetan-3-yl]-2-methylpropane-2-sulfinamide with a procedure similar to that used in Example 95, Step 6. Calc'd (M+1)$^+$: 405.4. Found: 405.4.

Step 6:

Example 128

N-(3-{3-[5-4-cyanophenoxy)-1-ethyl-1H-pyrazol-3-yl]phenyl}oxetane-3-yl)-2,2,2-trifluoroethanesulfonamide

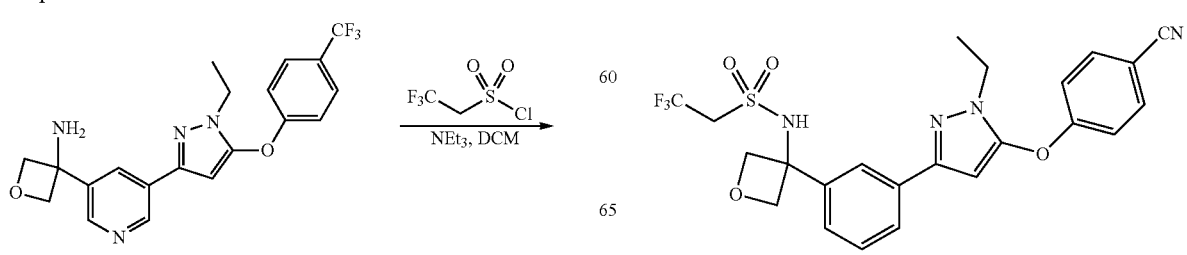

Step 1:

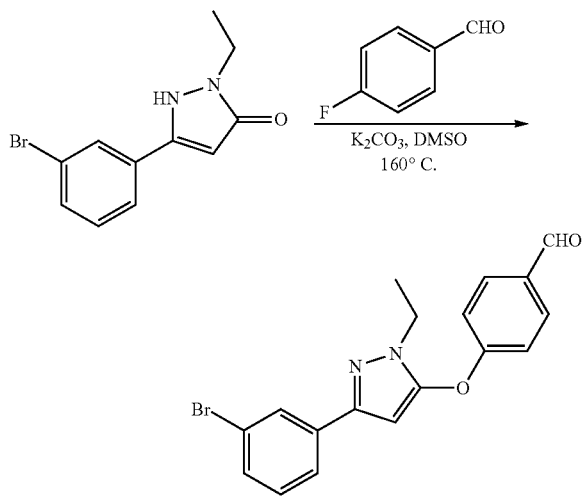

4-{[3-(3-bromophenyl)-1-ethyl-1H-pyrazol-5-yl]oxy}benzaldehyde was prepared from 5-(3-bromophenyl)-2-ethyl-1,2-dihydro-3H-pyrazol-3-one (Example 95, Step 2) with a procedure similar to that used in Example 1, Step 3. Calc'd (M+1)⁺: 371.0. Found: 371.2.

Step 2:

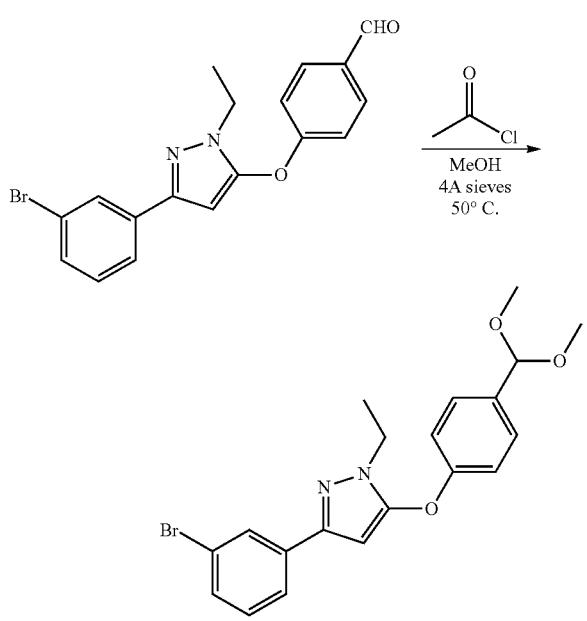

Acetyl chloride (0.023 ml, 0.323 mmol, 0.1 equiv) was added to a stirring solution of 4-{[3-(3-bromophenyl)-1-ethyl-1H-pyrazol-5-yl]oxy}benzaldehyde (1.2 g, 3.23 mmol, 1.0 equiv) in methanol (7 mL). 4A molecular sieves were added and the mixture was stirred at 50° C. for 3 hours. The sieves were filtered and the filtrate was concentrated. The crude product was purified by flash chromatography on silica gel (0-70% ethyl acetate:hexanes) to give 3-(3-bromophenyl)-5-[4-(dimethoxymethyl)phenoxy]-1-ethyl-1H-pyrazole (1.2 g, 2.88 mmol, 89% yield). Calc'd (M+1)⁺419.0. Found: 419.19 (minor peak), 373.18 (major peak). Major peak is aldehyde seen because of deprotection occurring on LCMS.

Step 3:

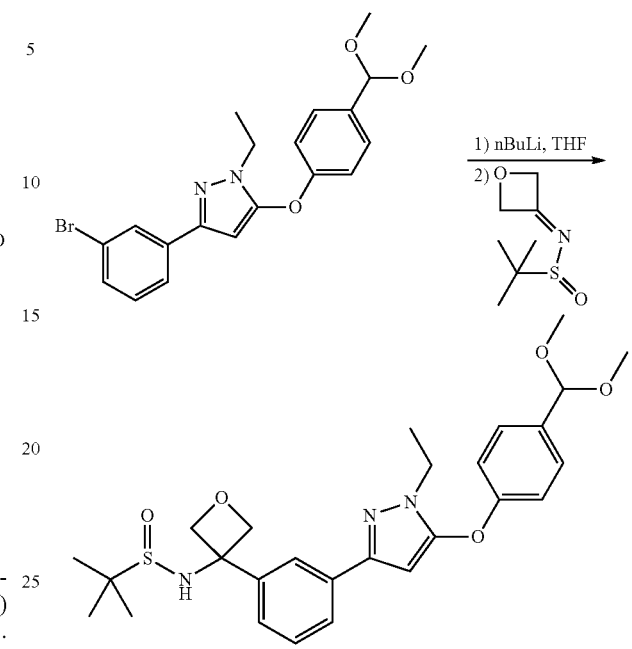

A solution of n-Butyllithium in hexanes (2.5M, 3.83 mL, 9.59 mmol, 2.0 equiv) was added dropwise to a solution of 3-(3-bromophenyl)-5-[4-(dimethoxymethyl)phenoxy]-1-ethyl-1H pyrazole (2.0 g, 4.79 mmol, 1.0 equiv) in THF (32 mL) at −78° C. To this mixture was added dropwise a solution of 2-methyl-N-oxetane-3-ylidenepropane-2-sulfinamide (0.840 g, 4.79 mmol, 1.0 equiv, Example 95, Step 4) in 5 mL THF. The reaction mixture was stirred at −78° C. for 10 minutes and the cooling bath was removed. Saturated aqueous ammonium chloride solution was added, and the crude product was partitioned between ethyl acetate and water. The organic layer was washed with saturated aqueous sodium chloride solution and dried over magnesium sulfate. The dried solution was filtered and the filtrate was concentrated. The residue was purified by flash chromatography on silica gel (0-100% ethyl acetate:hexanes then flushing with 10% methanol/dichloromethane) to afford N-[3-{3-{5-[4-(dimethoxymethyl)phenoxy]-1-ethyl-1H-pyrazol-3-yl}phenyl)oxetan-3-yl]-2-methylpropane-2-sulfinamide (2.17 g, 4.22 mmol, 88% yield). Calc'd (M+1)⁺501.23. Found: 468.1. Found mass is aldehyde formed from deprotection of acetal on LCMS.

Step 4:

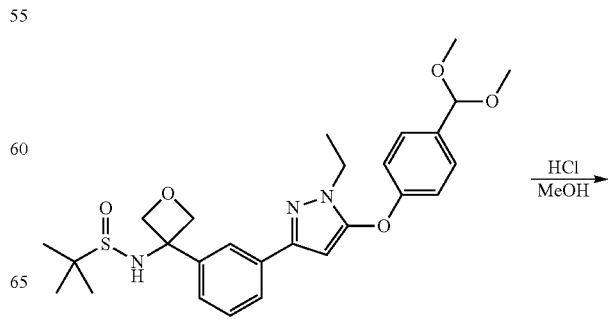

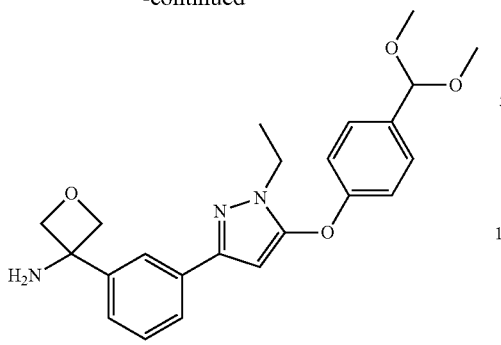

3-(3-{5-[4-(dimethoxymethyl)phenoxy]-1-ethyl-1H-pyrazole-3-yl}phenyl)oxetane-3-amine was prepared from N-[3-{3-{5-[4-(dimethoxymethyl)phenoxy]-1-ethyl-1H-pyrazol-3-yl}phenyl)oxetan-3-yl]-2-methylpropane-2-sulfinamide with a procedure similar to that used in Example 95, Step 6. Calc'd (M+1)⁺409.20. Found: 364.1. Found mass is aldehyde from deprotection on LCMS.

Step 5:

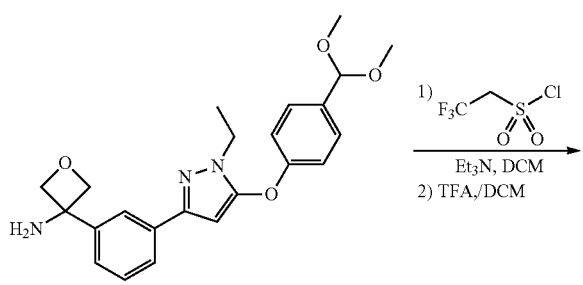

N-(3-{3-[1-ethyl-5-(4-formylphenoxy)-1H-pyrazol-3-yl]phenyl}oxetane-3-yl)-2,2,2-trifluoroethanesulfonamide was prepared from 3-(3-{5-[4-(dimethoxymethyl)phenoxy]-1-ethyl-1H-pyrazol-3-yl}phenyl)oxetane-3-amine with a procedure similar to that used in Example 61, Step 4. Calc'd (M+1)⁺510.0. Found: 510.0.

Step 6:

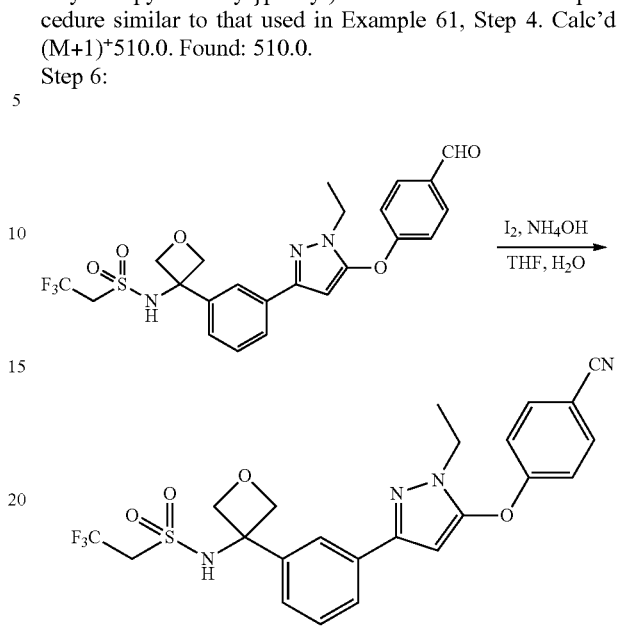

Iodine (17.5 mg, 0.069 mmol, 1.3 equiv) was added to a stirring biphasic solution of N-(3-{3-[1-ethyl-5-(4-formylphenoxy)-1H-pyrazol-3-yl]phenyl}oxetane-3-yl)-2,2,2-trifluoroethanesulfonamide (27 mg, 0.053 mmol, 1.0 equiv) in 1 mL THF and 0.53 mL of concentrated NH₄OH (28% solution). After stirring for 7 hours, aqueous Na₂S₂O₃ was added (1 mL of a 5% solution) and the reaction mixture was extracted with diethyl ether. The organic layer was dried over magnesium sulfate. The dried solution was filtered and the filtrate was concentrated. The residue was purified by flash chromatography on silica gel (0-60% ethyl acetate:hexanes) to give N-(3-{3-[5-(4-cyanophenoxy)-1-ethyl-1H-pyrazol-3-yl]phenyl}oxetane-3-yl)-2,2,2-trifluoroethanesulfonamide (17 mg, 0.034 mmol, 65% yield). HRMS Calc'd (M+1)⁺507.1308. Found: 507.1305. (400 MHz, ¹H, δ-CDCl₃) 1.45 (3H, t, J=7.2), 3.04 (2H, q, J=8.6), 4.10 (2H, q, J=7.2), 5.04 (2H, d, J=7.1), 5.16 (2H, d, J=7.1), 5.66 (1H, br s), 6.11 (1H, s), 7.22 (2H, d, H=8.6), 7.36 (1H, d, J=7.9), 7.51 (1H, t, J=8.0), 7.70 (2H, d, J=8.6), 7.80 (2H, m).

The following compounds were prepared from 3-(3-{5-[4-(dimethoxymethyl)phenoxy]-1-ethyl-1H-pyrazol-3-yl}phenyl)oxetane-3-amine with similar procedures, varying the sulfonyl/sulfomyl chloride used.

| # | Structure | Name | Calc Mass (M + 1)⁺ | Exp Mass (M + 1)⁺ |
|---|---|---|---|---|
| 129 | 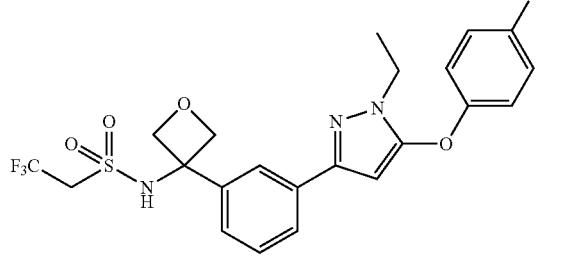 | N-(3-{3-[5-(4-cyanophenoxy)-1-ethyl-1H-pyrazol-3-yl]phenyl}oxetane-3-yl)-N'-(2,2,2-trifluoroethyl)sulfamide | 522.1 | 522.2 |

| # | Structure | Name | Calc Mass (M + 1)+ | Exp Mass (M + 1)+ |
|---|-----------|------|---------------------|--------------------|
| 130 | 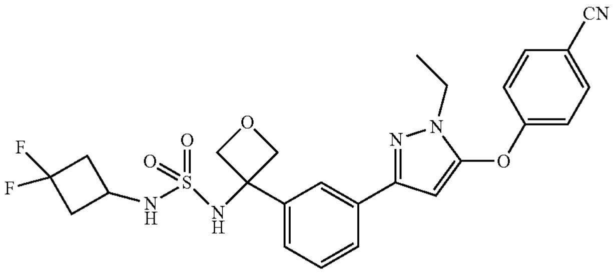 [SMILES: CCn1nc(-c2cccc(C3(NS(=O)(=O)NC4CC(F)(F)C4)COC3)c2)cc1Oc1ccc(C#N)cc1] | N-(3-{3-[5-(4-cyanophenoxy)-1-ethyl-1H-pyrazol-3-yl]phenyl}oxetane-3-yl)-N'-(3,3-difluorocyclobutyl)sulfamide | 530.1 | 530.1 |

Example 131

2-[5-(4-trifluoromethylphenoxy)-3-(3-{3-[(2,2,2-trifluoroethylsulfonyl)amino]oxetan-3-yl}phenyl)-1H-pyrazol-1-yl]-N,N-dimethylacetamide

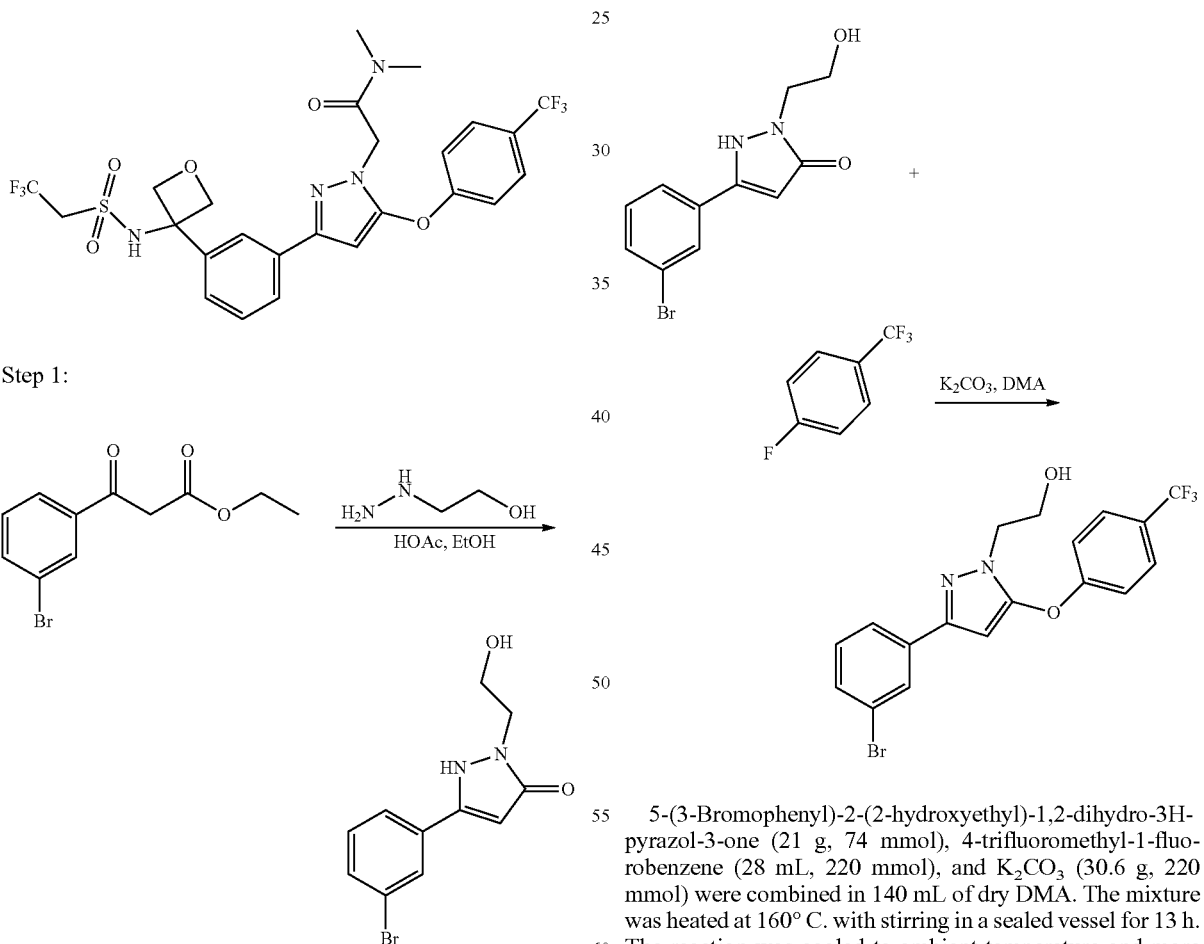

Step 1:

Ethyl 3-(3-bromophenyl)-3-oxopropanoate from Example 95, Step 1 (20 g, 74 mmol) and 2-hydroxyethylhydrazine (10 mL, 148 mmol) were combined in 240 mL of EtOH. Acetic acid (12 mL, 220 mmol) was added and the mixture was stirred at ambient temperature for 3 h. The solvents were removed under reduced pressure. The residue was dissolved in EtOAc and the solution was washed with water and brine, then dried over MgSO₄, filtered, and the solvent was removed under reduced pressure to give 5-(3-bromophenyl)-2-(2-hydroxyethyl)-1,2-dihydro-3,1-pyrazol-3-one as an oil. Calcd (M+1)+: 284.1. Found: 284.2

Step 2:

5-(3-Bromophenyl)-2-(2-hydroxyethyl)-1,2-dihydro-3H-pyrazol-3-one (21 g, 74 mmol), 4-trifluoromethyl-1-fluorobenzene (28 mL, 220 mmol), and K₂CO₃ (30.6 g, 220 mmol) were combined in 140 mL of dry DMA. The mixture was heated at 160° C. with stirring in a sealed vessel for 13 h. The reaction was cooled to ambient temperature and more 4-trifluoromethyl-1-fluorobenzene (5 mL, 39 mmol) was added. The mixture was heated at 160° C. with stirring in a sealed vessel for 18 h. The reaction was cooled to ambient temperature and diluted with EtOAc. The mixture was washed with water and brine, then dried over MgSO₄, filtered, and the solvent was removed under reduced pressure. The dark residue was chromatographed on a 330 g silica gel column using 0-40% EtOAc:hexanes over 70 min at 100 mL/min. The product-containing fractions were combined and the solvent was removed under reduced pressure to give 2-{3-(3-bromophenyl)-5-[4-(trifluoromethyl)phenoxy]-1H-pyrazol-1-yl}ethanol as an oil which solidified on standing. Calcd (M−1-1)+: 428.2. Found: 428.3

Step 3:

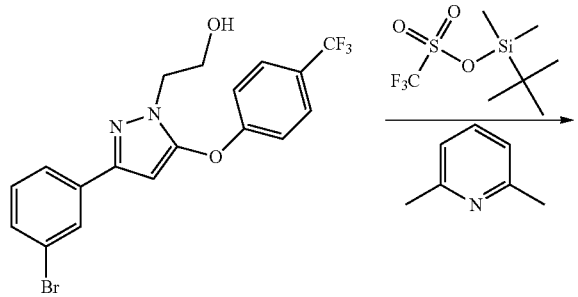

Step 4:

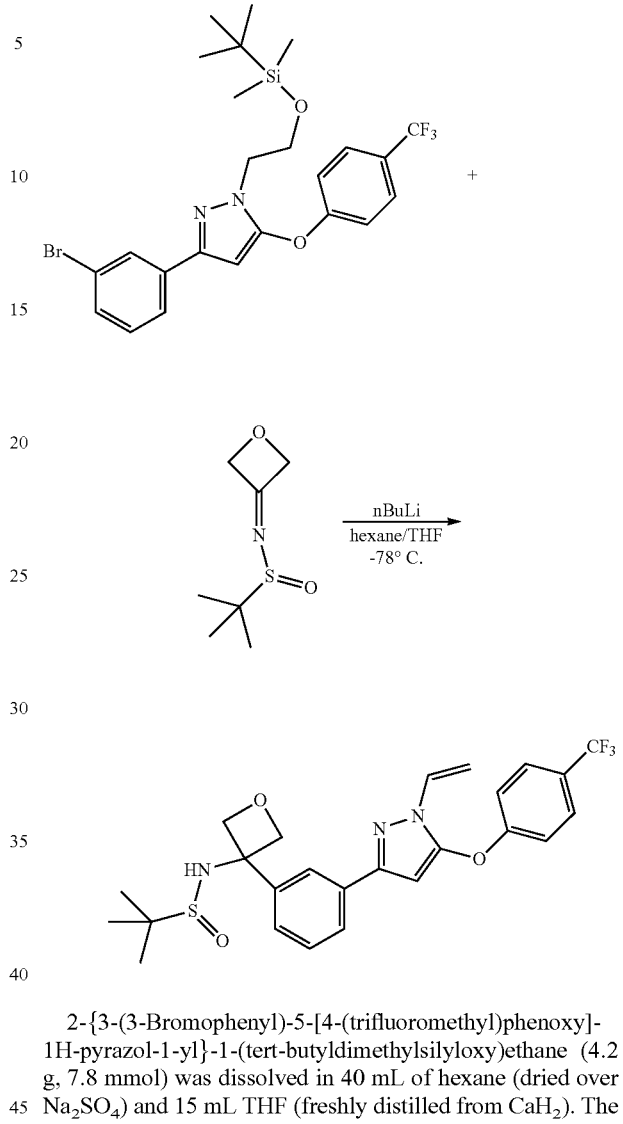

A stirred solution of 2-{3-(3-bromophenyl)-5-[4-(trifluoromethyl)phenoxy]-1H-pyrazol-1-yl}ethanol (7.6 g, 18 mmol) and 2,6-lutidine (6.2 mL, 53 mmol) in 40 mL of CH$_2$Cl$_2$ under an argon atmosphere was cooled in an ice bath. TBDMS triflate (7.1 g, 27 mmol) was added dropwise and the mixture was stirred for 30 min. The mixture was diluted with CH$_2$Cl$_2$ and washed with saturated aqueous NaHCO$_3$, water, brine, then dried over Na$_2$SO$_4$, filtered, and the solvents were removed under reduced pressure. The residue was chromatographed on a 120 g silica gel column using 0-70% CHCl$_3$: hexanes over 40 min at 85 mL/min. The product-containing fractions were combined and the solvent was removed under reduced pressure to give 2-{3-(3-bromophenyl)-5-[4-(trifluoromethyl)phenoxy]-1H-pyrazol-1-yl}-1-(tert-butyldimethylsilyloxy)ethane as an oil. Calcd (M+1)+: 542.5. Found: 542.8

2-{3-(3-Bromophenyl)-5-[4-(trifluoromethyl)phenoxy]-1H-pyrazol-1-yl}-1-(tert-butyldimethylsilyloxy)ethane (4.2 g, 7.8 mmol) was dissolved in 40 mL of hexane (dried over Na$_2$SO$_4$) and 15 mL THF (freshly distilled from CaH$_2$). The solution was sparged with argon and cooled to −78° C. To the stirred solution was added nBuLi (6.21 mL of a 2.5 M solution in hexanes, 15.5 mmol) and the mixture was stirred for 15 min. LCMS showed incomplete reaction, so more nBuLi (1.0 mL, 2.5 mmol) was added and the mixture was stirred for 10 min. 2-Methyl-N-(oxetan-3-ylidene)propane-2-sulfinamide (1.4 g, 7.8 mmol) was dissolved in 10 mL of THF (freshly distilled from CaH$_2$) and cooled to −78° C. The cold solution of sulfinamide was added via cannula into the cold solution of anion. The resulting mixture was stirred for 10 min, then quenched by addition of 20% aqueous NH$_4$Cl solution. The mixture was warmed to ambient temperature and extracted with EtOAc. The EtOAc layer was washed with water and brine, then dried over MgSO$_4$, and the solvents were removed under reduced pressure. The residue was chromatographed on a 120 g silica gel column using 0-100% EtOAc:hexanes over 36 min at 85 mL/min. The product-containing fractions were combined and the solvents were removed under reduced pressure to give N-{3-[3-(1-ethenyl-5-(4-trifluoromethylphenoxy)-1H-pyrazol-3-yl)phenyl]oxetan-3-yl}tert-butylsulfinamide as an oil. Calcd (M+1)+: 506.6. Found: 506.3

Step 5:

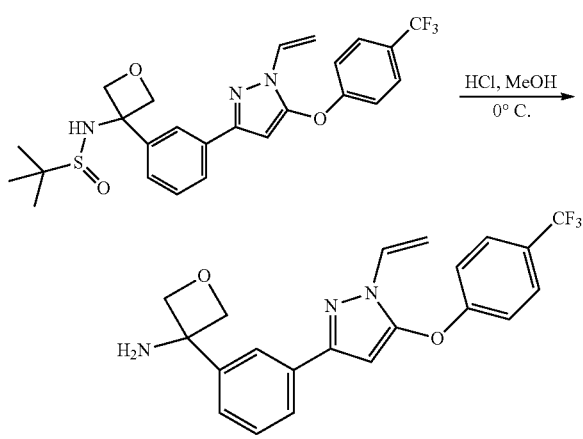

A stirred solution of N-{3-[3-(1-ethenyl-5-(4-trifluoromethylphenoxy)-1H-pyrazol-3-yl)phenyl]oxetan-3-yl}tert-butylsulfinamide (1.63 g, 3.22 mmol) in 40 mL of methanol was cooled in an ice bath. 4M HCl in dioxane (3.2 mL, 13 mmol) was added and the mixture was stirred for 45 min. Saturated aqueous NaHCO$_3$ solution was added and mixture was warmed to ambient temperature and extracted with EtOAc. The EtOAc layer was washed with brine, dried over MgSO$_4$, filtered, and the solvent was removed under reduced pressure to give 3-(3-{1-ethenyl-5-[4-(trifluoromethyl)phenoxy]-1H-pyrazol-3-yl}phenyl)oxetan-3-amine as an oil. Calcd (M+1)$^+$: 402.4. Found: 402.8

Step 6:

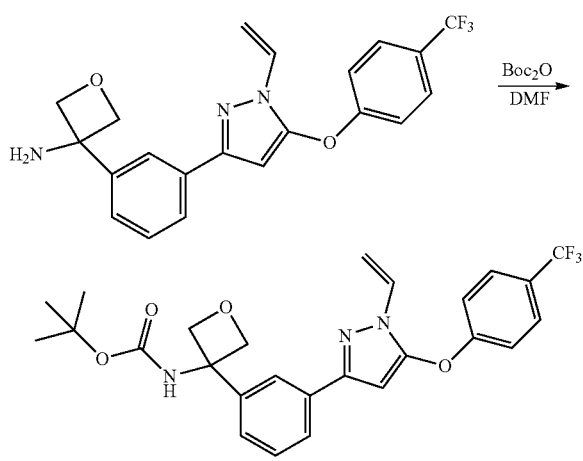

3-(3-{1-Ethenyl-5-[4-(trifluoromethyl)phenoxy]-1H-pyrazol-3-yl}phenyl)oxetan-3-amine (1.3 g, 3.2 mmol) was dissolved in 6 mL of DMF and di-tert-butyldicarbonate (1.4 g, 6.4 mmol) was added. The mixture was stirred at ambient temperature for 18 h. The mixture was diluted with EtOAc and washed with water and brine. The organic phase was dried over MgSO$_4$, filtered, and the solvent was removed under reduced pressure. The residue was chromatographed on a 12 g silica gel column using 0-30% EtOAc:hexanes over 16 min at 30 mL/min. The product-containing fractions were combined and the solvents were removed under reduced pressure to give tert-butyl {3-[3-(1-ethenyl-5-(4-trifluoromethylphenoxy)-1H-pyrazol-3-yl)phenyl]oxetan-3-yl}carbamate as a foam. Calcd (M+1)$^+$: 502.5. Found: 502.2

Step 7:

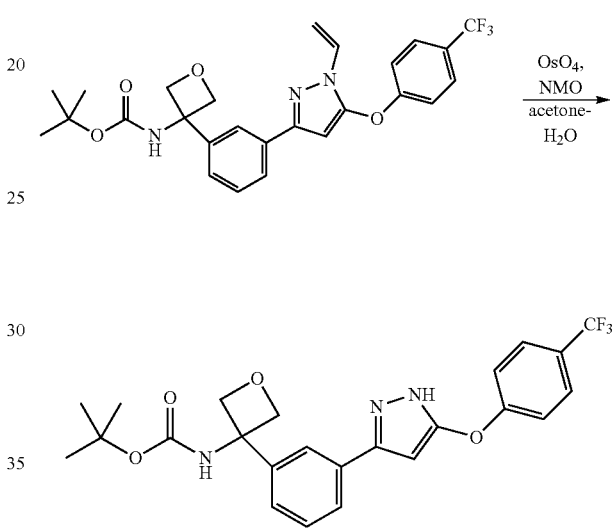

A stirred solution of tert-butyl {3-[3-(1-ethenyl-5-(4-trifluoromethylphenoxy)-1H-pyrazol-3-yl)phenyl]oxetan-3-yl}carbamate (1.02 g, 2.03 mmol) in 14 mL of 2.5:1 acetone:water was cooled in an ice bath. To the stirred solution was added OsO$_4$ (2.6 mL of a 5.5 weight % solution in water, 0.2 mmol) and N-methylmorpholine N-oxide (2.4 g, 2.1 mmol). The mixture was stirred for 3.5 h. 10% Aqueous Na$_2$SO$_3$ solution was added. The mixture was stirred for 5 min, then extracted with EtOAc. The combined organic phases were washed with water and brine, then dried over MgSO$_4$, filtered, and the solvents were removed under reduced pressure to give tert-butyl {3-[3-(5-(4-trifluoromethylphenoxy)-1H-pyrazol-3-yl)phenyl]oxetan-3-yl}carbamate as a dark solid. Calcd (M+1)$^+$: 476.5. Found: 476.2

Step 8:

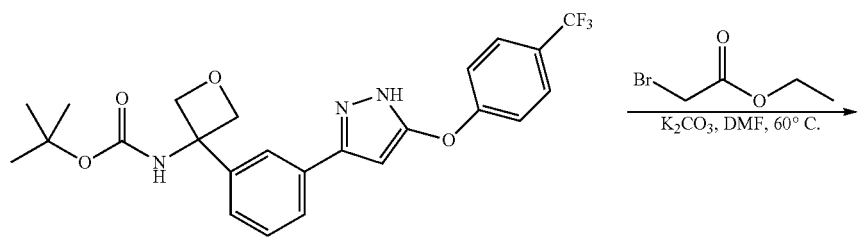

-continued

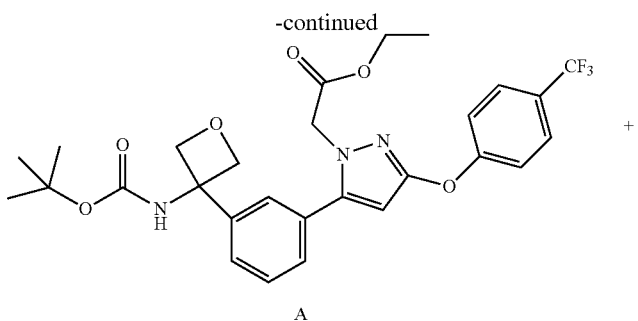

A

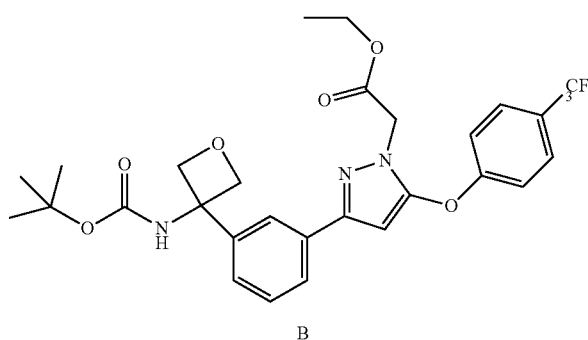

B tert-Butyl {3-[3-(5-(4-trifluoromethylphenoxy)-1H-pyrazol-3-yl)phenyl]oxetan-3-yl}carbamate (98 mg, 0.21 mmol), ethyl bromoacetate (80 mg, 0.47 nimbi), and potassium carbonate (67 mg, 0.48 mmol) were combined in 0.5 mL of DMF and the mixture was stirred at ambient temperature under argon atmosphere for 4 h, then warmed to 60° C. for 18 h. The mixture was diluted with EtOAc and washed with water and brine. The organic phase was dried over MgSO$_4$, filtered, and the solvent was removed under reduced pressure. The residue was chromatographed on a 12 g silica gel column using 0-5% MeOH:CHCl$_3$ over 16 min at 30 mL/min. The fractions containing the first-eluting product were combined and evaporated under reduced pressure to give ethyl [3-(4-trifluoromethylphenoxy)-5-(3-{3-[(tert-butyloxycarbonyl)amino]oxetan-3-yl}phenyl)-1H-pyrazol-1-yl]acetate (product A) as an oil, calcd (M+1)$^+$: 562.6. Found: 562.2. $^1$H NMR (400 MHz, CDCl$_3$) δ 7.6 (m, 5H), 7.50 (t, J=7, 1H), 7.37 (d, J=7, 1H), 7.29 (s, 1H), 5.99 (s, 1H), 5.85 (br s, 1H), 5.00 (d, J=5, 2H), 4.85 (br d, 2H), 4.79 (s, 2H), 4.21 (q, J=7, 2H), 1.27 (t, J=7, 3H). The fractions containing the second-eluting product were combined and evaporated under reduced pressure to give ethyl [5-(4-trifluoromethylphenoxy)-3-(3-{3-[(tert-butyloxycarbonyl)amino]oxetan-3-yl}phenyl)-1H-pyrazol-1-yl]acetate (product B) as an oil, calcd (M+1)$^+$: 562.6. Found: 562.9. $^1$H NMR (400 MHz, CDCl$_3$) δ 7.88 (br s, 1H), 7.6 (m, 3H), 7.50 (d, J=7, 1H), 7.42 (t, J=7, 1H), 7.32 (d, J=6, 2H), 6.03 (s, 1H), 5.82 (br s, 1H), 5.00 (br s, 2H), 4.90 (overlapping brs s and sharp s, 4H), 4.21 (q, J=7, 2H), 1.25 (t, J=7, 3H).

Step 9:

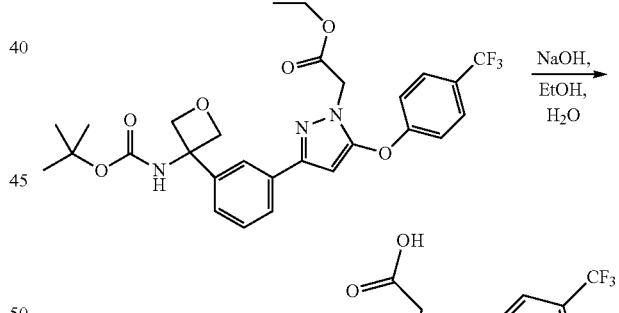

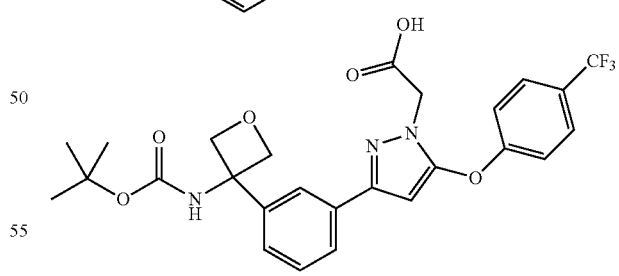

Ethyl [5-(4-trifluoromethylphenoxy)-3-(3-{3-[(tert-butyloxycarbonyl)amino]oxetan-3-yl}phenyl)-1H-pyrazol-1-yl]acetate (98 mg, 0.18 mmol) was dissolved in 0.5 mL of EtOH and to the stirred solution was added 1N aqueous NaOH solution (0.35 mL, 0.35 mmol). The mixture was stirred for 20 min and then 0.35 mL of 1N aqueous HCl was added dropwise. The solvents were removed under reduced pressure and the residue was partitioned between EtOAc and 10% aqueous citric acid solution. The organic phase was washed with brine, dried over MgSO₄, filtered, and the solvent was removed under reduced pressure to give [5-(4-trifluoromethylphenoxy)-3-(3-{3-[(tert-butyloxycarbonyl)amino]oxetan-3-yl}phenyl)-1H-pyrazol-1-yl]acetic acid as a foam. Calcd (M+1)⁺: 534.5. Found: 534.8

Step 10:

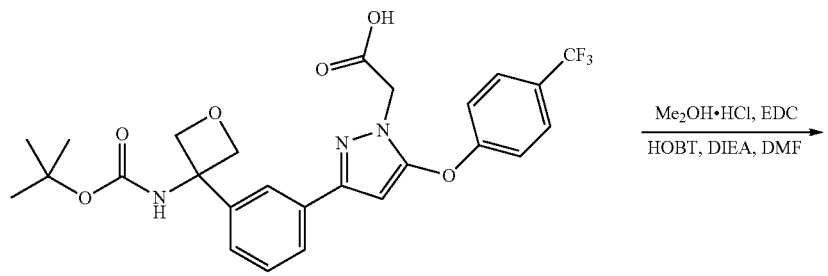

[5-(4-Trifluoromethylphenoxy)-3-(3-{3-[(tert-butyloxycarbonyl)amino]oxetan-3-yl}phenyl)-1H-pyrazol-1-yl]acetic acid (85 mg, 0.16 mmol), dimethylamine hydrochloride (26 mg, 0.32 mmol), EDC (46 mg, 0.24 mmol), HOBT (37 mg, 0.24 mmol), and diisopropylethylamine (0.11 mL, 0.64 mmol) were combined in 0.5 mL of DMF and the mixture was stirred at ambient temperature for 18 h. The mixture was diluted with EtOAc and washed with water and brine. The organic phase was dried over MgSO₄, filtered, and the solvent was removed under reduced pressure. The residue was chromatographed on a 12 g silica gel column using 0-5% MeOH:CHCl₃ over 15 min at 30 mL/min. Product-containing fractions were combined and the solvents were evaporated under reduced pressure to give tert-butyl [3-(3-{5-(4-trifluoromethylphenoxy)-1-[2-(dimethylamino)-2-oxoethyl]-1H-pyrazol-3-yl}phenyl)oxetan-3-yl]carbamate as a foam. Calcd (M+1)⁺: 561.6. Found: 561.0

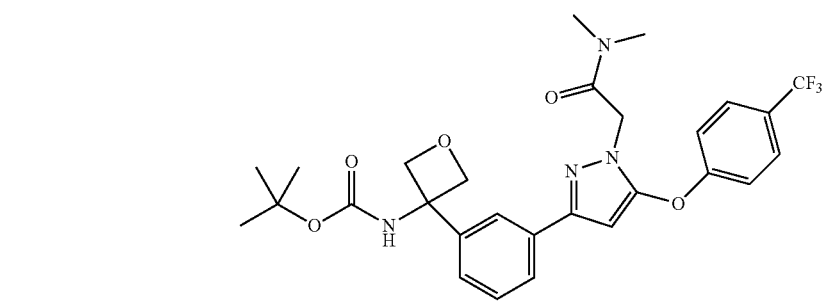

Step 11:

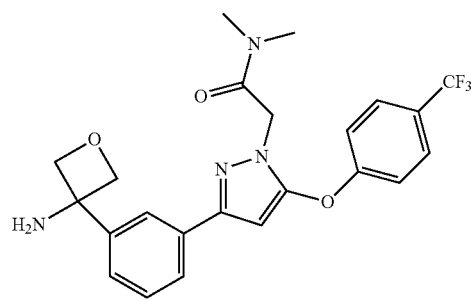

A stirred solution of tert-butyl [3-(3-{5-(4-trifluoromethylphenoxy)-1-[2-(dimethylamino)-2-oxoethyl]-1H-pyrazol-3-yl}phenyl)oxetan-3-yl]carbamate (70 mg, 0.13 mmol) in 2 mL of CH$_2$Cl$_2$ was cooled in an ice bath. To the solution was added 1 mL of TFA and the mixture was stirred for 1 h. The cooling bath was removed and the mixture was stirred at ambient temperature for 1 h. 10% Aqueous Na$_2$CO$_3$ solution was added and the mixture was extracted with CH$_2$Cl$_2$. The combined organic phases were dried over Na$_2$SO$_4$, filtered, and the solvent was removed under reduced pressure to give 2-{3-[3-(3-aminooxetan-3-yl)phenyl]-5-(4-trifluoromethylphenoxy)-1H-pyrazol-1-yl}-N,N-dimethylacetamide as an oil. Calcd (M+1)$^+$: 461.4. Found: 461.5

Step 12:

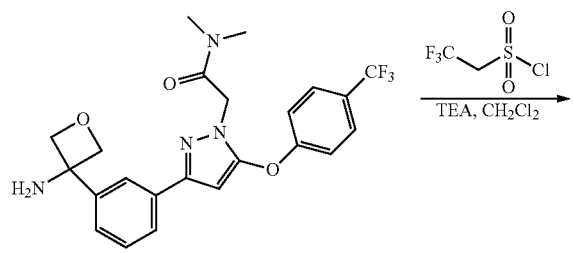

A stirred solution of 2-{3-[3-(3-aminooxetan-3-yl)phenyl]-5-(4-trifluoromethylphenoxy)-1H-pyrazol-1-yl}-N,N-dimethylacetamide (46 mg, 0.10 mmol) in 1 mL of CH$_2$Cl$_2$ was cooled in an ice bath. Triethylamine (0.021 mL, 0.15 mmol) was added, followed by trifluoroethylsulfonyl chloride (0.013 mL, 0.12 mmol), and the mixture was stirred for 30 min. Water was added and the mixture was extracted with CH$_2$Cl$_2$. The combined organic phases were washed with water and brine, then dried over Na$_2$SO$_4$, filtered, and the solvent was removed under reduced pressure. The residue was purified on a C18 reverse phase column using a gradient elution of 20-70% CH$_3$CN:H$_2$O with 0.1% TFA over 20 min at 20 mL/min. Fractions containing pure product were combined and the solvents were removed under reduced pressure to give 2-[5-(4-trifluoromethylphenoxy)-3-(3-{3-[(2,2,2-trifluoroethylsulfonyl)amino]oxetan-3-yl}phenyl)-1H-pyrazol-1-yl]-N,N-dimethylacetamide as a foam. Calcd (M+1)$^+$: 607.1444. Found: 607.1468. $^1$H NMR (400 MHz, CDCl$_3$) δ 7.75 (m, 2H), 7.64 (d, J=7, 2H), 7.44 (t, J=7, 1H), 7.35 (m, 2H), 7.28 (s, 1H), 6.38 (s, 1H), 6.04 (s, 1H), 5.04 (d, J=7, 2H), 4.98 (d, J=7, 2H), 4.94 (s, 2H), 3.09 (s, 3H), 2.97 (overlapping s and q, 5H).

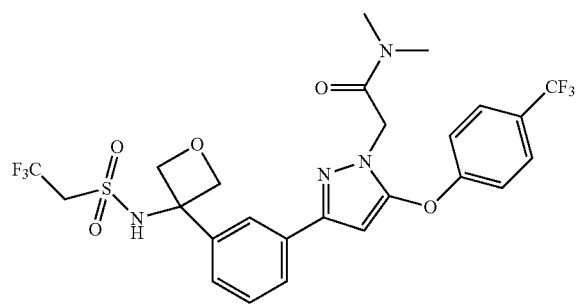 [SMILES: CN(C)C(=O)Cn1nc(-c2cccc(C3(NS(=O)(=O)CC(F)(F)F)COC3)c2)cc1Oc1ccc(C(F)(F)F)cc1]

The starting material for Examples 132 through 133 below was [5-(4-trifluoromethylphenoxy)-3-(3-{3-[(tert-butyloxycarbonyl)amino]oxetan-3-yl}phenyl)-1H-pyrazol-1-yl]acetic acid as described in step 9 of Example 131. This material was processed through to final product following procedures given in steps 10-12 of Example 131 using the appropriate amine in place of dimethylamine in step 10.

| # | Structure | Name | Calc Mass (M + 1)$^+$ | Exp Mass (M + 1)$^+$ |
|---|---|---|---|---|
| 132 | 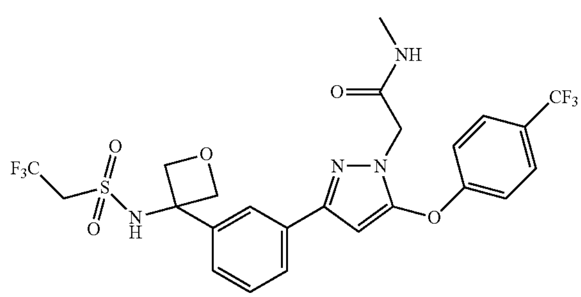 [SMILES: CNC(=O)Cn1nc(-c2cccc(C3(NS(=O)(=O)CC(F)(F)F)COC3)c2)cc1Oc1ccc(C(F)(F)F)cc1] | 2-[5-(4-trifluoromethylphenoxy)-3-(3-{3-[(2,2,2-trifluoroethylsulfonyl)amino]oxetan-3-yl}phenyl)-1H-pyrazol-1-yl]-N-methylacetamide | 593.1288 | 593.1315 |

| # | Structure | Name | Calc Mass (M + 1)+ | Exp Mass (M + 1)+ |
|---|-----------|------|---------------------|--------------------|
| 133 | 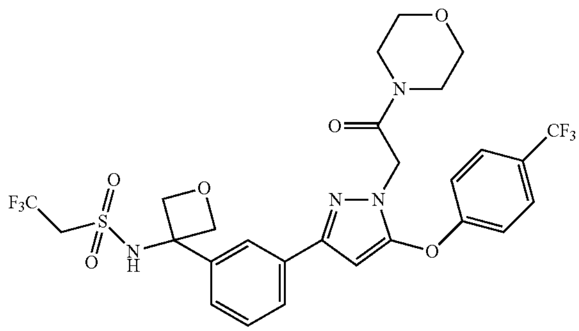 [SMILES: O=C(Cn1nc(-c2cccc(C3(NS(=O)(=O)CC(F)(F)F)COC3)c2)cc1Oc1ccc(C(F)(F)F)cc1)N1CCOCC1] | N-[3-(3-{5-(4-trifluoromethylphenoxy)-1-[2-oxo-2-(morpholin-4-yl)ethyl]-1H-pyrazol-3-yl}phenyl)oxetan-3-yl]-,2,2,2-trifluoroethanesulfonamide | 649.1550 | 649.1578 |

Example 134

N-(3-{3-[5-(4-trifluoromethylphenoxy)-1-(1,3-oxazol-4-ylmethyl)-1H-pyrazol-3-yl]phenyl}oxetan-3-yl)-2,2,2-trifluoroethanesulfonamide Step 1:

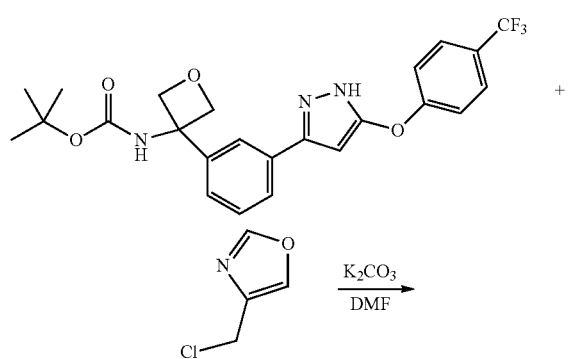

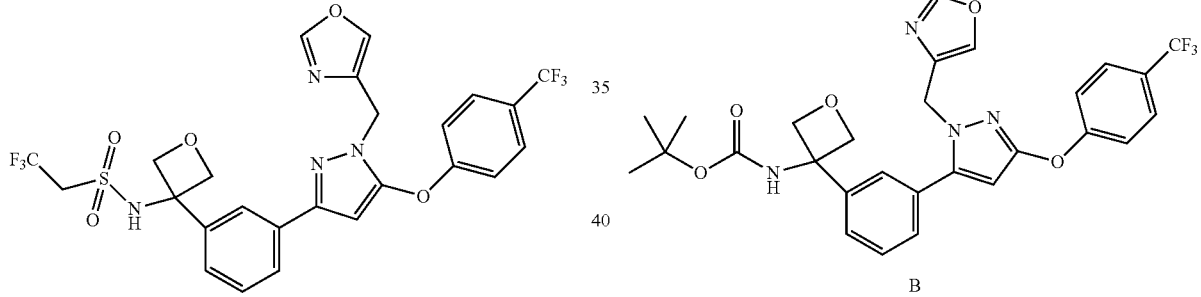

tert-Butyl {3-[3-(5-(4-trifluoromethylphenoxy)-1H-pyrazol-3-yl)phenyl]oxetan-3-yl}carbamate from Example 130, Step 7 (120 mg, 0.25 mmol), 4-chloromethyloxazole (119 mg, 1.0 mmol), and $K_2CO_3$ (155 mg, 1.1 mmol) in 0.6 mL of DMF were combined in a sealed tube and the stirred mixture was heated to 100° C. for 18 h. The mixture was cooled to ambient temperature and diluted with $CH_2Cl_2$. The mixture was washed with water and brine, then dried over $Na_2SO_4$, filtered, and the solvents were reduced under reduced pressure to give an oil. The residue was purified on a C18 column using a gradient elution of 20-100% $CH_3CN:H_2O$ with 0.1% TFA. Fractions containing the first eluting peak were combined and the solvents were removed under reduced pressure to give compound A, tert-butyl (3-{3-[5-(4-trifluoromethylphenoxy)-1-(1,3-oxazol-4-ylmethyl)-1H-pyrazol-3-yl]phenyl}oxetan-3-yl)carbamate, as a glass. Calcd 557.5. found: 557.8. $^1H$ NMR (400 MHz, $CDCl_3$) δ 7.88 (br s, 1H), 7.65 (m, 3H), 7.50 (d, J=7, 1H), 7.41 (t, J=7, 1H), 7.25 (d, J=7, 2H), 7.08 (s, 1H), 6.06 (s, 1H), 5.45 (s, 2H), 5.01 (br s, 2H), 4.89 (br d, 2H), 1.20 (br s, 9H). Fractions containing the second eluting peak were combined and the solvents were removed under reduced pressure to give compound B, tert-butyl (3-{3-[3-(4-trifluoromethylphenoxy)-1-(1,3-oxazol-4- ylmethyl)-1H-pyrazol-5-yl]phenyl}oxetan-3-yl)carbamate, as a glass. Calcd (M+1)⁺: 557.5. found: 557.9. ¹H NMR (400 MHz, CDCl₃) δ 7.45-7.775 (m, 6H), 7.25 (d, J=7, 2H), 7.16 (s, 1H), 5.98 (s, 1H), 5.85 (s, 2H), 4.99 (br 5, 2H), 4.87 (br d, 2H), 1.20 (br s, 9H).
Step 2:

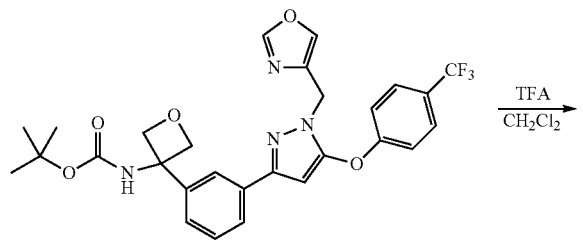

A stirred solution of tert-butyl (3-{3-[5-(4-trifluoromethylphenoxy)-1-(1,3-oxazol-4-ylmethyl)-1H-pyrazol-3-yl]phenyl}oxetan-3-yl)carbamate (48 mg, 0.086 mmol) in 0.6 mL of CH₂Cl₂ was cooled in an ice bath, and to the solution was added 0.6 mL of TFA. The solution was stirred for 1.5 h and then quenched with 10% Na₂CO₃. The organic phase was washed with water and brine, dried over Na₂SO₄, and the solvent was removed under reduced pressure to give 3-{3-[1-(1,3-oxazol-4-ylmethyl)-5-(4-trifluoromethylphenoxy)-1H-pyrazol-3-yl]phenyl}oxetan-3-amine as a glass. Calcd (M+1)⁺: 457.4. found: 457.1.
Step 3:

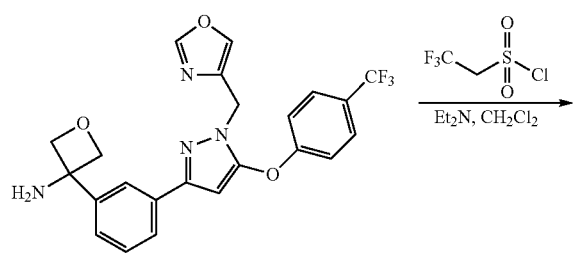

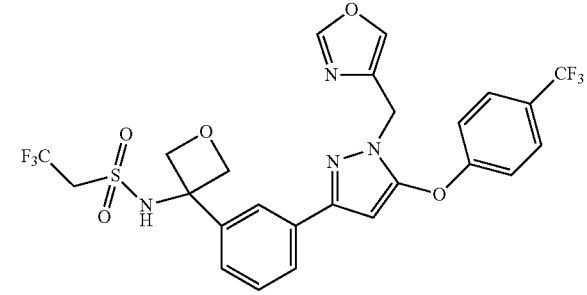 [SMILES: O=S(=O)(CC(F)(F)F)NC1(c2cccc(-c3cc(Oc4ccc(C(F)(F)F)cc4)n(Cc4cocn4)n3)c2)COC1]

A stirred solution of 3-{3-[1-(1,3-oxazol-4-ylmethyl)-5-(4-trifluoromethylphenoxy)-1H-pyrazol-3-yl]phenyl}oxetan-3-amine (35 mg, 0.077 mmol) in 1 mL of CH₂Cl₂ was cooled in an ice bath. To the solution was added TEA (21 uL, 0.15 mmol) and 2,2,2-trifluoroethylsulfonyl chloride (12 uL, 0.12 mmol) and the solution was stirred for 30 min. Water was added and the organic phase was washed with brine, died over Na₂SO₄, filtered, and the solvent was removed under reduced pressure. The residue was chromatographed on a 12 g silica gel column using 0-5% MeOH:CHCl₃ over 16 min at 30 mL/min. Product containing fractions were combined and the solvent was removed under reduced pressure to give N-(3-{3-[5-(4-trifluoromethylphenoxy)-1-(1,3-oxazol-4-ylmethyl)-1H-pyrazol-3-yl]phenyl}oxetan-3-yl)-2,2,2-trifluoroethanesulfonamide as a foam. Calcd (M+1)⁺: 603.1131. found 603.1153. ¹H NMR (400 MHz, CDCl₃) δ 7.80 (s, 1H), 7.78 (d, J=7, 1H), 7.65 (d, J=7, 2H), 7.61 (s, 1H), 7.49 (1, J=7, 1H), 7.37 (d, J=7, 2H), 7.28 (d, J=7, 2H), 7.09 (s, 1H), 6.08 (s, 1H), 6.05 (s, 1H), 5.44 (s, 2H), 5.23 (d, J=7, 2H), 5.05 (d, J=7, 2H), 3.03 (q, J=9, 2H).

Example 135

N-(3-{3-[3-(4-trifluoromethylphenoxy)-1-(1,3-oxazol-4-ylmethyl)-1H-pyrazol-5-yl]phenyl}oxetan-3-yl)-2,2,2-trifluoroethanesulfonamide

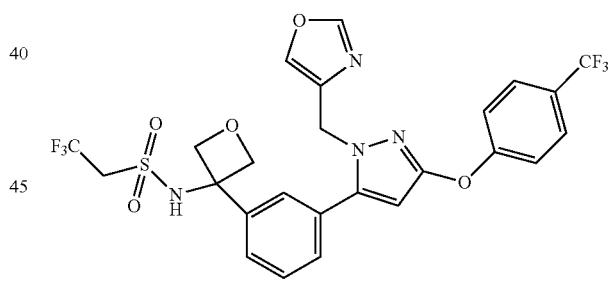

tert-Butyl (3-{3-[3-(4-trifluoromethylphenoxy)-1-(1,3-oxazol-4-ylmethyl)-1H-pyrazol-5-yl]phenyl}oxetan-3-yl)carbamate from Example 134, Step 1 was processed through to the title compound using procedures analogous to those given in steps 2 and 3 of Example 134. Calcd (M+1)⁺: 603.1131. found 603.1147. ¹H NMR (400 MHz, CDCl₃) δ 7.78 (s, 1H), 7.70 (s, 1H), 7.6 (m, 5H), 7.28 (d, J=7, 2H), 7.13 (s, 1H), 6.45 (s, 1H), 6.02 (s, 1H), 5.30 (s, 2H), 5.10 (d, J=7, 2H), 5.07 (d, J=7, 2H), 3.32 (q, J=9, 2H).

The starting material for Examples 136 through 142 below was tert-butyl {3-[3-(5-(4-trifluoromethylphenoxy)-1H-pyrazol-3-yl)phenyl]oxetan-3-yl}carbamate as described in Example 131, Step 7. This material was processed through to final product following procedures given in Example 134, Steps 1-3 using the appropriate halide in place of 4-chloromethyloxazole in step 1.

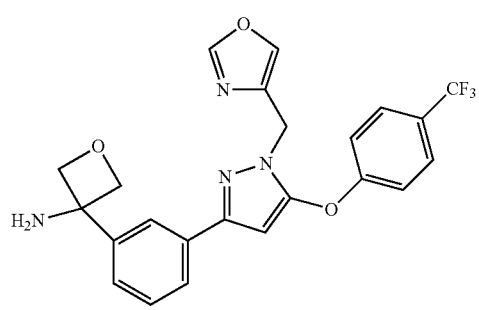

| # | Structure | Name | Calc Mass (M + 1)+ | Exp Mass (M + 1)+ |
|---|---|---|---|---|
| 136 | 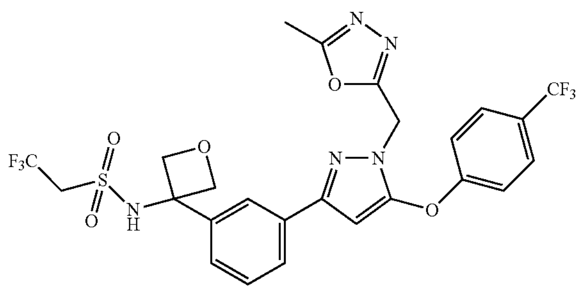 [SMILES: Cc1nnc(Cn2nc(-c3cccc(C4(NS(=O)(=O)CC(F)(F)F)COC4)c3)cc2Oc2ccc(C(F)(F)F)cc2)o1] | N-(3-{3-[5-(4-trifluoromethylphenoxy)-1-(5-methyl-1,3,4-oxadiazol-2-ylmethyl)-1H-pyrazol-3-yl]phenyl}oxetan-3-yl)-2,2,2-trifluoroethanesulfonamide | 618.1240 | 618.1260 |
| 137 | 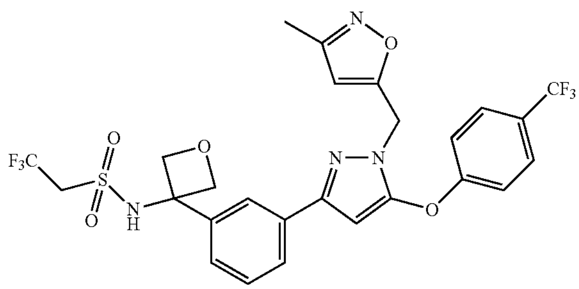 [SMILES: Cc1cc(Cn2nc(-c3cccc(C4(NS(=O)(=O)CC(F)(F)F)COC4)c3)cc2Oc2ccc(C(F)(F)F)cc2)on1] | N-(3-{3-[5-(4-trifluoromethylphenoxy)-1-(5-methyl-1,2-isoxazol-3-ylmethyl)-1H-pyrazol-3-yl]phenyl}oxetan-3-yl)-2,2,2-trifluoroethanesulfonamide | 617.1288 | 617.1287 |
| 138 | 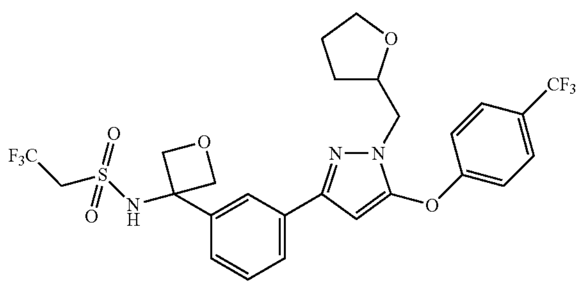 [SMILES: O=S(=O)(CC(F)(F)F)NC1(c2cccc(-c3cc(Oc4ccc(C(F)(F)F)cc4)n(CC4CCCO4)n3)c2)COC1] | N-(3-{3-[5-(4-trifluoromethylphenoxy)-1-(tetrahydrofuran-2-ylmethyl)-1H-pyrazol-3-yl]phenyl}oxetan-3-yl)-2,2,2-trifluoroethanesulfonamide | 606.1492 | 606.1489 |
| 139 | 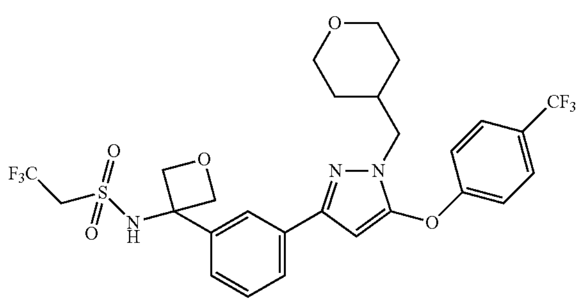 [SMILES: O=S(=O)(CC(F)(F)F)NC1(c2cccc(-c3cc(Oc4ccc(C(F)(F)F)cc4)n(CC4CCOCC4)n3)c2)COC1] | N-(3-{3-[5-(4-trifluoromethylphenoxy)-1-(tetrahydro-2H-pyran-4-ylmethyl)-1H-pyrazol-3-yl]phenyl}oxetan-3-yl)-2,2,2-trifluoroethanesulfonamide | 620.1648 | 620.1658 |
| 140 | 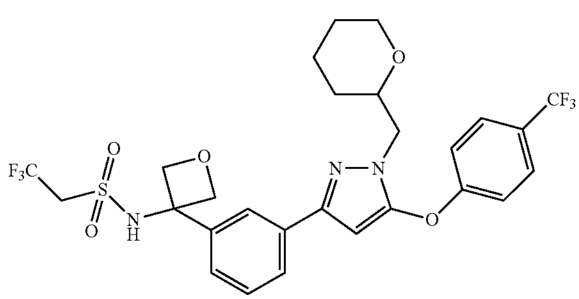 [SMILES: O=S(=O)(CC(F)(F)F)NC1(c2cccc(-c3cc(Oc4ccc(C(F)(F)F)cc4)n(CC4CCCCO4)n3)c2)COC1] | N-(3-{3-[5-(4-trifluoromethylphenoxy)-1-(tetrahydro-2H-pyran-4-ylmethyl)-1H-pyrazol-2-yl]phenyl}oxetan-3-yl)-2,2,2-trifluoroethanesulfonamide | 620.1648 | 620.1636 |

| # | Structure | Name | Calc Mass (M + 1)+ | Exp Mass (M + 1)+ |
|---|---|---|---|---|
| 141 | 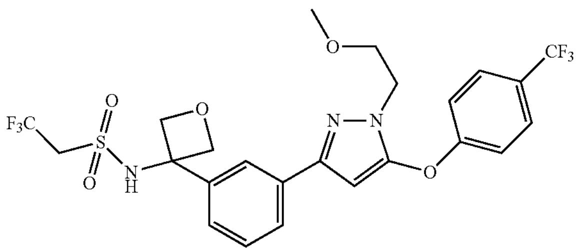 [SMILES: COCCn1nc(-c2cccc(C3(NS(=O)(=O)CC(F)(F)F)COC3)c2)cc1Oc1ccc(C(F)(F)F)cc1] | N-(3-{3-[5-(4-trifluoromethylphenoxy)-1-(2-methoxyethyl)-1H-pyrazol-2-yl]phenyl}oxetan-3-yl)-2,2,2-trifluoroethanesulfonamide | 580.5 | 580.6 |
| 142 | 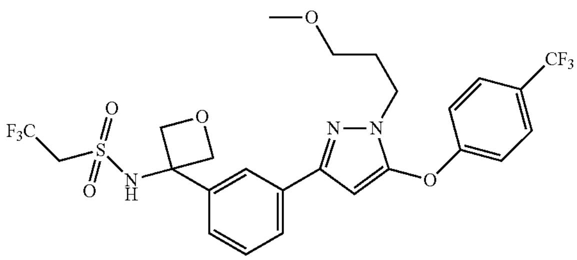 [SMILES: COCCCn1nc(-c2cccc(C3(NS(=O)(=O)CC(F)(F)F)COC3)c2)cc1Oc1ccc(C(F)(F)F)cc1] | N-(3-{3-[5-(4-trifluoromethylphenoxy)-1-(3-methoxypropyl)-1H-pyrazol-2-yl]phenyl}oxetan-3-yl)-2,2,2-trifluoroethanesulfonamide | 594.1492 | 594.1482 |

Biological Activity

Assays to determine the biological activity of the compounds of the invention are described as follows:

APP Processing (Assay Quantitates Secreted Aβ Analytes from Cell Lines):

The effect of compounds on the abundance of Aβ40 and Aβ42 peptides generated from SH-SY5Y cells expressing amyloid β protein (SP4CT cells) are determined by an AlphaLisa™ assay. Analogous to an ELISA assay, generation of in this AlphaLisa™ assay requires "donor" and "acceptor" beads to be brought in close proximity by specific antibody recognition of either Aβ40 or Aβ42 peptides. The assay is accomplished by removing media from compound-treated SP4CT cells to two different microplates, followed by the addition of donor beads conjugated with streptavidin binding a biotinylated anti-amyloid β monocolonal antibody (clone 4G8). Acceptor beads directly conjugated with anti-Aβ40 monoclonal antibody (G210) are added to one microplate and anti-Aβ42 monoclonal antibody (12F4) acceptor beads were added to the other. Abundance of Aβ40 and Aβ42 is directly proportional to the luminescent signal generated following excitation of donor beads by laser light.

Notch Processing: (Assay Quantitates Notch Intracellular Domain Release in Cell Lines):

A "split-luciferase" assay is used to measure inhibition of gamma secretase-dependent cleavage of the Notch protein. In this assay, HeLa cells are made to express a Notch protein lacking its extracellular domain (NotchΔE) fused to an N-terminal fragment of luciferase. The same cells also expressed a C-terminal fragment of luciferase fused to the immunoglobulin kappa recombination signal sequence binding protein (RBP). Upon NotchΔE cleavage by gamma secretase, a Notch intracellular domain (NICD)-N terminal luciferase protein is generated which translocates to the nucleus and binds the RBP-C terminal luciferase fusion, bringing two independently nonfunctional halves of luciferase together to form a functional luciferase enzyme. The activity of luciferase in these cells is directly proportional to the amount of gamma secretase-cleaved Notch. Luciferase activity is determined by the standard techniques of luciferin addition to lysed cells and measurement of total luminescence.

ICD Transactivation (Assay Quantitates Intracellular Domain Release of a Panel of γ-Secretase Substrates in Cell Lines)

A Firefly luciferase based transactivation assay is used to measure inhibition of ε/S3-site cleavage of γ-secretase substrates. This assay involves the use of chimeric substrates harboring a GAL4/VP16 (GVP) transactivation domain fused to the intracellular domain (ICD): APP-GVP, NotchΔE-GVP, E-cadherin-GVP and CD44-GVP. Upon cleavage and release of ICDs, the GVP domain drives the expression of the luciferase gene under the control of the UAS promoter. In this assay, HEK cells are transiently co-transfected with the chimeric substrate along with a UAS promoter driven luciferase and β-galactosidase (transfection control). Upon cleavage by γ-secretase, the released ICD-GVP translocates to the nucleus to drive the expression of the UAS-luciferase gene. The activity of luciferase in these cells is directly proportional to the amount of γ-secretase-cleaved ICDs. Luciferase activity is determined by the standard techniques of luciferin addition to lysed cells and measurement of total luminescence. In addition, to account for the differences in transfection efficiencies an absorbance based β-galactosidase enzyme assay is performed to normalize the luminescence read-out.

Assessing Full Length γ-Secretase Substrates (Assay Qualitatively Assesses the Processing of a Panel of γ-Secretase Substrates)

To examine the effect of compounds on γ-secretase activity against other substrates, four HEK 293 stable cell lines overexpressing one of the following type I membrane proteins: CD43, CD44, E-Cadherin and SCN2b with a C-terminal V5 tag, are generated. Cells are plated and treated overnight with titrated compound and the phorbol ester, TPA. Since all of the proteins undergo regulated membrane proteolysis characterized by an initial ectodomain shedding event followed by the intramembraneous cleavage of the C-terminal fragment (CTF) by γ-secretase, TPA induces the initial cleavage event producing the substrate for γ-secretase. The effect of compounds on γ-secretase activity in relation to these substrates is measured by tracking the processing of the V5 tagged CTFs by Western blot analysis. Accumulation of the CTFs indicates inhibition of γ-secretase activity.

In vitro APP Processing (Assay Quatitates Aβ Analytes Generated from a Recombinant APPC100Flag Substrate Incubated with Semi-Purified γ-Secretase)

The effect of compounds on the abundance of Aβ40 and Aβ42 peptides generated from exogenous C100Flag substrate by semi-purified γ-secretase is determined by MESO Scale ELISA. Generation of signal in this MESO Scale assay requires an anti-amyloid monoclonal antibody (clone 4G8) conjugated with streptavidin to bind to a biotin-coated plate. Specific [Ru(bpy)3]2+-labeled monoclonal antibodies for either Aβ40 (G210) or Aβ42 (12F4) subsequently generate an electrochemiluminescence signal upon electrochemical stimulation. The assay is accomplished by incubating compound, C100Flag substrate and CHAPSO-solubilized P2 membranes from HeLa cells or brains of mouse, rat, or dog. The reaction is then transferred to two different biotinylated microplates for detection of either Aβ40 or Aβ42.

In Vitro Notch Processing (Assay Qualitatively Assess Notch Intracellular Domain Generation From Recombinant NotchΔE100Flag Substrate Incubated with Semi-Purified γ-Secretase)

In an analogous manner, Notch processing can be monitored using the same method as the C100Flag in vitro assay but by substituting substrate for N100Flag. A polyclonal biotin-conjugated anti-DYKDDDDK antibody is used as capture antibody while a polyclonal [Ru(bpy)3]2+-labeled cleaved Notch1 antibody was used to detect NICD.

Pharmacokinetics

Pharmacokinetic parameters are determined in Sprague Dawley rats, Beagle dogs or Rhesus monkeys by dosing the compounds intravenously (IV) or orally (PO). A dose of 0.25 mg/kg is administered either IV or PO to each subject with a dosing solution of 0.25 mg/ml in a 30:70 v/v mixture of PEG400:40% Captisol®. Plasma samples are collected at 5 min. (IV only), 15 min., 30 min., 1 h, 2 h, 4 h, 6 h, 8 h, 24 h, 48 h, 72 h, 96 h, 120 h, 144 h, and 168 h. Samples are analyzed by LC-MS/MS (API5000™) to determine the concentration in plasma. Briefly, 50 µL plasma is precipitated with 200 µL acetonitrile containing an appropriate internal standard. Samples are filtered, 500 pt of water is added to each sample and 10 µl, of this is injected on a $C_{18}$ column (2.0 mm×30 mm, 3 µm particle size) and eluted using a gradient LC method with water containing 0.1% formic acid as the aqueous mobile phase, and acetonitrile containing 0.1% formic acid as the organic phase. Electrospray ionization with multiple reaction monitoring is used for MS/MS detection. Plasma concentration of the compounds is determined using a standard curve that was prepared similar to the samples in the respective matrix. Non-compartmental analysis is performed using Watson 7.2 to generate the PK parameters.

Results

APP Processing:

Examples 1-142 inhibited the production of Aβ40 and Aβ42 peptides in SH-SY5Y cells expressing amyloid β protein (SP4CT cells) with $IC_{50}$'s of <200 nM.

Phamacokinetics:

| Structure | | Rat Cl (mL/min/kg) | AUC(Norm)$_{(0-x)}$ (µM * h * kg/mg) | $t_{1/2}$ (h) | % F |
|---|---|---|---|---|---|
| Example 2 from WO 2004/089911 A1 | [structure] | 43 | 0.79 | 2.3 | 9 |
| Example 23 from WO 2004/089911 A1 | [structure] | 120 | 0.25 | 5.4 | ND |
| Example 27 from WO 2004/089911 A1 | [structure] | 35 | 0.92 | 4.8 | 28 |

-continued

| Structure | Rat Cl (mL/min/kg) | AUC(Norm)$_{(0-x)}$ (μM * h * kg/mg) | $t_{1/2}$ (h) | % F |
|---|---|---|---|---|
| Example 53 | 1 | 35 | 16 | 70 |
| Example 19 | 31 | 0.96 | 9 | 75 |
| Example 96 | 41 | 0.09 | 2.8 | 12 |

What is claimed is:

1. A compound of formula I:

or a pharmaceutically acceptable salt thereof, wherein:
A represents —C($R^4$)($R^5$)— and B represent H, or A and B are joined together to form the following group:

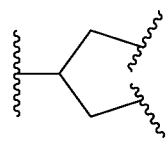 [SMILES: *CC(*)C*]

Y and Z independently represent $CR^{11}$ or N, wherein $R^{11}$ is H or halogen;

X represents a bond, O or $NR^2$;

$R^1$ represents a linear, branched or cyclic, or combination thereof, hydrocarbon group of 1-10 carbon atoms, which is optionally substituted with up to 3 halogen atoms; or when X represents $NR^2$, $R^1$ and $R^2$ together may complete a heterocyclic ring of up to 6 members which optionally bears up to 3 substituents independently selected from halogen, $CF_3$, $CHF_2$, $CH_2F$, $NO_2$, CN, $OCF_3$, $C_{1-6}$alkyl and $C_{1-6}$alkoxy;

$R^2$ represents H or $C_{1-4}$alkyl, or together with $R^1$ completes a heterocyclic ring as defined above;

$R^3$ represents H or $C_{1-4}$alkyl;

$R^4$ represents $C_{1-6}$alkyl, $R^5$ represents H or $C_{1-6}$alkyl;

or $R^4$ and $R^5$ may be joined together with the atom to which they are attached to form a spirocyclic ring of 3, 4 or 5 atoms, said ring optionally containing a heteroatom selected from O, S or N;

$R^6$ is bonded to one of the nitrogen atoms of the pyrazole ring and represents a hydrocarbon group of 1-5 carbon atoms which is optionally substituted with 1-3 substituents independently selected from $R^8$;

R⁷ represents H, halogen, CN, formyl, phenylethynyl or C₁₋₆alkyl;

Ar represents phenyl or 6-membered heteroaryl, either of which bears 0-3 substituents independently selected from R⁸;

R⁸ is selected from the group consisting of: halogen, OH, CN, R¹⁰, OR⁹, SR¹⁰, SO₂R¹⁰, SO₂N(R⁹)₂, COR⁹, CO₂R⁹, CON(R⁹)₂, N(R⁹)₂, NO₂, NR⁹COR¹⁰, NR⁹CO₂R⁹, NR⁹CH₂CO₂R⁹, NR⁹SO₂R¹⁰, —C₁₋₄alkyl-N(R⁹)₂, —C₁₋₄alkyl-NR⁹COR¹⁰, —C₁₋₄alkyl-NR⁹CO₂R⁹ and —C₁₋₄alkyl-NR⁹CH₂CO₂R⁹;

each R⁹ is independently selected from: (1) H, C₁₋₆alkyl, C₃₋₁₀cycloalkyl, C₃₋₁₀cycloalkylC₁₋₄alkyl, C₃₋₁₀cycloalkenyl or C₃₋₁₀cycloalkenylC₁₋₄alkyl, any of which except H optionally bear up to 4 halogen atoms or with OH, CN, CF₃ and C₁₋₄alkoxy, or both; (2) phenyl, benzyl, 5- or 6-membered monocyclic heteroaryl optionally bridged with a methylene or a 9- or 10-membered bicyclic heteroaryl optionally bridged with a methylene, any of which optionally bear up to 3 substituents independently selected from halogen, OH, CN, CF₃, C₁₋₄alkyl, C₃₋₆cycloalkyl, phenyl, C₁₋₄alkoxy, amino, C₁₋₄alkylamino and di(C₁₋₄-alkyl)amino; and (3) a nonaromatic or partially aromatic mono- or bicyclic heterocyclic system of up to 10 ring atoms, optionally bridged with a methylene and optionally bearing up to 3 substituents independently selected from halogen, OH, oxo, CN, CF₃, C₁₋₄alkyl, C₃₋₆cycloalkyl, phenyl, a 5- or 6-membered monocyclic heteroaryl, C₁₋₄alkoxy, acetyl, amino, C₁₋₄alkylamino and di(C₁₋₄alkyl)amino; or when two R⁹ groups are attached to the same nitrogen atom they may be joined together with the nitrogen atom to complete a mono- or bicyclic heterocyclic ring of up to 10 members which optionally bears up to 3 substituents independently selected from halogen, CF₃, CHF₂, CH₂F, NO₂, CN, OCF₃, acetyl, formyl, C₁₋₆alkyl and C₁₋₆alkoxy; and R¹⁰ has the same definition as R⁹ except that R¹⁰ is not H.

2. The compound according to claim 1 wherein R⁶ is bonded to one of the nitrogen atoms of the pyrazole ring and represents a hydrocarbon group of 1-5 carbon atoms which is optionally substituted with up to 3 halogen atoms or hydroxy.

3. The compound according to claim 2 wherein Ar represent phenyl, which bears 0-3 substituents independently selected from R⁸.

4. The compound according to claim 3 wherein Ar represents 4-CF₃-phenyl.

5. The compound according to claim 2 wherein R⁶ is bonded to one of the nitrogen atoms of the pyrazole ring and represents ethyl.

6. The compound according to claim 2 wherein A represents —C(R⁴)(R⁵)— and B represent H.

7. The compound according to claim 6 wherein R⁴ and R⁵ are methyl.

8. The compound according to claim 6 wherein R⁴ and R⁵ are joined together with the atom to which they are attached to form cyclopropyl, cyclobutyl or oxetanyl.

9. The compound according to claim 2 wherein A and B are joined together to form the following group:

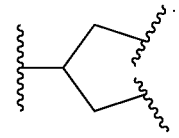 [SMILES: *CC(*)C*]

10. The compound according to claim 2 wherein X represents a bond.

11. The compound according to claim 10 wherein R¹ represent CF₃—CH₂—.

12. The compound according to claim 2 wherein X represents NR².

13. The compound according to claim 2 wherein Y and Z each represent CH.

14. The compound according to claim 2 wherein:
Y and Z each represent CH;
Ar represent phenyl, which bears 0-3 substituents independently selected from R⁸;
R³ represents H;
R⁶ is bonded to one of the nitrogen atoms of the pyrazole ring and represents ethyl;
R⁷ represents H;
A represents —C(R⁴)(R⁵)— and B represent H;
R⁴ and R⁵ are methyl or R⁴ and R⁵ are joined together with the atom to which they are attached to form cyclopropyl, cyclobutyl or oxetanyl; and
X represents a bond or NR².

15. The compound according to claim 1 wherein:
Y and Z each represent CH;
Ar represent phenyl, which bears 0-3 substituents independently selected from R⁸;
R³ represents H;
R⁷ represents H;
A represents —C(R⁴)(R⁵)— and B represent H;
R⁴ and R⁵ are methyl or R⁴ and R⁵ are joined together with the atom to which they are attached to form cyclopropyl, cyclobutyl or oxetanyl; and
X represents a bond or NR².

16. A compound selected from the following group:
N-[1-(3-{1-ethyl-5-[4-(trifluoromethyl)phenoxy]-1H-pyrazol-3-yl}phenyl)-1-methylethyl]-2,2,2-trifluoroethanesulfonamide;
1-cyclobutyl-N-[1-(3-{1-ethyl-5-[4-(trifluoromethyl)phenoxy]-1H-pyrazol-3-yl}phenyl)-1-methylethyl]methanesulfonamide;
N-cyclobutyl-N'-[1-(3-{1-ethyl-5-[4-(trifluoromethyl)phenoxy]-1H-pyrazol-3-yl}phenyl)-1-methylethyl]sulfamide;
N-[1-(3-{1-ethyl-5-[4-(trifluoromethyl)phenoxy]-1H-pyrazol-3-yl}phenyl)-1-methylethyl]-N'-(2,2,2-trifluoroethyl)sulfamide;
N-[1-(3-{1-ethyl-5-[2-fluoro-4-(trifluoromethyl)phenoxy]-1H-pyrazol-3-yl}phenyl)-1-methylethyl]-2,2,2-trifluoroethanesulfonamide;
N-[1-(3-{1-ethyl-5-[4-(trifluoromethyl)phenoxy]-1H-pyrazol-3-yl}phenyl)-1-methylethyl]-2,2,2-trifluoroethanesulfonamide;
N-(1-{3-[1-ethyl-5-(2-fluorophenoxy)-1H-pyrazol-3-yl]phenyl}-1-methylethyl)-2,2,2-trifluoroethanesulfonamide;

N-[1-(3-{1-ethyl-5-[4-(trifluoromethyl)phenoxy]-1H-pyrazol-3-yl}phenyl)-1-methylethyl]-N'-propylsulfamide;
N-[1-(3-{1-ethyl-5-[4-(trifluoromethyl) phenoxy]-1H-pyrazol-3-yl}phenyl)-1-methylethyl]-N'-isobutylsulfamide;
N-[1-(3-{1-ethyl-5-[4-(trifluoromethyl)phenoxy]-1H-pyrazol-3-yl}phenyl)-1-methylethyl]-N'-methylsulfamide;
N-[1-(3-{1-ethyl-5-[4-(trifluoromethyl)phenoxy]-1H-pyrazol-3-yl}phenyl)-1-methylethyl]pyrrolidine-1-sulfonamide;
N-[1-(3-{1-ethyl-5-[4-(trifluoromethyl)phenoxy]-1H-pyrazol-3-yl}phenyl)-1-methylethyl]cyclopropanesulfonamide;
N-cyclopentyl-N'-[1-(3-{1-ethyl-5-[4-(trifluoromethyl)phenoxy]-1H-pyrazol-3-yl}phenyl)-1-methylethyl]sulfamide;
N'-[1-(3-{1-ethyl-5-[4-(trifluoromethyl)phenoxy]-1H-pyrazol-3-yl}phenyl)-1-methylethyl]-N,N-dimethylsulfamide;
N-[1-(3-{1-ethyl-5-[4-(trifluoromethyl)phenoxy]-1H-pyrazol-3-yl}-5-fluorophenyl)-1-methylethyl]-2,2,2-trifluoroethanesulfonamide;
N-cyclobutyl-N'-[1-(3-{1-ethyl-3-[4-(trifluoromethyl)phenoxy]-1H-pyrazol-5-yl}phenyl)-1-methylethyl]sulfamide;
N-[1-(3-{1-ethyl-3-[4-(trifluoromethyl)phenoxy]-1H-pyrazol-5-yl}phenyl)-1-methylethyl]-N'-isobutylsulfamide;
N-cyclopentyl-N'-[1-(3-{1-ethyl-3-[4-(trifluoromethyl)phenoxy]-1H-pyrazol-5-yl}phenyl)-1-methylethyl]sulfamide
N-[1-(3-{1-ethyl-3-[4-(trifluoromethyl)phenoxy]-1H-pyrazol-5-yl}phenyl)-1-methylethyl]-N'-(2,2,2-trifluoroethyl)sulfamide;
N-[1-(3-{1-ethyl-3-[4-(trifluoromethyl)phenoxy]-1H-pyrazol-5-yl}phenyl)-1-methylethyl]-2,2,2-trifluoroethanesulfonamide;
N-[1-(3-{1-ethyl-3-[2-fluoro-4-(trifluoromethyl)phenoxy]-1H-pyrazol-5-yl}phenyl)-1-methylethyl]-2,2,2-trifluoroethanesulfonamide;
N-[1-(3-{3-[(6-chloropyridin-3-yl)oxy]-1-ethyl-1H-pyrazol-5-yl}phenyl)-1-methylethyl]-2,2,2-trifluoroethanesulfonamide;
N-[1-(3-{1-ethyl-3-[4-(trifluoromethyl)phenoxy]-1H-pyrazol-5-yl}phenyl)-1-methylethyl]-N'-propylsulfamide;
N-[1-(3-{1-ethyl-3-[4-(trifluoromethyl)phenoxy]-1H-pyrazol-5-yl}phenyl)-1-methylethyl]-N'-methylsulfamide;
N'-[1-(3-{1-ethyl-3-[4-(trifluoromethyl)phenoxy]-1H-pyrazol-5-yl}phenyl)-1-methylethyl]-N,N-dimethylsulfamide;
N-[1-(3-{1-ethyl-3-[4-(trifluoromethyl)phenoxy]-1H-pyrazol-5-yl}phenyl)-1-methylethyl]pyrrolidine-1-sulfonamide;
N-[1-(3-{1-ethyl-3-[4-(trifluoromethyl)phenoxy]-1H-pyrazol-5-yl}phenyl)-1-methylethyl]piperidine-1-sulfonamide;
N-[1-(3-{1-ethyl-5-[4-(trifluoromethyl)phenoxy]-1H-pyrazol-3-yl}phenyl)cyclopropyl]-2,2,2-trifluoroethanesulfonamide;
N-cyclopentyl-N'-[1-(3-{1-ethyl-3-[4-(trifluoromethyl)phenoxy]-1H-pyrazol-5-yl}phenyl)cyclopropyl]sulfamide;
N-[1-(3-{1-ethyl-3-[4-(trifluoromethyl)phenoxy]-1H-pyrazol-5-yl}phenyl)cyclopropyl]-N'-isobutylsulfamide;
N-[1-(3-{1-ethyl-3-[4-(trifluoromethyl)phenoxy]-1H-pyrazol-5-yl}phenyl)cyclopropyl]-2,2,2-trifluoroethanesulfonamide;
N-{1-[3-(1-ethyl-3-{[5-(trifluoromethyl)pyridin-2-yl]oxy}-1H-pyrazol-5-yl)phenyl]cyclopropyl}-2,2,2-trifluoroethanesulfonamide;
N-[1-(3-{1-ethyl-3-[4-(trifluoromethyl)phenoxy]-1H-pyrazol-5-yl}phenyl)cyclopropyl]-N'-propylsulfamide;
N-[1-(3-{1-ethyl-3-[4-(trifluoromethyl)phenoxy]-1H-pyrazol-5-yl}phenyl)cyclopropyl]-N'-methylsulfamide;
N-cyclopentyl-N'-[1-(3-{1-ethyl-5-[4-(trifluoromethyl)phenoxy]-1H-pyrazol-3-yl}phenyl)cyclopropyl]sulfamide;
N-[1-(3-{1-ethyl-5-[4-(trifluoromethyl)phenoxy]-1H-pyrazol-3-yl}phenyl)cyclopropyl]-N'-(2,2,2-trifluoroethyl)sulfamide;
1-cyclobutyl-N-[1-(3-{1-ethyl-5-[4-(trifluoromethyl)phenoxy]-1H-pyrazol-3-yl}phenyl)cyclopropyl]methanesulfonamide;
N-[1-(3-{1-ethyl-5-[4-(trifluoromethyl)phenoxy]-1H-pyrazol-3-yl}phenyl)cyclopropyl]ethanesulfonamide;
N-{1-[3-(5-{[3-chloro-5-(trifluoromethyl)pyridin-2-yl]oxy}-1-ethyl-1H-pyrazol-3-yl)phenyl]cyclopropyl}-2,2,2-trifluoroethanesulfonamide;
N-{1-[3-(1-ethyl-5-{[6-(trifluoromethyl)pyridin-3-yl]oxy}-1H-pyrazol-3-yl)phenyl]cyclopropyl}-2,2,2-trifluoroethanesulfonamide;
N-{1-[3-(1-ethyl-5-{[5-(trifluoromethyl)pyridin-2-yl]oxy}-1H-pyrazol-3-yl)phenyl]cyclopropyl}-N'-(2,2,2-trifluoroethyl)sulfamide;
1-cyclobutyl-N-{1-[3-(1-ethyl-5-{[5-(trifluoromethyl)pyridin-2-yl]oxy}-1H-pyrazol-3-yl)phenyl]cyclopropyl}methanesulfonamide;
N-cyclobutyl-N'-{1-[3-(1-ethyl-5-{[5-(trifluoromethyl)pyridin-2-yl]oxy}-1H-pyrazol-3-yl)phenyl]cyclopropyl}sulfamide;
N-{1-[3-(1-ethyl-5-{[5-(trifluoromethyl)pyridin-2-yl]oxy}-1H-pyrazol-3-yl)phenyl]cyclopropyl}-2,2,2-trifluoroethanesulfonamide;
N-{1-[3-(1-ethyl-5-{[5-(trifluoromethyl)pyridin-2-yl]oxy}-1H-pyrazol-3-yl)phenyl]cyclopropyl}-N'-methylsulfamide;
N-[1-(3-{1-ethyl-5-[4-(trifluoromethyl)phenoxy]-1H-pyrazol-3-yl}phenyl)cyclopropyl]-N'-propylsulfamide;
N-[1-(3-{1-ethyl-5-[4-(trifluoromethyl)phenoxy]-1H-pyrazol-3-yl}phenyl)cyclopropyl]-N'-isobutylsulfamide;
N-[1-(3-{1-ethyl-5-[4-(trifluoromethyl)phenoxy]-1H-pyrazol-3-yl}phenyl)cyclopropyl]-N'-methylsulfamide;
N-[1-(3-{1-ethyl-5-[(5-fluoropyrimidin-2-yl)oxy]-1H-pyrazol-3-yl}phenyl)cyclopropyl]-2,2,2-trifluoroethanesulfonamide;
N-(1-{3-[1-ethyl-5-(pyridin-4-yloxy)-1H-pyrazol-3-yl]phenyl}cyclopropyl)-2,2,2-trifluoroethanesulfonamide;
N-[1-(6-{1-ethyl-5-[4-(trifluoromethyl)phenoxy]-1H-pyrazol-3-yl}pyridin-2-yl)cyclopropyl]-2,2,2-trifluoroethanesulfonamide;
N-[1-(5-{1-ethyl-5-[4-(trifluoromethyl)phenoxy]-1H-pyrazol-3-yl}pyridin-3-yl)cyclopropyl]-2,2,2-trifluoroethanesulfonamide;

N-(1-{3-[1-ethyl-3-(4-fluorophenoxy)-1H-pyrazol-5-yl]phenyl}-1-methylethyl)-2,2,2-trifluoroethanesulfonamide;

N-cyclobutyl-N'-(1-{3-[1-ethyl-3-(4-fluorophenoxy)-1H-pyrazol-5-yl]phenyl}-1-methylethyl)sulfamide;

N-(1-{3-[1-ethyl-3-(4-fluorophenoxy)-1H-pyrazol-5-yl]phenyl}-1-methylethyl)-N'-(2,2,2-trifluoroethyl)sulfamide;

N-(1-{3-[1-ethyl-5-(4-fluorophenoxy)-1H-pyrazol-3-yl]phenyl}-1-methylethyl)-2,2,2-trifluoroethanesulfonamide;

N-{1-[3-(1-ethyl-5-phenoxy-1H-pyrazol-3-yl)phenyl]-1-methylethyl}-2,2,2-trifluoroethanesulfonamide;

N-(1-{3-[1-ethyl-5-(4-isopropylphenoxy)-1H-pyrazol-3-yl]phenyl}-1-methylethyl)-2,2,2-trifluoroethanesulfonamide;

N-(1-{3-[1-ethyl-5-(4-methylphenoxy)-1H-pyrazol-3-yl]phenyl}-1-methylethyl)-2,2,2-trifluoroethanesulfonamide;

N-(1-{3-[5-(4-tert-butylphenoxy)-1-ethyl-1H-pyrazol-3-yl]phenyl}-1-methylethyl)-2,2,2-trifluoroethanesulfonamide;

N-(1-{3-[1-ethyl-5-(4-formylphenoxy)-1H-pyrazol-3-yl]phenyl}-1-methylethyl)-2,2,2-trifluoroethanesulfonamide;

N-[1-(3-{1-ethyl-5-[4-(hydroxymethyl)phenoxy]-1H-pyrazol-3-yl}phenyl)-1-methylethyl]-2,2,2-trifluoroethanesulfonamide;

N-[1-(3-{1-ethyl-5-[4-(fluoromethyl)phenoxy]-1H-pyrazol-3-yl}phenyl)-1-methylethyl]-2,2,2-trifluoroethanesulfonamide;

N-[1-(3-{5-[4-(difluoromethyl)phenoxy]-1-ethyl-1H-pyrazol-3-yl}phenyl)-1-methylethyl]-2,2,2-trifluoroethanesulfonamide;

N-[1-(3-{1-ethyl-5-[4-(1-hydroxyethyl)phenoxy]-1H-pyrazol-3-yl}phenyl)-1-methylethyl]-2,2,2-trifluoroethanesulfonamide;

N-[1-(3-{1-ethyl-5-[4-(1-hydroxy-2-methylpropyl)phenoxy]-1H-pyrazol-3-yl}phenyl)-1-methylethyl]-2,2,2-trifluoroethanesulfonamide;

N-[1-(3-{1-ethyl-5-[4-(1-hydroxypropyl)phenoxy]-1H-pyrazol-3-yl}phenyl)-1-methylethyl]-2,2,2-trifluoroethanesulfonamide;

N-[1-(3-{1-ethyl-5-[4-(1-fluoroethyl)phenoxy]-1H-pyrazol-3-yl}phenyl)-1-methylethyl]-2,2,2-trifluoroethanesulfonamide;

N-(1-{3-[5-(4-acetylphenoxy)-1-ethyl-1H-pyrazol-3-yl]phenyl}-1-methylethyl)-2,2,2-trifluoroethanesulfonamide;

N-[1-(3-{1-ethyl-5-[4-(1-hydroxy-1-methylethyl)phenoxy]-1H-pyrazol-3-yl}phenyl)-1-methylethyl]-2,2,2-trifluoroethanesulfonamide;

N-[1-(3-{1-ethyl-5-[4-(2,2,2-trifluoro-1-hydroxyethyl)phenoxy]-1H-pyrazol-3-yl}phenyl)-1-methylethyl]-2,2,2-trifluoroethanesulfonamide;

N-[1-(3-{1-ethyl-5-[4-(1,2,2,2-tetrafluoroethyl)phenoxy]-1H-pyrazol-3-yl}phenyl)-1-methylethyl]-2,2,2-trifluoroethanesulfonamide;

N-[1-(3-{1-ethyl-5-[4-(trifluoroacetyl)phenoxy]-1H-pyrazol-3-yl}phenyl)-1-methylethyl]-2,2,2-trifluoroethanesulfonamide;

4-({1-ethyl-3-[3-(1-methyl-1-{[(2,2,2-trifluoroethyl)sulfonyl]amino}ethyl)phenyl]-1H-pyrazol-5-yl}oxy)-N-(tetrahydrofuran-2-ylmethyl)benzamide;

N-[1-(3-{1-ethyl-5-[4-(5-methyl-1,3,4-oxadiazol-2-yl)phenoxy]-1H-pyrazol-3-yl}phenyl)-1-methylethyl]-2,2,2-trifluoroethanesulfonamide;

N-[1-(3-{1-ethyl-5-[4-(1,3-oxazol-5-yl)phenoxy]-1H-pyrazol-3-yl}phenyl)-1-methylethyl]-2,2,2-trifluoroethanesulfonamide;

N-(1-{3-[1-ethyl-5-(4-{[(tetrahydrofuran-2-ylmethyl)amino]methyl}phenoxy)-1H-pyrazol-3-yl]phenyl}-1-methylethyl)-2,2,2-trifluoroethanesulfonamide;

N-(1-{3-[1-ethyl-5-(4-{[(pyridin-2-ylmethyl)amino]methyl}phenoxy)-1H-pyrazol-3-yl]phenyl}-1-methylethyl)-2,2,2-trifluoroethanesulfonamide;

N-[1-(3-{1-ethyl-5-[4-(morpholin-4-ylmethyl)phenoxy]-1H-pyrazol-3-yl}phenyl)-1-methylethyl]-2,2,2-trifluoroethanesulfonamide;

N-{1-[3-(5-{4-[(benzylamino)methyl]phenoxy}-1-ethyl-1H-pyrazol-3-yl)phenyl]-1-methylethyl}-2,2,2-trifluoroethanesulfonamide;

N-(1-{3-[1-ethyl-5-(4-{[4-(trifluoromethyl)-3,6-dihydropyridin-1(2H)-yl]methyl}phenoxy)-1H-pyrazol-3-yl]phenyl}-1-methylethyl)-2,2,2-trifluoroethanesulfonamide;

methyl N-[4-({1-ethyl-3-[3-(1-methyl-1-{[(2,2,2-trifluoroethyl)sulfonyl]amino}ethyl)phenyl]-1H-pyrazol-5-yl}oxy)benzyl]glycinate;

N-(1-{3-[1-ethyl-5-(4-{[(4-methoxyphenyl)amino]methyl}phenoxy)-1H-pyrazol-3-yl]phenyl}-1-methylethyl)-2,2,2-trifluoroethanesulfonamide;

N-{1-[3-(1-ethyl-5-{4-[(isoxazol-3-ylamino)methyl]phenoxy}-1H-pyrazol-3-yl)phenyl]-1-methylethyl}-2,2,2-trifluoroethanesulfonamide;

N-[1-(3-{5-[4-(anilinomethyl)phenoxy]-1-ethyl-1H-pyrazol-3-yl}phenyl)-1-methylethyl]-2,2,2-trifluoroethanesulfonamide;

N-{1-[3-(1-ethyl-5-{4-[(pyridin-3-ylamino)methyl]phenoxy}-1H-pyrazol-3-yl)phenyl]-1-methylethyl}-2,2,2-trifluoroethanesulfonamide;

N-{1-[3-(1-ethyl-5-{4-[(1,3-thiazol-2-ylamino)methyl]phenoxy}-1H-pyrazol-3-yl)phenyl]-1-methylethyl}-2,2,2-trifluoroethanesulfonamide;

N-[1-(3-{5-[4-(1,4-dioxa-8-azaspiro[4.5]dec-8-ylmethyl)phenoxy]-1-ethyl-1H-pyrazol-3-yl}phenyl)-1-methylethyl]-2,2,2-trifluoroethanesulfonamide;

N-(1-{3-[1-ethyl-5-(4-{[(2-thienylmethyl)amino]methyl}phenoxy)-1H-pyrazol-3-yl]phenyl}-1-methylethyl)-2,2,2-trifluoroethanesulfonamide;

N-(1-{3-[1-ethyl-5-(4-{[(pyridin-4-ylmethyl)amino]methyl}phenoxy)-1H-pyrazol-3-yl]phenyl}-1-methylethyl)-2,2,2-trifluoroethanesulfonamide;

N-[1-(3-{1-ethyl-5-[4-({[(2-methyltetrahydrofuran-2-yl)methyl]amino}methyl)phenoxy]-1H-pyrazol-3-yl}phenyl)-1-methylethyl]-2,2,2-trifluoroethanesulfonamide;

N-(1-{3-[1-ethyl-5-(4-{[(tetrahydro-2H-pyran-4-ylmethyl)amino]methyl}phenoxy)-1H-pyrazol-3-yl]phenyl}-1-methylethyl)-2,2,2-trifluoroethanesulfonamide;

N-{1-[3-(1-ethyl-5-{4-[(tetrahydro-2H-pyran-3-ylamino)methyl]phenoxy}-1H-pyrazol-3-yl)phenyl]-1-methylethyl}-2,2,2-trifluoroethanesulfonamide;

N-{1-[3-(5-{4-[(4-acetylpiperazin-1-yl)methyl]phenoxy}-1-ethyl-1H-pyrazol-3-yl)phenyl]-1-methylethyl}-2,2,2-trifluoroethanesulfonamide;

N-(1-{3-[1-ethyl-5-(4-{[(pyridin-3-ylmethyl)amino]methyl}phenoxy)-1H-pyrazol-3-yl]phenyl}-1-methylethyl)-2,2,2-trifluoroethanesulfonamide;

N-[3-(3-{1-ethyl-5-[4-(trifluoromethyl)phenoxy]-1H-pyrazol-3-yl}phenyl)oxetan-3-yl]-2,2,2-trifluoroethanesulfonamide;

N-[3-(3-{1-ethyl-5-[4-(trifluoromethyl)phenoxy]-1H-pyrazol-3-yl}phenyl)oxetan-3-yl]-N'-(2,2,2-trifluoroethyl)sulfamide;

N-[3-(3-{1-ethyl-5-[4-(trifluoromethyl)phenoxy]-1H-pyrazol-3-yl}phenyl)oxetan-3-yl]-N'-methylsulfamide;

N-[3-(3-{1-ethyl-3-[4-(trifluoromethyl)phenoxy]-1H-pyrazol-5-yl}-phenyl)oxetan-3-yl]-2,2,2-trifluoroethanesulfonamide;

2,2,2-trifluoro-N-[1-(3-{1-(2-hydroxyethyl)-5-[4-(trifluoromethyl)phenoxy]-1H-pyrazol-3-yl}phenyl)-1-methylethyl]ethanesulfonamide;

2,2,2-trifluoro-N-[1-(3-{1-methyl-5-[4-(trifluoromethyl)phenoxy]-1H-pyrazol-3-yl}phenyl)cyclopropyl]ethanesulfonamide;

2,2,2-trifluoro-N-[1-(3-{1-(2,2,2-trifluoroethyl)-5-[4-(trifluoromethyl)phenoxy]-1H-pyrazol-3-yl}phenyl)cyclopropyl]ethanesulfonamide;

N-(1-{3-[5-(4-cyanophenoxy)-1-ethyl-1H-pyrazol-3-yl]phenyl}-1-methylethyl)-2,2,2-trifluoroethanesulfonamide;

N-[1-(3-{1-ethyl-5-[4-(trifluoromethyl)phenoxy]-1H-pyrazol-3-yl}phenyl)cyclobutyl]-2,2,2-trifluoroethanesulfonamide;

N-[1-(3-{1-ethyl-4-fluoro-3-[4-(trifluoromethyl)phenoxy]-1H-pyrazol-5-yl}phenyl)cyclopropyl]-2,2,2-trifluoroethanesulfonamide;

N-[1-(3-{4-chloro-1-ethyl-5-[4-(trifluoromethyl)phenoxy]-1H-pyrazol-3-yl}phenyl)cyclopropyl]-2,2,2-trifluoroethanesulfonamide;

N-[2-(3-{4-chloro-1-ethyl-5-[4-(trifluoromethyl)phenoxy]-1H-pyrazol-3-yl}-phenyl)propan-2-yl]-2,2,2-trifluoroethanesulfonamide;

N-[2-(3-{4-chloro-1-ethyl-3-[4-(trifluoromethyl)phenoxy]-1H-pyrazol-5-yl}-phenyl)propan-2-yl]-2,2,2-trifluoroethanesulfonamide;

N-[2-(3-{4-Bromo-1-ethyl-3-[4-(trifluoromethyl)phenoxy]-1H-pyrazol-5-yl}phenyl)propan-2-yl]-2,2,2-trifluoroethanesulfonamide;

N-[2-(3-{4-bromo-1-ethyl-5-[4-(trifluoromethyl)phenoxy]-1H-pyrazol-3-yl}phenyl)propan-2-yl]-2,2,2-trifluoroethanesulfonamide;

N-[2-(3-{1-ethyl-4-iodo-5-[4-(trifluoromethyl)phenoxy]-1H-pyrazol-3-yl}phenyl)propan-2-yl]-2,2,2-trifluoroethanesulfonamide;

N-[2-(3-{4-cyano-1-ethyl-5-[4-(trifluoromethyl)phenoxy]-1H-pyrazol-3-yl}phenyl)propan-2-yl]-2,2,2-trifluoroethanesulfonamide;

N-[2-(3-{1-ethyl-4-formyl-5-[4-(trifluoromethyl)phenoxy]-1H-pyrazol-3-yl}phenyl)propan-2-yl]-2,2,2-trifluoroethanesulfonamide;

N-[2-(3-{1-ethyl-4-(phenylethynyl)-5-[4-(trifluoromethyl)phenoxy]-1H-pyrazol-3-yl}phenyl)propan-2-yl]-2,2,2-trifluoroethanesulfonamide;

N-[5-(1-Ethyl-3-(4-trifluoromethylphenoxy)-1H-pyrazol-5-yl)-2,3-dihydro-1H-inden-2-yl]-N'-(2,2,2-trifluoroethyl)sulfuric diamide;

N-[5-(1-Ethyl-5-(4-trifluoromethylphenoxy)-1H-pyrazol-3-yl)-2,3-dihydro-1H-inden-2-yl]-N'-(2,2,2-trifluoroethyl)sulfuric diamide;

N-[5-(1-ethyl-3-{[5-(trifluoromethyl)pyridin-2-yl]oxy}-1H-pyrazol-5-yl)-2,3-dihydro-1H-inden-2-yl]-N'-(2,2,2-trifluoroethyl)sulfamide;

N-(5-{1-ethyl-3-[4-(trifluoromethyl)phenoxy]-1H-pyrazol-5-yl}-2,3-dihydro-1H-inden-2-yl)-N'-propylsulfamide;

N-(5-{1-ethyl-3-[4-(trifluoromethyl)phenoxy]-1H-pyrazol-5-yl}-2,3-dihydro-1H-inden-2-yl)-N'-isobutylsulfamide; and N-cyclobutyl-N'-(5-{1-ethyl-3-[4-(trifluoromethyl)phenoxy]-1H-pyrazol-5-yl}-2,3-dihydro-1H-inden-2-yl)sulfamide;

N-cyclopropyl-N-[3-(3-{1-ethyl-5-[4-(trifluoromethyl)phenoxy]-1H-pyrazol-3-yl}phenyl)oxetan-3-yl]sulfamide;

N-(3,3-difluorocyclopentyl)-N-[3-(3-{1-ethyl-5-[4-(trifluoromethyl)phenoxy]-1H-pyrazol-3-yl}phenyl)oxetan-3-yl]sulfamide;

N-[3-(3-{1-ethyl-3-[4-(trifluoromethyl)phenoxy]-1H-pyrazol-5-yl}phenyl)oxetan-3-yl]-N'-(2,2,2-trifluoropropyl)sulfamide;

N-(cyclobutylmethyl)-N-[3-(3-{1-ethyl-3-[4-(trifluoromethyl)phenoxy]-1H-pyrazol-5-yl}phenyl)oxetan-3-yl]sulfamide;

N-cyclopropyl-N-[3-(3-{1-ethyl-3-[4-(trifluoromethyl)phenoxy]-1H-pyrazol-5-yl}phenyl)oxetan-3-yl]sulfamide;

N-[3-(5-{1-ethyl-5-[4-(trifluoromethyl)phenoxy]-1H-pyrazol-3-yl}pyridine-3-yl)oxetan-3-yl]-2,2,2-trifluoroethanesulfonamide;

N-[3-(5-{1-ethyl-5-[4-(trifluoromethyl)phenoxy]-1H-pyrazol-3-yl}pyridine-3-yl)oxetan-3-yl]-N'-(2,2,2-trifluoroethyl)sulfamide;

N-(3-{3-[5-(4-cyanophenoxy)-1-ethyl-1H-pyrazol-3-yl]phenyl}oxetane-3-yl)-2,2,2-trifluoroethanesulfonamide;

N-(3-{3-[5-(4-cyanophenoxy)-1-ethyl-1H-pyrazol-3-yl]phenyl}oxetane-3-yl)-N-(2,2,2-trifluoroethyl)sulfamide;

N-(3-{3-[5-(4-cyanophenoxy)-1-ethyl-1H-pyrazol-3-yl]phenyl}oxetane-3-yl)-N'-(3,3-difluorocyclobutyl)sulfamide;

2-[5-(4-trifluoromethylphenoxy)-3-(3-{3-[(2,2,2-trifluoroethylsulfonyl)amino]oxetan-3-yl}phenyl)-1H-pyrazol-1-yl]-N,N-dimethylacetamide;

2-[5-(4-trifluoromethylphenoxy)-3-(3-{3-[(2,2,2-trifluoroethylsulfonyl)amino]oxetan-3-yl}phenyl)-1H-pyrazol-1-yl]-N-methylacetamide;

N-[3-(3-{5-(4-trifluoromethylphenoxy)-1-[2-oxo-2-(morpholin-4-yl)ethyl]-1H-pyrazol-3-yl}phenyl)oxetan-3-yl]-2,2,2-trifluoroethanesulfonamide;

N-(3-{3-[5-(4-trifluoromethylphenoxy)-1-(1,3-oxazol-4-ylmethyl)-1H-pyrazol-3-yl]phenyl}oxetan-3-yl)-2,2,2-trifluoroethanesulfonamide;

N-(3-{3-[3-(4-trifluoromethylphenoxy)-1-(1,3-oxazol-4-ylmethyl)-1H-pyrazol-5-yl]phenyl}oxetan-3-yl)-2,2,2-trifluoroethanesulfonamide;

N-(3-{3-[5-(4-trifluoromethylphenoxy)-1-(5-methyl-1,3,4-oxadiazol-2-ylmethyl)-1H-pyrazol-3-yl]phenyl}oxetan-3-yl)-2,2,2-trifluoroethanesulfonamide;

N-(3-{3-[5-(4-trifluoromethylphenoxy)-1-(5-methyl-1,2-isoxazol-3-ylmethyl)-1H-pyrazol-3-yl]phenyl}oxetan-3-yl)-2,2,2-trifluoroethanesulfonamide;

N-(3-{3-[5-(4-trifluoromethylphenoxy)-1-(tetrahydrofuran-2-ylmethyl)-1H-pyrazol-3-yl]phenyl}oxetan-3-yl)-2,2,2-trifluoroethanesulfonamide;

N-(3-{3-[5-(4-trifluoromethylphenoxy)-1-(tetrahydro-2H-pyran-4-ylmethyl)-1H-pyrazol-3-yl]phenyl}oxetan-3-yl)-2,2,2-trifluoroethanesulfonamide;

N-(3-{3-[5-(4-trifluoromethylphenoxy)-1-(tetrahydro-2H-pyran-4-ylmethyl)-1H-pyrazol-2-yl]phenyl}oxetan-3-yl)-2,2,2-trifluoroethanesulfonamide;

N-(3-{3-[5-(4-trifluoromethylphenoxy)-1-(2-methoxyethyl)-1H-pyrazol-2-yl]phenyl}oxetan-3-yl)-2,2,2-trifluoroethanesulfonamide;

N-(3-{3-[5-(4-trifluoromethylphenoxy)-1-(3-methoxypropyl)-1H-pyrazol-2-yl]phenyl}oxetan-3-yl)-2,2,2-trifluoroethanesulfonamide;

or a pharmaceutically acceptable salt of any of the foregoing compounds.

17. A pharmaceutical composition comprising a compound according to claim 1 or a pharmaceutically acceptable salt thereof and a pharmaceutically acceptable carrier.

* * * * *